(12) United States Patent
Ahlquist et al.

(10) Patent No.: US 10,883,144 B2
(45) Date of Patent: Jan. 5, 2021

(54) DETECTING COLORECTAL NEOPLASM

(71) Applicants: Mayo Foundation for Medical Education and Research, Rochester, MN (US); EXACT SCIENCES DEVELOPMENT COMPANY, LLC, Madison, WI (US)

(72) Inventors: David A. Ahlquist, Rochester, MN (US); William R. Taylor, Lake City, MN (US); Douglas W. Mahoney, Elgin, MN (US); Graham P. Lidgard, Madison, WI (US); Hatim T. Allawi, Middleton, WI (US)

(73) Assignees: Mayo Foundation for Medical Education and Research, Rochester, MN (US); Exact Sciences Development Company, LLC, Madison, WI (US)

( * ) Notice: Subject to any disclaimer, the term of this patent is extended or adjusted under 35 U.S.C. 154(b) by 0 days.

(21) Appl. No.: 16/738,718

(22) Filed: Jan. 9, 2020

(65) Prior Publication Data
US 2020/0131588 A1   Apr. 30, 2020

Related U.S. Application Data

(63) Continuation of application No. 15/301,227, filed as application No. PCT/US2015/022749 on Mar. 26, 2015.

(60) Provisional application No. 61/972,942, filed on Mar. 31, 2014, provisional application No. 61/977,954, filed on Apr. 10, 2014.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/154* (2013.01)

(58) Field of Classification Search
CPC ............ C12Q 1/6886; C12Q 2600/154; C12Q 2600/112
See application file for complete search history.

(56) References Cited

U.S. PATENT DOCUMENTS

| | | |
|---|---|---|
| 5,352,775 A | 10/1994 | Albertsen |
| 5,362,623 A | 11/1994 | Vogelstein |
| 5,527,676 A | 6/1996 | Vogelstein |
| 5,541,308 A | 7/1996 | Hogan |
| 5,648,212 A | 7/1997 | Albertsen |
| 5,670,325 A | 9/1997 | Lapidus et al. |
| 5,691,454 A | 11/1997 | Albertsen |
| 5,741,650 A | 4/1998 | Lapidus et al. |
| 5,783,666 A | 7/1998 | Albertsen |
| 5,786,146 A | 7/1998 | Herman |
| 5,891,651 A | 4/1999 | Roche |
| 5,928,870 A | 7/1999 | Lapidus et al. |
| 5,952,178 A | 9/1999 | Lapidus et al. |
| 5,955,263 A | 9/1999 | Vogelstein |
| 6,020,137 A | 2/2000 | Lapidus et al. |
| RE36,713 E | 5/2000 | Vogelstein |
| 6,090,566 A | 7/2000 | Vogelstein |
| 6,114,124 A | 9/2000 | Albertsen |
| 6,235,470 B1 | 5/2001 | Sidransky |
| 6,245,515 B1 | 6/2001 | Vogelstein |
| 6,413,727 B1 | 7/2002 | Albertsen |
| 6,630,314 B2 | 10/2003 | Nair et al. |
| 6,677,312 B1 | 1/2004 | Vogelstein |
| 6,800,617 B1 | 10/2004 | Vogelstein |
| RE38,916 E | 12/2005 | Vogelstein |
| 7,037,650 B2 | 5/2006 | Gonzalgo et al. |
| 7,087,583 B2 | 8/2006 | Vogelstein |
| 7,267,955 B2 | 9/2007 | Vogelstein |
| 7,368,233 B2 | 5/2008 | Shuber et al. |
| 7,432,050 B2 | 10/2008 | Markowitz |
| 7,485,402 B2 | 2/2009 | Arai |
| 7,485,418 B2 | 2/2009 | Goggins |
| 8,361,720 B2 | 1/2013 | Oldham-Haltom |
| 8,808,990 B2 | 8/2014 | Lidgard et al. |
| 8,969,046 B2 | 3/2015 | Van Engeland et al. |
| 8,980,107 B2 | 3/2015 | Domanico et al. |
| 8,993,341 B2 | 3/2015 | Bruinsma et al. |
| 8,999,176 B2 | 4/2015 | Domanico et al. |
| 9,000,146 B2 | 4/2015 | Bruinsma et al. |
| 9,506,116 B2 | 11/2016 | Ahlquist et al. |
| 2003/0143606 A1 | 7/2003 | Olek et al. |
| 2003/0224040 A1 | 12/2003 | Baylin et al. |
| 2004/0234960 A1 | 11/2004 | Hogan |
| 2006/0253259 A1 | 11/2006 | Fernandez |
| 2007/0054295 A1 | 3/2007 | Spivack |
| 2008/0039413 A1 | 2/2008 | Morris et al. |
| 2008/0081333 A1 | 4/2008 | Mori et al. |
| 2008/0213870 A1 | 9/2008 | Cao et al. |
| 2009/0208505 A1 | 8/2009 | Samuels |
| 2010/0167940 A1 | 7/2010 | Feinberg |
| 2010/0317000 A1 | 12/2010 | Zhu |
| 2011/0136687 A1 | 6/2011 | Olek et al. |
| 2011/0183328 A1 | 7/2011 | Taylor et al. |
| 2011/0287968 A1 | 11/2011 | Weinhausel et al. |
| 2011/0318738 A1 | 12/2011 | Jones et al. |

(Continued)

FOREIGN PATENT DOCUMENTS

| | | |
|---|---|---|
| EP | 2391729 | 12/2011 |
| WO | WO 00/26401 | 5/2000 |

(Continued)

OTHER PUBLICATIONS

Moon et al., Journal of Experimental & Clinical Cancer Research, 33:4, 1-10, (Year: 2014).*

(Continued)

*Primary Examiner* — Cynthia B Wilder
(74) *Attorney, Agent, or Firm* — Casimir Jones, SC; Robert A. Goetz

(57) ABSTRACT

Provided herein is technology relating to detecting neoplasia and particularly, but not exclusively, to methods, compositions, and related uses for detecting premalignant and malignant neoplasms such as colorectal cancer.

5 Claims, No Drawings

Specification includes a Sequence Listing.

(56) References Cited

U.S. PATENT DOCUMENTS

| | | |
|---|---|---|
| 2012/0034605 A1 | 2/2012 | Hinoda et al. |
| 2012/0053073 A1 | 3/2012 | Kassis et al. |
| 2012/0122088 A1 | 5/2012 | Zou |
| 2012/0122106 A1 | 5/2012 | Zou |
| 2012/0164110 A1 | 6/2012 | Feinberg et al. |
| 2012/0164238 A1 | 6/2012 | Louwagie |
| 2013/0012410 A1 | 1/2013 | Zou et al. |
| 2013/0022974 A1 | 1/2013 | Chinnaiyan |
| 2013/0065228 A1 | 3/2013 | Hinoue |
| 2013/0244235 A1 | 9/2013 | Ahlquist et al. |
| 2013/0288247 A1 | 10/2013 | Mori |
| 2014/0057262 A1 | 2/2014 | Ahlquist et al. |
| 2014/0137274 A1 | 5/2014 | Ishikawa |
| 2014/0162894 A1 | 6/2014 | Hatchwell et al. |
| 2014/0193813 A1 | 7/2014 | Bruinsma |
| 2014/0194607 A1 | 7/2014 | Bruinsma |
| 2014/0194608 A1 | 7/2014 | Bruinsma |
| 2014/0274748 A1 | 9/2014 | Ahlquist |
| 2014/0358448 A1 | 12/2014 | Tai et al. |
| 2015/0126374 A1 | 5/2015 | Califano |
| 2015/0240318 A1 | 8/2015 | Van Engeland et al. |
| 2016/0194723 A1 | 7/2016 | Louwagie |

FOREIGN PATENT DOCUMENTS

| | | |
|---|---|---|
| WO | WO 2007/116417 | 10/2007 |
| WO | WO 2008/084219 | 7/2008 |
| WO | WO 2009/114836 | 9/2009 |
| WO | WO 2010/086389 | 8/2010 |
| WO | WO 2010/089538 | 8/2010 |
| WO | WO 2011/119934 | 9/2011 |
| WO | WO 2011/126768 | 10/2011 |
| WO | WO 2012/088298 | 6/2012 |
| WO | WO 2012/155072 | 11/2012 |
| WO | WO 2012/175562 | 12/2012 |
| WO | WO 2013/026104 | 2/2013 |
| WO | WO 2016/097120 | 6/2016 |

OTHER PUBLICATIONS

Ahlquist D et al. (2010) "Next Generation Stool DNA Testing for Detection of Colorectal Neoplasia — Early Marker Evaluation", presented at *Colorectal Cancer: Biology to Therapy*, American Association for Cancer Research.

Ahlquist D.A. et al., "Novel use of hypermethylated DNA markers in stool for detection of colorectal cancer: a feasibility study." Gastroenterology, 2002;122(Suppl):A40.

Ahlquist D.A., et al., "Colorectal cancer screening by detection of altered human DNA in stool: feasibility of a multitarget assay panel." Gastroenterology, 2000, 119(5):1219-27.

Ahlquist et al., "Next-generation stool DNA test accurately detects colorectal cancer and large adenomas." Gastroenterology (2012), 142, pp. 248-56.

Asai et al. "IKZF1 deletion is associated with a poor outcome in pediatric B-cell precursor acute lymphoblastic leukemia in Japan." Cancer Med. 2013; 2:412-9.

Aust De, "Mutations of the BRAF gene in ulcerative colitis-related colorectal carcinoma." Int. J. Cancer (2005), 115, pp. 673-7.

Azuara et al. "Novel Methylation Panel for the Early Detection of Colorectal Tumors in Stool DNA." Clinical Colorectal Cancer, vol. 9, No. 3, pp. 168-176, Jul. 2010.

Baxter, Eva "Investigating the association between BRAFv600E and methylation in sporadic colon cancer" PhD The University of Edinburgh, 2011.

Belinsky S.A., et al., "Promoter Hypermethylation of Multiple Genes in Sputum Precedes Lung Cancer Incidence in a High-Risk Cohort." Cancer Res, 2006;66:3338-44.

Bell et al., "c-Ki-ras gene mutations in dysplasia and carcinomas complicating ulcerative colitis." Br J Cancer (1991), 64, pp. 174-8.

Biankin et al. (2003) "Molecular pathogenesis of precursor lesions of pancreatic ductal adenocarcinoma" Pathology 35:14-24.

Brune, et al. (2008). "Genetic and epigenetic alterations of familial pancreatic cancers." Cancer Epidemiol Biomarkers Prev. 17 (12): 3536-3542.

Cairns et al., "Guidelines for colorectal cancer screening and surveillance in moderate and high risk groups." Gut (2010); 59, pp. 666-89.

Cameron et al (1995) "Adenocarcinoma of the esophagogastric junction and Barrett's esophagus" Gastroenterology 109: 1541-1546.

Camoes et al. "Potential downstream target genes of aberrant ETS transcription factors are differentially affected in Ewing's sarcoma and prostate carcinoma." PLoS ONE. 2012;7:e49819.

Campbell et al. "Aberrant expression of the neuronal transcription factor FOXP2 in neoplastic plasma cells." British journal of haematology. 2010; 149:221-30.

Chen W.D., et al., "Detection in Fecal DNA of Colon Cancer—Specific Methylation of the Nonexpressed Vimentin Gene." J Natl Cancer Inst 2005;97:1124-32.

Eads, et al. (1999). "CpG island hypermethylation in human colorectal tumors is not associated with DNA methyltransferase overexpression." Cancer Res. 59: 2302-2306.

Ebert M.P., et al., "Aristaless-like homeobox-4 gene methylation is a potential marker for colorectal adenocarcinomas." Gastroenterology 2006;131:1418-30.

Edge, S.; Fritz, A.G.; Greene, F.L.; Trotti, A. (Eds.), AJCC Cancer Staging Manual. 7th ed: Springer, New York; 2010; Book-only table of contents provided.

Garrity-Park et al. "Methylation status of genes in non-neoplastic mucosa from patients with ulcerative colitis-associated colorectal cancer." Am J Gastroenterol (2010), 105, pp. 1610-9.

Glockner, et al. (2009). "Methylation of TFPI2 in stool DNA: a potential novel biomarker for the detection of colorectal cancer." Cancer Res. 69: 4691-4699.

Goggins, M. "Molecular markers of early pancreatic cancer." J Clin Oncol 2005; 23: 4524.

Gonzalgo, et al. (1997) "Identification and characterization of differentially methylated regions of genomic DNA by methylation-sensitive arbitrarily primed PCR." Cancer Res. 57: 594-599.

Gonzalgo, et al. (1997). "Rapid quantitation of methylation differences at specific sites using methylation-sensitive single nucleotide primer extension (Ms-SNuPE)." Nucleic Acids Res. 25 (12): 2529-2531.

Grady W.M., et al., "Detection of Aberrantly Methylated hMLH1 Promoter DNA in the Serum of Patients with Microsatellite Unstable Colon Cancer 1." Cancer Res, 2001;61:900-2.

Grutzmann et al., "Sensitive Detection of Colorectal Cancer in Peripheral Blood by Septin 9 DNA Methylation Assay." PLoS One (2008), 3:e3759.

Gu et al. "Genome-scale DNA methylation mapping of clinical samples at single-nucleotide resolution." Nat Methods. 2010; 7:133-6.

Gu, et al. (2011). "Preparation of reduced representation bisulfite sequencing libraries for genome-scale DNA methylation profiling." Nature Protocols. 6 (4): 468-481.

Gurung et al. "Menin epigenetically represses Hedgehog signaling in MEN1 tumor syndrome." Cancer research. 2013;73:2650-8.

Herman, et al. (1996). "Methylation-specific PCR: A novel PCR assay for methylation status of CpG islands." Proc. Natl. Acad. Sci. USA. 93: 9821-9826.

Hibi et al. (2010) "Methylation of the TFPI2 gene is frequently detected in advanced gastric carcinoma" *Anticancer Res* 30: 4131-3.

Hibi, et al. (2010). "Methylation of TFPI2 gene is frequently detected in advanced well-differentiated colorectal cancer." Anticancer Res. 30: 1205-1207.

Hirota et al., "pS2 expression as a possible diagnostic marker of colorectal carcinoma in ulcerative colitis." Oncol Rep (2000), 7, pp. 233-9.

Holzmann et al., "Comparative analysis of histology, DNA content, p53 and Ki-ras mutations in colectomy specimens with long-standing ulcerative colitis." Int J Cancer (1998) 76, pp. 1-6.

Hong, et al. (2008). "Multiple genes are hypermethylated in intraductal papillary mucinous neoplasms of the pancreas." Mod Pathol. 21 912): 1499-1507.

(56) References Cited

OTHER PUBLICATIONS

Hoque M.O., et al., "Quantitative methylation-specific polymerase chain reaction gene patterns in urine sediment distinguish prostate cancer patients from control subjects." J Clin Oncol, 2005;23:6569-75.
Howe, et al., "Annual report to the nation on the status of cancer, 1975-2003, featuring cancer among U.S. Hispanic/Latino populations." Cancer (2006) 107, pp. 1711-42.
Imperiale et al., "Fecal DNA versus fecal occult blood for colorectal-cancer screening in an average-risk population." n. Engl J Med (2004), 351, pp. 2704-14.
International Search Report and Written Opinion, Int'l Patent Application No. PCT/US2015/022749, dated Aug. 19, 2015, 12 pages.
International Search Report and Written Opinion, Int'l Patent Application No. PCT/US2015/022751, dated Aug. 26, 2015, 25 pages.
International Search Report dated Jun. 10, 2013 from related International Patent Application No. PCT/US2013/027227.
Issa et al., "Accelerated Age-related CpG Island Methylation in Ulcerative Colitis." Cancer Res (2001), 61, pp. 3573-3577.
Itzkowitz et al. "Diagnosis and management of dysplasia in patients with inflammatory bowel diseases." Gastroenterology (2004) 126, pp. 1634-48.
Itzkowitz S.H., et al., "Improved fecal DNA test for colorectal cancer screening." Clin Gastroenterol Hepatol 2007;5:111-7.
Jacobs et al. "Dysregulated methylation at imprinted genes in prostate tumor tissue detected by methylation microarray." BMC Urol. 2013;13:37.
Jess et al., "Risk of intestinal cancer in inflammatory bowel disease: a population-based study from olmsted county, Minnesota." Gastroenterology (2006) 130, pp. 1039-46.
Jiao et al. "Somatic mutations in the Notch, NF-KB, PIK3CA, and Hedgehog pathways in human breast cancers." Genes, chromosomes & cancer. 2012; 51:480-9.
Kaiser. (2008). "Cancer genetics. A detailed genetic portrait of the deadliest human cancers." Science. 321: 1280-1281.
Kann L., et al., "Improved marker combination for detection of de novo genetic variation and aberrant DNA in colorectal neoplasia." Clin Chem 2006;52:2299-302.
Kawai, et al. (1994). "Comparison of DNA methylation patterns among mouse cell lines by restriction landmark genomic screening." Mol. Cell Biol. 14 (11): 7421-7427.
Kisiel et al. "Stool DNA testing for the detection of pancreatic cancer: assessment of methylation marker candidates." Cancer. 2012; 118:2623-31.
Kisiel et al. (AGA Abstracts, VS-68, vol. 138, No. 5, May 2010).
Kisiel, et al. (2011). "Stool DNA screening for colorectal cancer: opportunities to improve value with next generation tests." J Clin Gastroenterol. 45 (4): 301-8.
Kober et al. "Methyl-CpG binding column-based identification of nine genes hypermethylated in colorectal cancer." Molecular carcinogenesis. 2011; 50:846-56.
Kraus, et al., "Inflammation and colorectal cancer," Current Opinion in Pharmacology, vol. 9, No. 4, pp. 405-410 (2009).
Kuppuswamy et al. "Single nucleotide primer extension to detect genetic diseases: Experimental application to hemophilia B (factor IX) and cystic fibrosis genes" (1991) Proc. Natl. Acad. Sci. USA 88: 1143-1147.
Laird. (2010). "Principles and challenges of genome-wide DNA methylation analysis." Nat Rev Genet. 11: 191-203.
Lashner Ba, Am J Gastroenterol (1999), 94, pp. 456-62.
Lee et al. "Pituitary homeobox 2 (PITX2) protects renal cancer cell lines against doxorubicin toxicity by transcriptional activation of the multidrug transporter ABCB1." International journal of cancer Journal international du cancer. 2013; 133:556-67.
Leung W.K., et al., "Detection of epigenetic changes in fecal DNA as a molecular screening test for colorectal cancer: A feasibility study." Clin Chem 2004; 50(11):2179-82.
Levin B, Gastroenterology (2008); 134, pp. 1570-95.

Li et al. "Association between Galphai2 and ELMO1/Dock180 connects chemokine signalling with Rac activation and metastasis." Nat Commun. 2013; 4:1706.
Lim, et al. (2010). "Cervical dysplasia: assessing methylation status (Methylight) of CCNA1, DAPK1, HS3ST2, PAX1 and TFPI2 (to improve diagnostic accuracy." Gynecol Oncol. 119: 225-231.
Lin, et al., Identification of disease-associated DNA methylation in intestinal tissues from patients with inflammatory bowel disease, Clinical Genetics, vol. 80, No. 1, pp. 59-67 (2011).
Liu et al. "Medulloblastoma expresses CD1d and can be targeted for immunotherapy with NKT cells." Clin Immunol. 2013;149:55-64.
Ma, et al. (2011). "MicroRNA-616 induces androgen-independent growth of prostate cancer cells by suppressing expression of tissue factor pathway inhibitor TFPI-2." Cancer Res. 71: 583-592.
Maeda, et al., "DNA hypermethylation in colorectal neoplasms and inflammatory bowel disease: a mini review," Inflammapharmacology, vol. 14, No. 5-6, pp. 204-206 (2006).
Matsubayashi, et al. (2006). "DNA methylation alterations in the pancreatic juice of patients with suspected pancreatic disease." Cancer Res. 66: 1208-1217.
Meissner et al. (2008). "Genome-scale DNA methylation maps of pluripotent and differentiated cells." Nature. 454: 766-70.
Melotte et al., (JNCL, vol. 101, No. 13, pp. 916-927, Jul. 2009).
Muller H.M., et al., "Methylation changes in faecal DNA: a marker for colorectal cancer screening?" The Lancet 2004;363:1283-5.
Obusez et al. (Inflammatory Bowel Diseases: vol. 14, Issue pS42, Dec. 2008, P-0106).
Obusez et al. (Int. J. Colorectal Dis. vol. 26, pp. 951-953, 2011).
Odze Rd, Am J Surg Pathol (2000), 24, pp. 1209-16.
Olaru, et al., "Unique patterns of CpG island methylation in inflammatory bowel disease-associated colorectal cancers," Inflammatory Bowel Diseases, vol. 18, No. 4, pp. 641-648 (Epub Aug. 9, 2011).
Olson, J et al. "DNA Stabilization Is Critical for Maximizing Performance of Fecal DNA-Based Colorectal Cancer Tests" Diagn Mol Pathol (2005) 14, pp. 183-91.
Omura, et al. (2008). "Genome-wide profiling of methylated promoters in pancreatic adenocarcinoma." Cancer Biol Ther. 7 (7): 1146-1156.
Omura, et al. (2009). "Epigenetics and epigenetic alterations in pancreatic cancer." Int. J. Clin Exp Pathol. 2: 310-326.
Osborn Nk, and Ahlquist Da, "Stool screening for colorectal cancer: molecular approaches." Gastroenterology 2005;128:192-206.
Osborn, et al., "Aberrant methylation of the eyes absent 4 gene in ulcerative colitis-associated dysplasia," Clinical Gastroenterology and Hepatology, vol. 4, No. 2, pp. 212-218 (2006).
Oster, B. et al., "Identification and validation of highly frequent CpG island hypermethylation in colorectal adenomas and carcinomas." Int J Cancer. 2011;129(12):2855-66.
Person et al. "Chronic cadmium exposure in vitro induces cancer cell characteristics in human lung cells." Toxicol Appl Pharmacol. 2013; 273(2):281-8.
Petko Z., et al., "Aberrantly Methylated CDKN2A, MGMT, and MLH1 in Colon Polyps and in Fecal DNA from Patients with Colorectal Polyps." Clin Cancer Res 2005;11:1203-9.
Raimondo et al. "Methylated DNA Markers in Pancreatic Juice Discriminate Pancreatic Cancer From Chronic Pancreatitis and Normal Controls" Gastroenterology 2013; 144:S-90.
Rex et al. "American College of Gastroenterology guidelines for colorectal cancer screening 2008." Am J Gastroenterol (2009); 104, pp. 739-50.
Ruppenthal et al. "TWIST1 Promoter Methylation in Primary Colorectal Carcinoma" Pathol. Oncol. Res., 2011, 17:867-872.
Sadri and Hornsby "Rapid Analysis of DNA Methylation Using New Restriction Enzyme Sites Created by Bisulfite Modification." (1996) *Nucl. Acids Res.* 24: 5058-5059.
Sato et al., "Aberrant methylation of the HPP1 gene in ulcerative colitis-associated colorectal carcinoma." Cancer Res (2002), 62, pp. 6820-2.
Sato, et al. (2003). "Discovery of novel targets of aberrant methylation in pancreatic carcinoma using high-throughput microarrays." Cancer Res. 63: 3735-3742.

(56) References Cited

OTHER PUBLICATIONS

Sato, et al. (2008). "CpG island methylation profile of pancreatic intraepithelial neoplasia." Mod Pathol. 21 93): 238-244.
Schulmann, et al., Molecular phenotype of inflammatory bowel disease-associated neoplasms with microsatellite instability, Gastroenterology, vol. 129, No. 1, pp. 74-85 (2005).
Seshagiri et al. "Recurrent R-spondin fusions in colon cancer." Nature. 2012; 488:660-4.
Shin et al. "Bile-based detection of extrahepatic cholangiocarcinoma with quantitative DNA methylation markers and its high sensitivity." The Journal of molecular diagnostic: JMD. 2012;14:256-63.
Singer-Sam et al. "A quantitative HpaII-PCR assay to measure methylation of DNA from a small number of cells" (1990) Nucl. Acids Res. 18(3): 687.
Singer-Sam et al. "A sensitive, quantitative assay for measurement of allele-specific transcripts differing by a single nucleotide." (1992) PCR Methods Appl. 1: 160-163.
Stumm et al. "Strong expression of the neuronal transcription factor FOXP2 is linked to an increased risk of early PSA recurrence in ERG fusion-negative cancers." Journal of clinical pathology. 2013;66:563-8.
Surdez et al. "Targeting the EWSR1-FLI1 oncogene-induced protein kinase PKC-beta abolishes ewing sarcoma growth." Cancer research. 2012;72:4494-503.
Szabo and Mann "Allele-specific expression and total expression levels of imprinted genes during early mouse development: implications for imprinting mechanisms." (1995) Genes Dev. 9(24): 3097-3108.
Tang, et al. (2010). "Prognostic significance of tissue factor pathway inhibitor 2 in pancreatic carcinoma and its effect on tumor invasion and metastatis." Med Oncol. 27: 867-875.
Taylor et al. "Expression of p53 in colorectal cancer and dysplasia complicating ulcerative colitis." Br J Surg (1993), 80, pp. 442-4.
Tonack, et al. (2009). "Pancreatic cancer: proteomic approaches to a challenging disease." Pancreatology. 9: 567-576.
Toyota, et al. (1999). "Identification of differentially methylated sequences in colorectal cancer by methylated CpG island amplification." Cancer Res. 59: 2307-2312.
Tsunoda, et al. (2009). "Methylation of CLDN6, FBN2, RBP1, RBP4, TFPI2 and TMEFF2 in esophageal squamous cell carcinoma." Oncol Rep. 21: 1067-1073.
Vincent et al. "Genome-wide analysis of promoter methylation associated with gene expression profile in pancreatic adenocarcinoma." Clinical cancer research: an official journal of the American Association for Cancer Research. 2011; 17:4341-54.
Watanabe, t., International Journal of Oncology (2011), 38, pp. 201-7.
Wheeler et al. "Hypermethylation of the promoter region of the E-cadherin gene (CDH1) in sporadic and ulcerative colitis associated colorectal cancer." Gut (2001), 48, pp. 367-71.
Wu, Gastroenterology (2011) 14: S-222.
Xiong, et al. (1997). Nucleic Acids Res. 25 (12): 2532-2534.
Yachida, et al. (2010). "Distant metastasis occurs late during the genetic evolution of pancreatic cancer." Nature. 467: 1114-1117.
Yamaguchi, et al. (2005). "Pancreatic juice cytology in intraductal papillary mucinous neoplasm of the pancreas." Pancreatology. 5: 416-421.
Yang N. et al. "Methylation markers for CCNA1 and C13ORF18 are strongly associated with high-grade cervical intraepithelial neoplasia and cervical cancer in cervical scrapings." Cancer epidemiology, biomarkers & prevention: a publication of the American Association for Cancer Research, cosponsored by the American Society of Preventive Oncology. 2009;18:3000-7.
Zhang et al. (2009). "DNA methylation analysis of chromosome 21 gene promoters at single base pair and single allele resolution." PLoS Genet. 5 (3): e1000438.
Zhao et al. "Genome-wide identification of Epstein-Barr virus-driven promoter methylation profiles of human genes in gastric cancer cells." Cancer. 2013;119:304-12.
Zou H., et al., "A Sensitive Method to Quantify Human Long DNA in Stool: Relevance to Colorectal Cancer Screening." Cancer Epidemiol Biomarkers Prey 2006;15:1115-9.
Zou H.Z., et al., "Detection of aberrant p16 methylation in the serum of colorectal cancer patients." Clin Cancer Res 2002;8(1):188-91.
Zou, et al. (2007). "Highly methylated genes in colorectal neoplasia: implications for screening." Cancer Epidemial Biomarkers Prev. 16: 2686-2696.
Zou, et al. (2009). "T2036 Pan-Detection of Gastrointestinal Neoplasms by Stool DNA Testing Establishment of Feasibility." Gastroenterology. 136: A-625.
Abbaszadegan, "Stool-based DNA testing, a new noninvasive method for colorectal cancer screening, the first report from Iran," World Journal of gastroenterology: WJG, vol. 13, p. 1528-1533, 2007.
Ahlquist et al., 1984, "HemoQuant, a new quantitative assay for fecal hemoglobin. Comparison with Hemoccult." Ann Intern Med, 101: 297-302.
Ahlquist et al., 1985, "Fecal blood levels in health and disease. A study using HemoQuant." N Engl J Med, 312: 1422-8.
Ahlquist et al., 1989, "Patterns of occult bleeding in asymptomatic colorectal cancer." Cancer, 63: 1826-30.
Ahlquist et al., 1993, "Accuracy of fecal occult blood screening for colorectal neoplasia. A prospective study using Hemoccult and HemoQuant tests." JAMA, 269: 1262-7.
Ahlquist et al., 2000, "Colorectal cancer screening by detection of altered human DNA in stool: feasibility of a multitarget assay panel." Gastroenterology, 119: 1219-27.
Ahlquist et al., 2008, "Stool DNA and occult blood testing for screen detection of colorectal neoplasia." Ann Intern Med, 149: 441-501.
Allison et al., 2007, "Screening for colorectal neoplasms with new fecal occult blood tests: update on performance characteristics." J Natl Cancer Inst, 99: 1462-70.
Anderson et al. Am. J. Of Gastroenterology, Abstracts S1033, Oct. 2015.
Cameron et al. Blood, vol. 94, No. 7, pp. 2445-2451, Oct. 1999.
Crespi et al. "Colorectal cancer: a spreading but preventable disease" European Journal of Oncology. vol. 13(1). Mar. 2008. pp. 21-32.
De Kok, 2003, "Quantification and integrity analysis of DNA in the stool of colorectal cancer patients may represent a complex alternative to fecal occult blood testing." Clin Chem, 49: 2112-3.
Esteller et al. "Inactivation of Glutathione S-Transferase P1 Gene by Promoter Hypermethylation in Human Neoplasia" Cancer Resarch, vol. 58, pp. 4515-4518, Oct. 1998.
Feng "Conservation and divergence of methylation patterning in plants and animals" PNAS 2010 vol. 107, No. 19, pp. 8689-8694.
Grutzmann, et al. (2008), "Sensitive detection of colorectal cancer in peripheral blood by septin—DNA methylation assay," PLoS One 3(11): e3759 which is 8 pages long.
Guzinska-Ustymowicz et al., (2009), "Correlation between proliferation makers: PCNA, Ki-67, MCM-2 and antiapoptopic protein Bcl2 in colorectal cancer," Anticancer Research. 29:3049-3052.
Hardcastle et al., 1996, "Randomised controlled trial of faecal-occult-blood screening for colorectal cancer." Lancet, 348: 1472-7.
Harewood et al., 2000, "Fecal occult blood testing for iron deficiency: a reappraisal." Dig Dis, 18(2): 75-82.
Harewood et al., 2002, "Detection of occult upper gastrointestinal tract bleeding: performance differences in fecal occult blood tests." Mayo Clin Proc, 77: 23-28.
Heresbach et al., 2006, "Review in depth and meta-analysis of controlled trials on colorectal cancer screening by faecal occult blood test." Eur J Gastroenterol Hepatol, 18: 427-33.
Hoang et al., 1997, "BAT-26, an indicator of the replication error phenotype in colorectal cancers and cell lines." Cancer Res, 57: 300-3.
Imperiale et al. "Multitarget Stool DNA Testing for Colorectal-Cancer Screening" New England Journal of Medicine, vol. 370, No. 14, Apr. 3, 2014, pp. 1287-1297.
Imperiale et al., 2004, "Fecal DNA versus fecal occult blood for colorectal-cancer screening in an average-risk population." N Engl J Med, 351: 2704-14.

(56) References Cited

OTHER PUBLICATIONS

International Search Report and Written Opinion dated Dec. 28, 2011 from International Patent Application No. PCT/US2011/029959, international filed Mar. 25, 2011.
Jemal et al., 2007, "Cancer statistics, 2007." CA Cancer J Clin, 57: 43-66.
Kariya et al., 1987, "Revision of consensus sequence of human Alu repeats—a review." Gene, 53: 1-10.
Kim, H., et al., "Noninvasive molecular biomarkers for the detection of colorectal cancer," BMB Reports, 2008, vol. 41, No. 10, pp. 685-692.
Kronborg et al., 1996, "Randomised study of screening for colorectal cancer with faecal-occult-blood test." Lancet, 348: 1467-71.
Kronborg et al., 2004, "Randomized study of biennial screening with a faecal occult blood test: results after nine screening rounds." Scand J Gastroenterol, 39: 846-51.
Levin et al., 2008, "Screening and surveillance for the early detection of colorectal cancer and adenomatous polyps, 2008: a joint guideline from the American Cancer Society, the US Multi-Society Task Force on Colorectal Cancer, and The American College of Radiology." CA Cancer J Clin, 58: 130-60.
Lokk et al. "Methylation Markers of Early-Stage Non-Small Cell Lung Cancer" Plos One, vol. 7, No. 6, e398013, Jun. 2012.
Mandel et al., 1993, "Reducing mortality from colorectal cancer by screening for fecal occult blood. Minnesota Colon Cancer Control Study." N Engl J Med, 328: 1365-71.
Meissner, 2006, "Patterns of colorectal cancer screening uptake among men and women in the United States." Cancer Epidemiol Biomarkers Prev, 15: 389-94.
Melle, et al. (2005), "Discovery and identification of a-defensins as low abundant, tumor-derived serum markers in colorectal cancer," 129(1): 66-73 abstract only.
Melotte, et al., (Jul. 1, 2009): "N-myc downstream-regulated gene 4 (NDRG4): a candidate tumor suppressor gene and potential biomarker for colorectal cancer," J. Natl Cancer Inst 101: 916-927.
Meuwis, "Contribution of proteomics to colorectal cancer diagnosis," Acta Endoscopica, vol. 37, pp. 295-303, including translation, 2007.
Muller et al., 2004, "Methylation changes in faecal DNA: a marker for colorectal cancer screening?" Lancet, 363: 1283-5.
Nosho, et al. (2008): "PIK3CA mutation in colorectal cancer: Relationship with genetic and epigenetic alterations," Neoplasia. 10(6) 034-541, abstract only.
Olson et al., 2005, "DNA stabilization is critical for maximizing performance of fecal DNA-based colorectal cancer tests." Diagn Mol Pathol, 14: 183-91.
Osborn et al., 2005, "Stool screening for colorectal cancer: molecular approaches." Gastroenterology, 128: 192-206.
Pao et al. "The endothelin receptor B (EDNRB) promoter displays heterogeneous, site specific methylation patterns in normal and tumor cells" Human Molecular Genetics, vol. 10, No. 9, pp. 903-910.
Park, et al. (2002), "Expressiono f melanoma antigen-encoding genes (MAGE) by common primers for MAGE-A1 to —A6 in colorectal carcinomas among Koreans," J. Korean Med. Sci 17: 497-501.
Saitoh et al. (1995), "Intestinal protein loss and bleeding assessed by fecal hemoglobin, transferrin, albumin, and alpha-1-antitrypsin levels in patients with colorectal diseases," Digestion. 56(1): 67-75, abstract only.
Sambrook et al., 1989, Fritsch, E.F., Maniatis, T. (ed.), Molecular Cloning, Cold Spring Harbor Lab. Press, Cold Spring Harbor, N.Y., 30 pages.
Samowitz et al., 1999, "BAT-26 and BAT-40 instability in colorectal adenomas and carcinomas and germline polymorphisms." Am J Path, 154: 1637-41.
Schwartz et al., 1983, "The "HemoQuant" test: a specific and quantitative determination of heme (hemoglobin) in feces and other materials." Clin Chem, 29: 2061-7.
Schwartz et al., 1985, "Quantitative fecal recovery of ingested hemoglobin-heme in blood: comparisons by HemoQuant assay with ingested meat and fish." Gastroenterology, 89: 19-26.
Singh et al., 2006, "Risk of developing colorectal cancer following a negative colonoscopy examination: evidence for a 10-year interval between colonoscopies." JAMA, 295: 2366-73.
Summons to attend oral proceedings, European patent application No. 11760295.3, mailed Mar. 4, 2016.
Tibble, et al. (2001), "Faecal capprotectin and faecal occult blood tests in the diagnosis of colorectal carcinoma and adenoma.," Gut. 49:402-408.
Uchida, et al. (1994), "Immunochemical detection of human lactoferrin in feces as a new marker for inflammatorygastrointestinal disorders and colon cancer," Clinical Biochemistry. 27(4)L 259-264, abstract only.
Wang, "Gene expression profiles and molecular markers to predict recurrence of duke's B Colon Cancer," vol. 22, pp. 1564-1571, 2004.
Wen, et al. (2006), "Frequence epigenetic silencing of the bome morphogenic protein 2 gene through methylation in gastic carcinomas," Onogene. 25:2666-2673.
Winawer et al., 1993, "Screening for colorectal cancer with fecal occult blood testing and sigmoidoscopy." J Natl Cancer Inst, 85: 1311-8.
Wittekind et al. (1986), "Localization of CEA, HCG, lysozyme, alpha-1-antitrypsin, and alpha-1-antichymotrypsin in gastric cancer and prognosis," Virchows Arch 409:715-724.
Young, "Fecal Immunochemical Tests (FIT) vs. Office-based guaiac fecal occult blood test (FOBT)," Practical Gastroenterology, Colorectal Cancer, series 3, pp. 46-56, 2004.
Zijlstra et al., 2002, "A quantitative analysis of rate-limiting steps in the metastatic cascade using human-specific real-time polymerase chain reaction." Cancer Res, 62: 7083-92.
Zou et al., 2006, "A sensitive method to quantify human long DNA in stool: relevance to colorectal cancer screening." Cancer Epidemiol Biomarkers Prev, 15: 1115-9.
Zou, et al. (2007), "Highly methylated genes in colorectal neoplasia: Implications for screening," Cancer Epidemilogy Biomarkers Prev. 16(12): 2686-2696.
Zou, et al., "High Detection Rates of Colorectal Neoplasia by Stool DNA Testing with a Novel Digital Melt Curve Assay," Gastroenterology, vol. 136, No. 2, Feb. 1, 2009, pp. 459-470.
Zou, et al., "T2034 Stool DNA and Occult Blood for Detection of Colorectal Cancer: Complementary Markers," Gastroenterology, vol. 136, No. 5, May 1, 2009, pp. A-625.
Chatterjee, SK et al. Cancer biomarker: Knowing the present and predicting the future. Future Oncology vol. 1(1), pp. 37-50, 2005.
EP Search Report, EP Patent Application No. 15772326.3, dated Nov. 28, 2017.
Kisiel, et al. "Su1340 Detection of Colorectal Cancer and Polyps in Patients with Inflammatory Bowel Disease by Novel Methylated Stool DNA Markers" Gastroenerology, vol. 146, No. 5, May 1, 2014, pp. S-440.
Taylor et al. "109 Discovery of Novel DNA Methylation Markers for the Detection of Colorectal Neopolasia: Selection by Methylome-Wide Analysis" Gastroenterology, vol. 146, No. 5, May 1, 2014, pp. S-30.
Kim et al. Methylation profiles of multiple CpG island loci in extrahepatic cholangiocarcinoma versus those of intrahepatic cholangiocarcinomas. Arch Pathol Lab Med 131:923-930, 2007.
Qiu et al. Hypermethylation of ACP1, BMP4, and TSPYL5 in Hepatocellular Carcinoma and Their Potential Clinical Significance, Digestive Diseases and Sciences, Sep. 19, 2015, vol. 61, No. 1, pp. 149-157.
International Search Report and Written Opinion, International Patent Application No. PCT/US2017/049915, dated Jan. 18, 2018.
Gao et al. "Global Analysis of DNA Methylation in hepatocellular cariconma by a liquid hybridization cpature-based bisulfite sequencing approach" Clinical Epigenetics, vol. 7, No. 86, Aug. 2015.
Barat et al. "Comparative Correlation Structure of Colon Cancer Locus Specific Methylation: Characterisation of Patient Profiles and Potential Markers across 3 Array-Based Datasets" J. Of Cancer, vol. 6, pp. 795-811, Jul. 2015.

(56) References Cited

OTHER PUBLICATIONS

Sloane et al. "Epigenetic inactivation of the candidate tumor suppressor USP44 is a frequent and early event in colorectal neoplasia" Epigenetics, vol. 9, No. 8, pp. 1092-1100, Aug. 2014.
Kisiel Aga Abstracts #469, S-84, May 2013.
Moon, JW et al. Identification of novel hypermethylated genes and demethylating effect of vincristine in colorectal cancer. Journal of Experimental and Clinical Cancer Research. vol. 33, 4, p. 1-10, 2014.
Lowe et al. A computer program for selection of oligonucleotide primers for polymerase chain reactions. Nucleic Acids Research, vol. 18, No. 7, pp. 1757-1761, 1990.
Tan et al. "Variable promoter region CpG island methylation of the putative tumor suppressor gene Connexin 26 in breast cancer" Carcinogenesis. 2002 23(2): 231-236.
Jin et al. "A multicenter, Double-blinded Validation study of methylation biomarkers for progression prediction in Barrett's Esophagus" Cancer Research, May 15, 2009, vol. 69, pp. 4112-4115.
Kaz et al. "DNA methylation profiling in Barrett's esophagus and esophageal adenocarcinoma reveals unique methylation signatures and molecular subclasses" Epigenetics, Dec. 1, 2011, vol. 6, pp. 1403-1412.
Zhai et al. "Genome-wide DNA Methylation Profiling of Cell-Free Serum DNA in Esophageal Adenocarcinoma and Barrett Esophagus" Neoplasia, Jan. 11, 2012, vol. 14, No. 1, pp. 29-33.
International Search Report, International Application No. PCT/US2016/023782, dated Sep. 1, 2016.
Haag S, et al., "Regression of Barrett's esophagus: the role of acid suppression, surgery, and ablative methods." Gastrointest Endosc. Aug. 1999;50(2):229-40.
Supplemental Search Report, EP Patent Application No. 15772326.3, dated Oct. 6, 2017.
Buck et al. "Design Strategies and Performance of Custom DNA Sequencing Primers" Biotechniques, 1999, 27(3): 528-536.
Kisiel et al. "New DNA Methylation Markers for Pancreatic Cancer: Discovery, Tissue Validation, and Pilot Testing in Pancreatic Juice" Clinical Cancer Research, vol. 21, No. 19, May 28, 2015, pp. 4473-4481.
Naumov "Genome-scale analysis of DNA methylation in colorectal cancer using Infinium HumanMethylation450 BeadChips" Epigenetics, 2013, vol. 8, issue 9, pp. 921-934.
Sen-Yo et al. "TWIST1 hypermethylation is observed in pancreatic cancer" Biomedical Reports; 1:33-33, 2013.
Chen "Expression and promoter methylation analysis of ATP-binding cassette genes in pancreatic cancer" Oncology Reports, 2012, 27:265-269.

\* cited by examiner

SEQUENCE LISTING

<160> NUMBER OF SEQ ID NOS: 110

<210> SEQ ID NO 1
<211> LENGTH: 21
<212> TYPE: DNA
<213> ORGANISM: Artificial sequence
<220> FEATURE:
<223> OTHER INFORMATION: Synthetic

<400> SEQUENCE: 1
gggagtgagg gtagggcgtt c                                              21

<210> SEQ ID NO 2
<211> LENGTH: 25
<212> TYPE: DNA
<213> ORGANISM: Artificial sequence
<220> FEATURE:
<223> OTHER INFORMATION: Synthetic

<400> SEQUENCE: 2
ctcgcaaccc cttcgaatta acccg                                          25

<210> SEQ ID NO 3
<211> LENGTH: 25
<212> TYPE: DNA
<213> ORGANISM: Artificial sequence
<220> FEATURE:
<223> OTHER INFORMATION: Synthetic

<400> SEQUENCE: 3
tgcgtaggtg atagggaggg gttac                                          25

<210> SEQ ID NO 4
<211> LENGTH: 25
<212> TYPE: DNA
<213> ORGANISM: Artificial sequence
<220> FEATURE:
<223> OTHER INFORMATION: Synthetic

<400> SEQUENCE: 4
acaaaacaca tcctattaac gcgaa                                          25

<210> SEQ ID NO 5
<211> LENGTH: 19
<212> TYPE: DNA
<213> ORGANISM: Artificial sequence
<220> FEATURE:
<223> OTHER INFORMATION: Synthetic

<400> SEQUENCE: 5
gagtcgcggt ttcgttttc                                                 19

<210> SEQ ID NO 6
<211> LENGTH: 19
<212> TYPE: DNA
<213> ORGANISM: Artificial sequence
<220> FEATURE:
<223> OTHER INFORMATION: Synthetic

<400> SEQUENCE: 6
gacgcgacga ccgaaaaac                                                 19

<210> SEQ ID NO 7
<211> LENGTH: 23
<212> TYPE: DNA
<213> ORGANISM: Artificial sequence

```
<220> FEATURE:
<223> OTHER INFORMATION: Synthetic

<400> SEQUENCE: 7
tgcacacccc gaggcggtcc cgg                                               23

<210> SEQ ID NO 8
<211> LENGTH: 23
<212> TYPE: DNA
<213> ORGANISM: Artificial sequence
<220> FEATURE:
<223> OTHER INFORMATION: Synthetic

<400> SEQUENCE: 8
cgcccccaaa ataaaaaaac gaa                                               23

<210> SEQ ID NO 9

<400> SEQUENCE: 9

000

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
gcgtttaggt tggtcggaga                                                   20

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
cctaaccaac gcactcaacc                                                   20

<210> SEQ ID NO 12
<211> LENGTH: 21
<212> TYPE: DNA
<213> ORGANISM: Artificial sequence
<220> FEATURE:
<223> OTHER INFORMATION: Synthetic

<400> SEQUENCE: 12
cgtagcgtgg cgttttagcg c                                                 21

<210> SEQ ID NO 13
<211> LENGTH: 26
<212> TYPE: DNA
<213> ORGANISM: Artificial sequence
<220> FEATURE:
<223> OTHER INFORMATION: Synthetic

<400> SEQUENCE: 13
tcgaaaaccc cgacgaaacg aaaacg                                            26

<210> SEQ ID NO 14
<211> LENGTH: 25
<212> TYPE: DNA
<213> ORGANISM: Artificial sequence
```

<220> FEATURE:
<223> OTHER INFORMATION: Synthetic

<400> SEQUENCE: 14
gcgtaaggtc gaatatttga gtcga                                              25

<210> SEQ ID NO 15
<211> LENGTH: 25
<212> TYPE: DNA
<213> ORGANISM: Artificial sequence
<220> FEATURE:
<223> OTHER INFORMATION: Synthetic

<400> SEQUENCE: 15
aaaatactac ccaccaacca ccgaa                                              25

<210> SEQ ID NO 16
<211> LENGTH: 19
<212> TYPE: DNA
<213> ORGANISM: Artificial sequence
<220> FEATURE:
<223> OTHER INFORMATION: Synthetic

<400> SEQUENCE: 16
gtcgtcgttc gagagggta                                                     19

<210> SEQ ID NO 17
<211> LENGTH: 22
<212> TYPE: DNA
<213> ORGANISM: Artificial sequence
<220> FEATURE:
<223> OTHER INFORMATION: Synthetic

<400> SEQUENCE: 17
cgaacaaaaa cgaacgaacg aa                                                 22

<210> SEQ ID NO 18
<211> LENGTH: 33
<212> TYPE: DNA
<213> ORGANISM: Artificial sequence
<220> FEATURE:
<223> OTHER INFORMATION: Synthetic

<400> SEQUENCE: 18
tcgattttat ttttgttgtc gttgtagatt cgc                                     33

<210> SEQ ID NO 19
<211> LENGTH: 33
<212> TYPE: DNA
<213> ORGANISM: Artificial sequence
<220> FEATURE:
<223> OTHER INFORMATION: Synthetic

<400> SEQUENCE: 19
gaaaaaacta aaaacgaca aaaaacccg acg                                       33

<210> SEQ ID NO 20
<211> LENGTH: 28
<212> TYPE: DNA
<213> ORGANISM: Artificial sequence
<220> FEATURE:
<223> OTHER INFORMATION: Synthetic

<400> SEQUENCE: 20
ggaacgagtg atagtcggat agttcgtc                                           28

```
<210> SEQ ID NO 21
<211> LENGTH: 18
<212> TYPE: DNA
<213> ORGANISM: Artificial sequence
<220> FEATURE:
<223> OTHER INFORMATION: Synthetic

<400> SEQUENCE: 21
cgcccgaaaa cgaccccg                                                   18

<210> SEQ ID NO 22
<211> LENGTH: 31
<212> TYPE: DNA
<213> ORGANISM: Artificial sequence
<220> FEATURE:
<223> OTHER INFORMATION: Synthetic

<400> SEQUENCE: 22
cggggatgat tttatgtagt cggagtttcg c                                    31

<210> SEQ ID NO 23
<211> LENGTH: 24
<212> TYPE: DNA
<213> ORGANISM: Artificial sequence
<220> FEATURE:
<223> OTHER INFORMATION: Synthetic

<400> SEQUENCE: 23
cccgccgaat actcgatcaa ctcg                                            24

<210> SEQ ID NO 24
<211> LENGTH: 34
<212> TYPE: DNA
<213> ORGANISM: Artificial sequence
<220> FEATURE:
<223> OTHER INFORMATION: Synthetic

<400> SEQUENCE: 24
gcgaataaat aaacgttaat ttgttgtttg tttc                                 34

<210> SEQ ID NO 25
<211> LENGTH: 25
<212> TYPE: DNA
<213> ORGANISM: Artificial sequence
<220> FEATURE:
<223> OTHER INFORMATION: Synthetic

<400> SEQUENCE: 25
ccgaacgcgt ataaataccg cactt                                           25

<210> SEQ ID NO 26
<211> LENGTH: 28
<212> TYPE: DNA
<213> ORGANISM: Artificial sequence
<220> FEATURE:
<223> OTHER INFORMATION: Synthetic

<400> SEQUENCE: 26
cggttttatt tattatgatt cgtagcgg                                        28

<210> SEQ ID NO 27
<211> LENGTH: 24
<212> TYPE: DNA
<213> ORGANISM: Artificial sequence
<220> FEATURE:
<223> OTHER INFORMATION: Synthetic
```

<400> SEQUENCE: 27
cgactaccct aaacaacgca tcgc						24

<210> SEQ ID NO 28
<211> LENGTH: 23
<212> TYPE: DNA
<213> ORGANISM: Artificial sequence
<220> FEATURE:
<223> OTHER INFORMATION: Synthetic

<400> SEQUENCE: 28
cgagttcggt agttgtacgt aga						23

<210> SEQ ID NO 29
<211> LENGTH: 27
<212> TYPE: DNA
<213> ORGANISM: Artificial sequence
<220> FEATURE:
<223> OTHER INFORMATION: Synthetic

<400> SEQUENCE: 29
cgaaatacga acgcgaaatc taaaact						27

<210> SEQ ID NO 30
<211> LENGTH: 19
<212> TYPE: DNA
<213> ORGANISM: Artificial sequence
<220> FEATURE:
<223> OTHER INFORMATION: Synthetic

<400> SEQUENCE: 30
gcgacgtagt cgtcgttgt						19

<210> SEQ ID NO 31
<211> LENGTH: 19
<212> TYPE: DNA
<213> ORGANISM: Artificial sequence
<220> FEATURE:
<223> OTHER INFORMATION: Synthetic

<400> SEQUENCE: 31
ccaacgcgaa aaaacgcg						19

<210> SEQ ID NO 32
<211> LENGTH: 19
<212> TYPE: DNA
<213> ORGANISM: Artificial sequence
<220> FEATURE:
<223> OTHER INFORMATION: Synthetic

<400> SEQUENCE: 32
gaggcggacg tcgcggtac						19

<210> SEQ ID NO 33
<211> LENGTH: 25
<212> TYPE: DNA
<213> ORGANISM: Artificial sequence
<220> FEATURE:
<223> OTHER INFORMATION: Synthetic

<400> SEQUENCE: 33
cgccacgacg cgaatcttaa ctacg						25

```
<210> SEQ ID NO 34
<211> LENGTH: 22
<212> TYPE: DNA
<213> ORGANISM: Artificial sequence
<220> FEATURE:
<223> OTHER INFORMATION: Synthetic

<400> SEQUENCE: 34
ggatcgaggg agtaggagtc gc                                              22

<210> SEQ ID NO 35
<211> LENGTH: 22
<212> TYPE: DNA
<213> ORGANISM: Artificial sequence
<220> FEATURE:
<223> OTHER INFORMATION: Synthetic

<400> SEQUENCE: 35
cgaaaccgaa cctaacgcga cg                                              22

<210> SEQ ID NO 36
<211> LENGTH: 24
<212> TYPE: DNA
<213> ORGANISM: Artificial sequence
<220> FEATURE:
<223> OTHER INFORMATION: Synthetic

<400> SEQUENCE: 36 agtttttcg cgcgtttttt ttgc                                             24

<210> SEQ ID NO 37
<211> LENGTH: 21
<212> TYPE: DNA
<213> ORGANISM: Artificial sequence
<220> FEATURE:
<223> OTHER INFORMATION: Synthetic

<400> SEQUENCE: 37
gccgaatctc cgccttacac g                                               21

<210> SEQ ID NO 38
<211> LENGTH: 23
<212> TYPE: DNA
<213> ORGANISM: Artificial sequence
<220> FEATURE:
<223> OTHER INFORMATION: Synthetic

<400> SEQUENCE: 38
gtttaatttt cggtttcgtc gtc                                             23

<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39
cgccgaggcg gtttttttgcg                                                20

<210> SEQ ID NO 40
<211> LENGTH: 18
<212> TYPE: DNA
<213> ORGANISM: Artificial sequence
<220> FEATURE:
<223> OTHER INFORMATION: Synthetic
```

<400> SEQUENCE: 40
cgctacgaaa cactccga                                                   18

<210> SEQ ID NO 41
<211> LENGTH: 21
<212> TYPE: DNA
<213> ORGANISM: Artificial sequence
<220> FEATURE:
<223> OTHER INFORMATION: Synthetic

<400> SEQUENCE: 41
cggttttcgt tcgtttttc g                                                21

<210> SEQ ID NO 42
<211> LENGTH: 21
<212> TYPE: DNA
<213> ORGANISM: Artificial sequence
<220> FEATURE:
<223> OTHER INFORMATION: Synthetic

<400> SEQUENCE: 42
ccacggacgg ttcgtttatc g                                               21

<210> SEQ ID NO 43
<211> LENGTH: 18
<212> TYPE: DNA
<213> ORGANISM: Artificial sequence
<220> FEATURE:
<223> OTHER INFORMATION: Synthetic

<400> SEQUENCE: 43
ccgccttcta cgcgacta                                                   18

<210> SEQ ID NO 44
<211> LENGTH: 34
<212> TYPE: DNA
<213> ORGANISM: Artificial sequence
<220> FEATURE:
<223> OTHER INFORMATION: Synthetic

<400> SEQUENCE: 44
gcgaataaat aaacgttaat ttgttgtttg tttc                                 34

<210> SEQ ID NO 45
<211> LENGTH: 21
<212> TYPE: DNA
<213> ORGANISM: Artificial sequence
<220> FEATURE:
<223> OTHER INFORMATION: Synthetic

<400> SEQUENCE: 45
ccacggacgc gcacttcctt a                                               21

<210> SEQ ID NO 46
<211> LENGTH: 25
<212> TYPE: DNA
<213> ORGANISM: Artificial sequence
<220> FEATURE:
<223> OTHER INFORMATION: Synthetic

<400> SEQUENCE: 46
ccgaacgcgt ataaataccg cactt                                           25

```
<210> SEQ ID NO 47
<211> LENGTH: 23
<212> TYPE: DNA
<213> ORGANISM: Artificial sequence
<220> FEATURE:
<223> OTHER INFORMATION: Synthetic

<400> SEQUENCE: 47
cgagttcggt agttgtacgt aga                                              23

<210> SEQ ID NO 48
<211> LENGTH: 20
<212> TYPE: DNA
<213> ORGANISM: Artificial sequence
<220> FEATURE:
<223> OTHER INFORMATION: Synthetic

<400> SEQUENCE: 48
cgccgaggtc gtcgataccg                                                  20

<210> SEQ ID NO 49
<211> LENGTH: 27
<212> TYPE: DNA
<213> ORGANISM: Artificial sequence
<220> FEATURE:
<223> OTHER INFORMATION: Synthetic

<400> SEQUENCE: 49
cgaaatacga acgcgaaatc taaaact                                          27

<210> SEQ ID NO 50
<211> LENGTH: 19
<212> TYPE: DNA
<213> ORGANISM: Artificial sequence
<220> FEATURE:
<223> OTHER INFORMATION: Synthetic

<400> SEQUENCE: 50
gcgacgtagt cgtcgttgt                                                   19

<210> SEQ ID NO 51
<211> LENGTH: 21
<212> TYPE: DNA
<213> ORGANISM: Artificial sequence
<220> FEATURE:
<223> OTHER INFORMATION: Synthetic

<400> SEQUENCE: 51
ccacggacgg aaaacgcgaa a                                                21

<210> SEQ ID NO 52
<211> LENGTH: 19
<212> TYPE: DNA
<213> ORGANISM: Artificial sequence
<220> FEATURE:
<223> OTHER INFORMATION: Synthetic

<400> SEQUENCE: 52
ccaacgcgaa aaaacgcg                                                    19

<210> SEQ ID NO 53

<400> SEQUENCE: 53

000
```

```
<210> SEQ ID NO 54
<211> LENGTH: 19
<212> TYPE: DNA
<213> ORGANISM: Artificial sequence
<220> FEATURE:
<223> OTHER INFORMATION: Synthetic

<400> SEQUENCE: 54
tcggagtcga gtttagcgc                                               19

<210> SEQ ID NO 55
<211> LENGTH: 21
<212> TYPE: DNA
<213> ORGANISM: Artificial sequence
<220> FEATURE:
<223> OTHER INFORMATION: Synthetic

<400> SEQUENCE: 55
ccacggacgc ggcgttcgcg a                                            21

<210> SEQ ID NO 56
<211> LENGTH: 24
<212> TYPE: DNA
<213> ORGANISM: Artificial sequence
<220> FEATURE:
<223> OTHER INFORMATION: Synthetic

<400> SEQUENCE: 56
cgaaatcgaa aaacaaaaa ccgc                                          24

<210> SEQ ID NO 57
<211> LENGTH: 23
<212> TYPE: DNA
<213> ORGANISM: Artificial sequence
<220> FEATURE:
<223> OTHER INFORMATION: Synthetic

<400> SEQUENCE: 57
cgagttcggt agttgtacgt aga                                          23

<210> SEQ ID NO 58
<211> LENGTH: 20
<212> TYPE: DNA
<213> ORGANISM: Artificial sequence
<220> FEATURE:
<223> OTHER INFORMATION: Synthetic

<400> SEQUENCE: 58
cgccgaggtc gtcgataccg                                              20

<210> SEQ ID NO 59
<211> LENGTH: 20
<212> TYPE: DNA
<213> ORGANISM: Artificial sequence
<220> FEATURE:
<223> OTHER INFORMATION: Synthetic

<400> SEQUENCE: 59
cgccgaggtc gtcgataccg                                              20

<210> SEQ ID NO 60
<211> LENGTH: 19
<212> TYPE: DNA
<213> ORGANISM: Artificial sequence
<220> FEATURE:
<223> OTHER INFORMATION: Synthetic
```

```
<400> SEQUENCE: 60
gtcgtcgttc gagagggta                                              19

<210> SEQ ID NO 61
<211> LENGTH: 21
<212> TYPE: DNA
<213> ORGANISM: Artificial sequence
<220> FEATURE:
<223> OTHER INFORMATION: Synthetic

<400> SEQUENCE: 61
ccacggacga tcggtttcgt t                                           21

<210> SEQ ID NO 62
<211> LENGTH: 22
<212> TYPE: DNA
<213> ORGANISM: Artificial sequence
<220> FEATURE:
<223> OTHER INFORMATION: Synthetic

<400> SEQUENCE: 62
cgaacaaaaa cgaacgaacg aa                                          22

<210> SEQ ID NO 63
<211> LENGTH: 20
<212> TYPE: DNA
<213> ORGANISM: Artificial sequence
<220> FEATURE:
<223> OTHER INFORMATION: Synthetic

<400> SEQUENCE: 63
gcgtttaggt tggtcggaga                                             20

<210> SEQ ID NO 64
<211> LENGTH: 20
<212> TYPE: DNA
<213> ORGANISM: Artificial sequence
<220> FEATURE:
<223> OTHER INFORMATION: Synthetic

<400> SEQUENCE: 64
cgccgaggct acgaaccgaa                                             20

<210> SEQ ID NO 65
<211> LENGTH: 20
<212> TYPE: DNA
<213> ORGANISM: Artificial sequence
<220> FEATURE:
<223> OTHER INFORMATION: Synthetic

<400> SEQUENCE: 65
cctaaccaac gcactcaacc                                             20

<210> SEQ ID NO 66
<211> LENGTH: 21
<212> TYPE: DNA
<213> ORGANISM: Artificial sequence
<220> FEATURE:
<223> OTHER INFORMATION: Synthetic

<400> SEQUENCE: 66
ttagcgacgt agtcgtcgtt g                                           21
```

```
<210> SEQ ID NO 67
<211> LENGTH: 21
<212> TYPE: DNA
<213> ORGANISM: Artificial sequence
<220> FEATURE:
<223> OTHER INFORMATION: Synthetic

<400> SEQUENCE: 67
ccacggacgc gaaaacgcga a                                              21

<210> SEQ ID NO 68
<211> LENGTH: 19
<212> TYPE: DNA
<213> ORGANISM: Artificial sequence
<220> FEATURE:
<223> OTHER INFORMATION: Synthetic

<400> SEQUENCE: 68
cccaacgcga aaaaaacgc                                                 19

<210> SEQ ID NO 69
<211> LENGTH: 21
<212> TYPE: DNA
<213> ORGANISM: Artificial sequence
<220> FEATURE:
<223> OTHER INFORMATION: Synthetic

<400> SEQUENCE: 69
gtatagcgcg atttcgtagc g                                              21

<210> SEQ ID NO 70
<211> LENGTH: 20
<212> TYPE: DNA
<213> ORGANISM: Artificial sequence
<220> FEATURE:
<223> OTHER INFORMATION: Synthetic

<400> SEQUENCE: 70
cgccgaggcg aacatcctcc                                                20

<210> SEQ ID NO 71
<211> LENGTH: 21
<212> TYPE: DNA
<213> ORGANISM: Artificial sequence
<220> FEATURE:
<223> OTHER INFORMATION: Synthetic

<400> SEQUENCE: 71
aattacctac gctatccgcc c                                              21

<210> SEQ ID NO 72
<211> LENGTH: 22
<212> TYPE: DNA
<213> ORGANISM: Artificial sequence
<220> FEATURE:
<223> OTHER INFORMATION: Synthetic

<400> SEQUENCE: 72
cgtcgcgttt ttcggttata cg                                             22

<210> SEQ ID NO 73
<211> LENGTH: 21
<212> TYPE: DNA
<213> ORGANISM: Artificial sequence
<220> FEATURE:
<223> OTHER INFORMATION: Synthetic
```

<400> SEQUENCE: 73
ccacggacgg caccgtaaaa c                                              21

<210> SEQ ID NO 74
<211> LENGTH: 21
<212> TYPE: DNA
<213> ORGANISM: Artificial sequence
<220> FEATURE:
<223> OTHER INFORMATION: Synthetic

<400> SEQUENCE: 74
cgcgaaaact aaaaaaccgc g                                              21

<210> SEQ ID NO 75
<211> LENGTH: 27
<212> TYPE: DNA
<213> ORGANISM: Artificial sequence
<220> FEATURE:
<223> OTHER INFORMATION: Synthetic

<400> SEQUENCE: 75
aaacgttaat ttgttgtttg tttcgtt                                        27

<210> SEQ ID NO 76
<211> LENGTH: 24
<212> TYPE: DNA
<213> ORGANISM: Artificial sequence
<220> FEATURE:
<223> OTHER INFORMATION: Synthetic

<400> SEQUENCE: 76
actttccgaa cgcgtataaa tacc                                           24

<210> SEQ ID NO 77
<211> LENGTH: 35
<212> TYPE: DNA
<213> ORGANISM: Artificial sequence
<220> FEATURE:
<223> OTHER INFORMATION: Synthetic

<400> SEQUENCE: 77
gcgaataaat aaacgttaat ttgttgtttg tttcg                               35

<210> SEQ ID NO 78
<211> LENGTH: 23
<212> TYPE: DNA
<213> ORGANISM: Artificial sequence
<220> FEATURE:
<223> OTHER INFORMATION: Synthetic

<400> SEQUENCE: 78
gttgcgaggt taggttgtaa tcg                                            23

<210> SEQ ID NO 79
<211> LENGTH: 20
<212> TYPE: DNA
<213> ORGANISM: Artificial sequence
<220> FEATURE:
<223> OTHER INFORMATION: Synthetic

<400> SEQUENCE: 79
cgccgaggcg tccatttaac                                                20

```
<210> SEQ ID NO 80
<211> LENGTH: 22
<212> TYPE: DNA
<213> ORGANISM: Artificial sequence
<220> FEATURE:
<223> OTHER INFORMATION: Synthetic

<400> SEQUENCE: 80
cgccgcttac cttaataatc cc                                              22

<210> SEQ ID NO 81
<211> LENGTH: 19
<212> TYPE: DNA
<213> ORGANISM: Artificial sequence
<220> FEATURE:
<223> OTHER INFORMATION: Synthetic

<400> SEQUENCE: 81
gagtcgcggt ttcgttttc                                                  19

<210> SEQ ID NO 82
<211> LENGTH: 20
<212> TYPE: DNA
<213> ORGANISM: Artificial sequence
<220> FEATURE:
<223> OTHER INFORMATION: Synthetic

<400> SEQUENCE: 82
cgccgaggcg cgttcgtttt                                                 20

<210> SEQ ID NO 83
<211> LENGTH: 19
<212> TYPE: DNA
<213> ORGANISM: Artificial sequence
<220> FEATURE:
<223> OTHER INFORMATION: Synthetic

<400> SEQUENCE: 83
gacgcgacga ccgaaaaac                                                  19

<210> SEQ ID NO 84
<211> LENGTH: 21
<212> TYPE: DNA
<213> ORGANISM: Artificial sequence
<220> FEATURE:
<223> OTHER INFORMATION: Synthetic

<400> SEQUENCE: 84
cggttttcgt tcgtttttc g                                                21

<210> SEQ ID NO 85
<211> LENGTH: 21
<212> TYPE: DNA
<213> ORGANISM: Artificial sequence
<220> FEATURE:
<223> OTHER INFORMATION: Synthetic

<400> SEQUENCE: 85
ccacggacgg ttcgtttatc g                                               21

<210> SEQ ID NO 86
<211> LENGTH: 18
<212> TYPE: DNA
<213> ORGANISM: Artificial sequence
<220> FEATURE:
<223> OTHER INFORMATION: Synthetic
```

```
<400> SEQUENCE: 86
ccgccttcta cgcgacta                                                 18

<210> SEQ ID NO 87
<211> LENGTH: 23
<212> TYPE: DNA
<213> ORGANISM: Artificial sequence
<220> FEATURE:
<223> OTHER INFORMATION: Synthetic

<400> SEQUENCE: 87
gtttaatttt cggtttcgtc gtc                                           23

<210> SEQ ID NO 88
<211> LENGTH: 20
<212> TYPE: DNA
<213> ORGANISM: Artificial sequence
<220> FEATURE:
<223> OTHER INFORMATION: Synthetic

<400> SEQUENCE: 88
cgccgaggcg gttttttgcg                                               20

<210> SEQ ID NO 89
<211> LENGTH: 18
<212> TYPE: DNA
<213> ORGANISM: Artificial sequence
<220> FEATURE:
<223> OTHER INFORMATION: Synthetic

<400> SEQUENCE: 89
cgctacgaaa cactccga                                                 18

<210> SEQ ID NO 90
<211> LENGTH: 19
<212> TYPE: DNA
<213> ORGANISM: Artificial sequence
<220> FEATURE:
<223> OTHER INFORMATION: Synthetic

<400> SEQUENCE: 90
gcgtttaggt tggtcggag                                                19

<210> SEQ ID NO 91
<211> LENGTH: 20
<212> TYPE: DNA
<213> ORGANISM: Artificial sequence
<220> FEATURE:
<223> OTHER INFORMATION: Synthetic

<400> SEQUENCE: 91
cgccgaggcc gaaaaactac                                               20

<210> SEQ ID NO 92
<211> LENGTH: 19
<212> TYPE: DNA
<213> ORGANISM: Artificial sequence
<220> FEATURE:
<223> OTHER INFORMATION: Synthetic

<400> SEQUENCE: 92
acgcactcaa cctacgaac                                                19
```

```
<210> SEQ ID NO 93
<211> LENGTH: 19
<212> TYPE: DNA
<213> ORGANISM: Artificial sequence
<220> FEATURE:
<223> OTHER INFORMATION: Synthetic

<400> SEQUENCE: 93
gcgacgtagt cgtcgttgt                                               19

<210> SEQ ID NO 94
<211> LENGTH: 21
<212> TYPE: DNA
<213> ORGANISM: Artificial sequence
<220> FEATURE:
<223> OTHER INFORMATION: Synthetic

<400> SEQUENCE: 94
ccacggacgg aaaacgcgaa a                                            21

<210> SEQ ID NO 95
<211> LENGTH: 19
<212> TYPE: DNA
<213> ORGANISM: Artificial sequence
<220> FEATURE:
<223> OTHER INFORMATION: Synthetic

<400> SEQUENCE: 95
ccaacgcgaa aaaacgcg                                                19

<210> SEQ ID NO 96
<211> LENGTH: 35
<212> TYPE: DNA
<213> ORGANISM: Artificial sequence
<220> FEATURE:
<223> OTHER INFORMATION: Synthetic

<400> SEQUENCE: 96
gcgaataaat aaacgttaat ttgttgtttg tttcg                             35

<210> SEQ ID NO 97
<211> LENGTH: 21
<212> TYPE: DNA
<213> ORGANISM: Artificial sequence
<220> FEATURE:
<223> OTHER INFORMATION: Synthetic

<400> SEQUENCE: 97
ccacggacgc gcacttcctt a                                            21

<210> SEQ ID NO 98
<211> LENGTH: 24
<212> TYPE: DNA
<213> ORGANISM: Artificial sequence
<220> FEATURE:
<223> OTHER INFORMATION: Synthetic

<400> SEQUENCE: 98
actttccgaa cgcgtataaa tacc                                         24

<210> SEQ ID NO 99
<211> LENGTH: 36
<212> TYPE: DNA
<213> ORGANISM: Artificial sequence
<220> FEATURE:
<223> OTHER INFORMATION: Synthetic
```

```
<400> SEQUENCE: 99
gatcgaggga gcaggagccg cggctgacgg gtcgcg                               36

<210> SEQ ID NO 100
<211> LENGTH: 35
<212> TYPE: DNA
<213> ORGANISM: Artificial sequence
<220> FEATURE:
<223> OTHER INFORMATION: Synthetic

<400> SEQUENCE: 100
cggtgccgag agctgccaga gagttggatt ctgcg                                35

<210> SEQ ID NO 101
<211> LENGTH: 24
<212> TYPE: DNA
<213> ORGANISM: Artificial sequence
<220> FEATURE:
<223> OTHER INFORMATION: Synthetic

<400> SEQUENCE: 101
gcgagcgggc aagggcgggc gagc                                            24

<210> SEQ ID NO 102
<211> LENGTH: 28
<212> TYPE: DNA
<213> ORGANISM: Artificial sequence
<220> FEATURE:
<223> OTHER INFORMATION: Synthetic

<400> SEQUENCE: 102
acctgcgggc cgaagggctg ctctccgg                                        28

<210> SEQ ID NO 103
<211> LENGTH: 29
<212> TYPE: DNA
<213> ORGANISM: Artificial sequence
<220> FEATURE:
<223> OTHER INFORMATION: Synthetic

<400> SEQUENCE: 103
aggagacgcg ggagcgcggg gtaggtagc                                       29

<210> SEQ ID NO 104
<211> LENGTH: 34
<212> TYPE: DNA
<213> ORGANISM: Artificial sequence
<220> FEATURE:
<223> OTHER INFORMATION: Synthetic

<400> SEQUENCE: 104
ggcatcctcc cggtgatgga agcagccgcc gccg                                 34

<210> SEQ ID NO 105
<211> LENGTH: 34
<212> TYPE: DNA
<213> ORGANISM: Artificial sequence
<220> FEATURE:
<223> OTHER INFORMATION: Synthetic

<400> SEQUENCE: 105
ggaaggcgcg gcgctcggtc agcactgaca gcag                                 34
```

```
<210> SEQ ID NO 106
<211> LENGTH: 39
<212> TYPE: DNA
<213> ORGANISM: Artificial sequence
<220> FEATURE:
<223> OTHER INFORMATION: Synthetic

<400> SEQUENCE: 106
tcgccgagct ctccccaaac ttcctgcatg ctgaacttt                              39

<210> SEQ ID NO 107
<211> LENGTH: 31
<212> TYPE: DNA
<213> ORGANISM: Artificial sequence
<220> FEATURE:
<223> OTHER INFORMATION: Synthetic

<400> SEQUENCE: 107
ccgtccattt ggccaagtct gcagccgagc c                                     31

<210> SEQ ID NO 108
<211> LENGTH: 33
<212> TYPE: DNA
<213> ORGANISM: Artificial sequence
<220> FEATURE:
<223> OTHER INFORMATION: Synthetic

<400> SEQUENCE: 108
ctgcgtccgt ccgtcggccg ggcagtctgt cca                                   33

<210> SEQ ID NO 109
<211> LENGTH: 48
<212> TYPE: DNA
<213> ORGANISM: Artificial sequence
<220> FEATURE:
<223> OTHER INFORMATION: Synthetic

<400> SEQUENCE: 109
tccctcgcgc gtggcttccg ccttctgcgc ggctggggtg cccggtgg                   48

<210> SEQ ID NO 110
<211> LENGTH: 26
<212> TYPE: DNA
<213> ORGANISM: Artificial sequence
<220> FEATURE:
<223> OTHER INFORMATION: Synthetic

<400> SEQUENCE: 110
gcgggacact ccgaaggcgc aaggag                                           26
```

DETECTING COLORECTAL NEOPLASM

CROSS-REFERENCE TO RELATED APPLICATIONS

This application is a continuation of U.S. patent application Ser. No. 15/301,227, filed Sep. 30, 2016, which is a U.S. National Entry of International Patent Application No. PCT/US2015/022749, filed Mar. 26, 2015, which claims priority to U.S. Provisional Patent Application No. 61/977,954, filed Apr. 10, 2014, and U.S. Provisional Patent Application No. 61/972,942 filed Mar. 31, 2014, the contents of which are incorporated by reference in their entireties.

FIELD OF INVENTION

Provided herein is technology relating to detecting neoplasia and particularly, but not exclusively, to methods, compositions, and related uses for detecting premalignant and malignant neoplasms such as colorectal cancer.

BACKGROUND

Colorectal cancer remains the $2^{nd}$ most common cancer in U.S. men and women combined (Siegel R, et al., C A Cancer J Clin 2013; 63:11-30). The underlying biology of progression from precursor lesion to cancer lends itself favorably to screening (Vogelstein B, et al., Science 2013; 339:1546-58). Evidence supports and guidelines endorse any of several tests and strategies (Levin B, et al., Gastroenterology 2008; 134:1570-95; Rex D K, et al., Am J Gastroenterol 2009; 104:739-50; Karl J, et al., Clin Gastroenterol Hepatol 2008; 6:1122-8). From a societal perspective, screening is considered cost-effective (Karl J, et al., Clin Gastroenterol Hepatol 2008; 6:1122-8; Heitman S J, et al., PLoS Med 2010; 7:e1000370; Parekh M, et al., Aliment Pharmacol Ther 2008; 27:697-712; Sharaf R N, et al., Am J Gastroenterol 2013; 108:120-32).

Colorectal cancer arises from accumulated genetic and epigenetic alterations, providing a basis for analysis of stool for tumor-specific changes (Berger B M, et al., Pathology 2012; 44:80-8). Previous large-scale studies of early generation stool-based DNA tests in the screening setting demonstrated only fair sensitivity for colorectal cancer and low sensitivity for advanced adenomas (Ahlquist D A, et al., Ann Intern Med 2008; 149:441-50, W81; Imperiale T F, et al., N Engl J Med 2004; 351:2704-14). Important advances have since been incorporated, including a stabilizing buffer (Boynton K A, et al., Clin Chem 2003; 49:1058-65; Zou H, et al., Cancer Epidemiol Biomarkers Prey 2006; 15:1115-9), more discriminant markers (Ahlquist D A, et al., Gastroenterology 2012; 142:248-56; Bardan E, et al., Israel journal of medical sciences 1997; 33:777-80), platforms with higher analytic sensitivity (Ahlquist D A, et al., Gastroenterology 2012; 142:248-56; Aronchick C A, et al., Gastrointestinal endoscopy 2000; 52:346-52), result determination using a logistic regression analysis rather than individual marker values, and automation.

Although screening reduces colorectal cancer mortality (Mandel J S, et al., N Engl J Med. 1993, 328:1365-71; Hardcastle J D, et al., Lancet. 1996, 348:1472-7; Kronborg O, et al., Scand J Gastroenterol. 2004, 39:846-51; Winawer S J, et al., J Natl Cancer Inst. 1993, 85:1311-8; Singh H, et al., JAMA. 2006, 295:2366-73), observed reductions have been modest (Singh H, et al., JAMA. 2006; 295, 2366-73; Heresbach D, et al., Eur J Gastroenterol Hepatol. 2006, 18:427-33) and more than one half of adults in the United States have not received screening (Meissner H I, Cancer Epidemiol Biomarkers Prev. 2006, 15:389-94).

An emerging approach to cancer screening involves the assay of tumor-specific DNA alterations in bodily samples from cancer patients, such as stool, serum, and urine (Osborn N K, Ahlquist D A. Gastroenterology 2005; 128:192-206; Ahlquist D A, et al., Gastroenterology 2000; 119:1219-27; Ahlquist D A, et al., Gastroenterology 2002; 122:Suppl A40; Chen W D, et al., J Natl Cancer Inst 2005; 97:1124-32; Zou H, et al., Cancer Epidemiol Biomarkers Prev 2006; 15:1115-9; Zou H Z, Clin Cancer Res 2002; 8:188-91; Hoque M O, J Clin Oncol 2005; 23:6569-75; Belinsky S A, et al., Cancer Res 2006; 66:3338-44; Itzkowitz S H, et al., Clin Gastroenterol Hepatol 2007; 5:111-7' Kann L, et al., Clin Chem 2006; 52:2299-302). It is important to select markers with high accuracy if efficiency and effectiveness are to be achieved in a cancer screening application. Due to the molecular heterogeneity of colorectal neoplasia, high detection rates often require a panel of markers.

Several methylated genes have been detected in the stool and serum/plasma samples from colorectal cancer patients (Ahlquist D A, Gastroenterology 2002; 122:Suppl A40; Chen W D, et al., J Natl Cancer Inst 2005; 97:1124-32; Zou H Z, et al., Clin Cancer Res 2002; 8:188-91; Itzkowitz S H, et al., Clin Gastroenterol Hepatol 2007; 5:111-7; Petko Z, et al., Clin Cancer Res 2005; 11:1203-9; Muller H M, et al., Lancet 2004; 363:1283-5; Leung W K, et al., Clin Chem 2004; 50:2179-82; Ebert M P, et al., Gastroenterology 2006; 131:1418-30; Grady W M, et al., Cancer Res 2001; 61:900-2). Whereas some methylated genes have been found in a majority of colorectal cancers, the yield of bodily fluid-based assays remains suboptimal (Ahlquist D A, et al., Gastroenterology 2002; 122:Suppl A40; Chen W D, et al., J Natl Cancer Inst 2005; 97:1124-32; Zou H, et al., Cancer Epidemiol Biomarkers Prey 2006; 15:1115-9; Zou H Z, Clin Cancer Res 2002; 8:188-91; Belinsky S A, et al., Cancer Res 2006; 66:3338-44; Itzkowitz S H, et al., Clin Gastroenterol Hepatol 2007; 5:111-7; Kann L, et al., Clin Chem 2006; 52:2299-302; Petko Z, et al., Clin Cancer Res 2005; 11:1203-9; Muller H M, et al., Lancet 2004; 363:1283-5; Leung W K, et al., Clin Chem 2004; 50:2179-82; Ebert M P, et al., Gastroenterology 2006; 131:1418-30; Grady W M, et al., Cancer Res 2001; 61:900-2).

More accurate, user-friendly, and widely distributable tools to improve screening effectiveness, acceptability, and access are needed.

SUMMARY

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) Nat Rev Genet 11: 191-203). Furthermore, in cancers such as sporadic colon cancer, methylation markers offer excellent specificity and are more broadly informative and sensitive than are individual DNA mutations (Zou et al (2007) Cancer Epidemiol Biomarkers Prey 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) PLoS Genet 5: e1000438). Further, methylation levels were distributed bi-modally between highly methylated and unmethylated sequences, further supporting the binary switch-like pattern of DNA methyltransferase activity (Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) Nature 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) Nature 454: 766-70).

Methylated genes have been detected in the blood and stool of patients with colorectal cancer and proposed as candidate screening markers (Ahlquist D A, et al., Gastroenterology 2002; 122:Suppl A40; Chen W D, et al., J Natl Cancer Inst 2005; 97:1124-32; Zou H Z, Clin Cancer Res 2002; 8:188-91; Itzkowitz S H, et al., Clin Gastroenterol Hepatol 2007; 5:111-7; Kann L, et al., Clin Chem 2006; 52:2299-302; Petko Z, et al., Clin Cancer Res 2005; 11:1203-9; Muller H M, et al., Lancet 2004; 363:1283-5; Leung W K, et al., Clin Chem 2004; 50:2179-82; Ebert M P, et al., Gastroenterology 2006; 131:1418-30; Grady W M, et al., Cancer Res 2001; 61:900-2).

Zou and colleagues, for example, evaluated genes frequently methylated in colorectal neoplasia to identify the most discriminant ones (Zou, et al., 2007 Cancer Epidemiol Biomarkers Prev. 16(12):2686-2696). Four genes specifically methylated in colorectal cancer (bone morphogenetic protein 3 (BMP3), EYA2, aristaless-like homeobox-4 (ALX4), and vimentin) were selected from 41 candidate genes and evaluated on 74 cancers, 62 adenomas, and 70 normal epithelia. Methylation status was analyzed qualitatively and quantitatively and confirmed by bisulfite genomic sequencing. Effect of methylation on gene expression was evaluated in five colon cancer cell lines. K-ras and BRAF mutations were detected by sequencing. Methylation of BMP3, EYA2, ALX4, or vimentin was detected respectively in 66%, 66%, 68%, and 72% of cancers; 74%, 48%, 89%, and 84% of adenomas; and 7%, 5%, 11%, and 11% of normal epithelia (P<0.01, cancer or adenoma versus normal). It was concluded that BMP3, EYA2, ALX4, and vimentin genes are methylated in most colorectal neoplasms but rarely in normal epithelia.

Cancer screening is in need of a marker or marker panel for colorectal cancer that is broadly informative and exhibits high specificity for colorectal cancer at the tissue level when interrogated in samples taken from a subject (e.g., a stool sample; a colorectal tissue sample).

Accordingly, provided herein is technology for colorectal cancer screening markers that provide a high signal-to-noise ratio and a low background level when detected from samples taken from a subject (e.g., a stool sample; a colorectal tissue sample; serum sample; blood or blood product).

In experiments conducted during the course of developing embodiments for the present invention, markers were identified in a case-control studies by comparing the methylation state of DNA markers from colorectal tissue of subjects with colorectal neoplasia, adenoma, and/or sessile serrated polyps (SSP) to the methylation state of the same DNA markers from control subjects (e.g., normal tissue such as normal colon) (see, Examples 1-2, Tables 1-5). For example, markers and/or panels of markers (e.g., a chromosomal region having an annotation selected from FLI1, OPLAH, DTX1, MATK, SFMBT2 region 2, KCNK12, VAV3 region 1, SFMBT2 region 3, PPP2R5C, CHST2 region 2, PKIA, PDGFD, ELOVL2, CHST2 region 1, SFMBT2 region 1, QKI, VAV3 region 2, and SLC8A3) were identified in a case-control study by comparing the methylation state of DNA markers (e.g., from colorectal tissue of subjects with colorectal neoplasia and/or adenoma) to the methylation state of the same DNA markers from control subjects (e.g., normal tissue such as normal colon) (see, Example 1 and Table 1).

Markers and/or panels of markers (e.g., a chromosomal region having an annotation selected from BMP3, NDRG4, PDGFG, CHST2, and SFMBT2) were identified in case-control studies by comparing the methylation state of DNA markers from colorectal tissue of subjects having inflammatory bowel disease and colorectal cancer to the methylation state of the same DNA markers from control subjects (e.g., normal tissue such as normal colon) (see, Example 1 and Table 2).

In addition, 185, 244, and 111 DNA methylation markers specific for colorectal cancers, large adenomas, and sessile serrated polyps, respectively, were identified (see, Example 2 and Tables 3, 4 and 5). Along with the colorectal cancer cases, large adenoma cases, and sessile serrated polyps cases, normal colonic mucosa, and normal white blood cell DNA was sequenced.

Additional experiments conducted during the course of developing embodiments for the present invention demonstrated NDRG4, BMP3, OPLAH, FLI1, PDGFD, CHST_7889, SFMBT2_895, SFMBT2_896, SFMBT2_897, CHST2_7890, VAV3, and DTX1 as effective markers for detecting colorectal cancer within stool samples (see, Example 3 and Tables 6 and 7).

As described herein, the technology provides a number of methylated DNA markers and subsets thereof (e.g., sets of 2, 3, 4, 5, 6, 7, 8, 9, 10, 11, 12 or more markers) with high discrimination for colorectal neoplasia (e.g., colorectal cancer, adenoma, SSP). Experiments applied a selection filter to candidate markers to identify markers that provide a high signal to noise ratio and a low background level to provide high specificity, e.g., when assaying distant media (e.g., stool, blood, urine, metastatic tissue, etc.) for purposes of colorectal cancer screening or diagnosis. As such, the technology provides for specific markers and marker combinations for purposes of colorectal cancer screening or diagnosis.

In some embodiments, the technology is related to assessing the presence of and methylation state of one or more of the markers identified herein in a biological sample. These markers comprise one or more differentially methylated regions (DMR) as discussed herein, e.g., as provided in Tables 1-6. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) Mol. Cell. Biol. 14: 7421-7427) and another example involves methylation-sensitive arbitrarily primed PCR (Gonzalgo et al. (1997) Cancer Res. 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) Nucl. Acids Res. 18: 687). In addition, other techniques have been reported that utilize bisulfite treatment of DNA as a starting point for methylation analysis. These include methylation-specific PCR (MSP) (Herman et al. (1992) Proc. Natl. Acad. Sci. USA 93: 9821-9826) and restriction enzyme digestion of PCR products amplified from bisulfite-converted DNA (Sadri and Hornsby (1996) Nucl. Acids Res. 24: 5058-5059; and Xiong and Laird (1997) Nucl. Acids Res. 25: 2532-2534). PCR techniques have been developed for detection of gene mutations (Kuppuswamy et al. (1991) Proc. Natl. Acad. Sci. USA 88: 1143-1147) and quantification of allelic-specific expression (Szabo and Mann (1995) Genes Dev. 9: 3097-3108; and Singer-Sam et al. (1992) PCR Methods Appl. 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

According to another aspect of the present invention, neoplasia of a biological sample is indicated when a methylation ratio of one or more DNA methylation markers relative to a level of bisulfite-treated DNA copy number of a reference gene is different, wherein the one or more DNA methylation markers comprises a base in a differentially methylated region (DMR) as provided herein. The methylation ratio includes the ratio of the methylation level of the DNA methylation marker and the level of a region in a reference gene determined by the same means used for the determination of the methylation level of the biomarker. Usually, the methylation ratio is represented by the ratio of the methylation level of the DNA methylation marker and the level of a region in a reference gene determined by the same means used for the determination of the methylation level of the DNA methylation marker.

In some embodiments, the methylation ratio is the ratio of the methylation level of a DNA methylation marker and the level of a region of a reference gene, both of which are quantitatively measured using real-time polymerase chain reaction (PCR). For example, the methylation level of a DNA methylation marker from a sample of a subject can be quantitatively measured using a pair of primers and an oligonucleotide probe, where one primer, both primers, the oligonucleotide probe, or both primers and the oligonucleotide probe are capable of distinguishing between methylated and unmethylated nucleic acid, e.g., after the nucleic acid being modified by a modifying agent, e.g., bisulfite converting unmethylated cytosine to a converted nucleic acid.

The region of a reference gene of the present invention can be any region of a gene having one or more sites or regions that are devoid of methylation sites, e.g., devoid of CpG dinucleotides. For example, the region of a reference gene can be a region that having two primer binding sites for amplification such as PCR that are devoid of CpG dinucleotides or a region having at least one specific oligonucleotide probe binding site for real-time PCR that is devoid of CpG dinucleotides. In one aspect, the region of a reference gene of the present invention is a region of MYOD gene. In another aspect, the region of a reference gene of the present invention is a region of ACTB gene. In yet another embodiment, the region of a reference gene of the present invention is a region that is not frequently subject to copy number alterations, such as gene amplification or deletion.

In general, according to the present invention the level of a region of a reference gene is quantitatively measured using real-time PCR with primers and specific probes that specifically bind to sites after bisulfite conversion but without discriminating directly or indirectly the methylation status of the sites.

In certain embodiments, methods for detecting neoplasm in a subject are provided. Such methods comprise, for example, obtaining a sample comprising DNA from a subject; treating the obtained DNA with a reagent which selectively modifies unmethylated cytosine residues in the obtained DNA to produce modified residues but which does not modify methylated cytosine residues; determining the methylation level of one or more DNA methylation markers in the DNA having undergone the treating of step b), wherein one or more DNA methylation markers comprises a base in a differentially methylated region (DMR) as provided herein; comparing the determined methylation level of the one or more DNA methylation markers with methylation level references for the one or more DNA methylation markers for subjects not having neoplasm; and identifying the subject as having neoplasm when the methylation state of or more of the DNA methylation markers is different than a methylation state of the marker assayed in a subject that does not have a neoplasm.

In some embodiments, a determination of elevated methylation in one or more of the DNA methylation markers comprises a determination of altered methylation within a region selected from the group consisting of a CpG island and a CpG island shore.

In some embodiments, a determination of elevated methylation within said CpG island or CpG shore comprises elevated methylation within a coding region or a regulatory region of the DNA methylation marker.

In some embodiments, the determining the methylation level of one or more DNA methylation markers in the DNA having undergone the treating of step b) comprises determining the methylation score and/or the methylation frequency of the one or more DNA methylation markers.

In some embodiments, the treating of step b) is accomplished through bisulfite modification of the obtained DNA.

In some embodiments, the determining the methylation level of one or more DNA methylation markers in the DNA having undergone the treating of step b) is achieved by a technique selected from the group consisting of methylation-specific PCR, quantitative methylation-specific PCR, methylation-sensitive DNA restriction enzyme analysis, quantitative bisulfite pyrosequencing, and bisulfite genomic sequencing PCR.

In some embodiments, the neoplasm is colorectal cancer, a large colorectal adenoma, and/or a sessile serrated polyp.

In certain embodiments, methods for detecting neoplasm in a subject are provided. Such embodiments comprise, for example, determining a methylation ratio of a sample from a subject, wherein the methylation ratio is the level of methylation of a bisulfite-treated region of one or more DNA methylation markers relative to a level of bisulfite-treated DNA copy number of a reference gene, wherein the one or more DNA methylation markers comprises a base in a differentially methylated region (DMR) as provided herein, wherein the reference gene is MYOD or ACTB, identifying the subject as having neoplasm when the methylation ratio of one or more of the DNA methylation markers is different than the methylation ratio of the respective marker assayed in a subject that does not have a neoplasm.

In some embodiments, level of methylation is determined by using real-time polymerase chain reaction (PCR). In some embodiments, the level of methylation is determined by using real-time polymerase chain reaction (PCR), wherein at least one primer used in the PCR is capable of distinguishing between unmethylated and methylated nucleic acid. In some embodiments, the level of methylation is determined by using real-time polymerase chain reaction (PCR), wherein both primers used in the PCR are capable of distinguishing between unmethylated and methylated nucleic acid. In some embodiments, the level of methylation is determined by using real-time polymerase chain reaction (PCR), wherein a probe used in the PCR is capable of distinguishing between unmethylated and methylated nucleic acid. In some embodiments, the level of methylation is determined by using real-time polymerase chain reaction (PCR), wherein both primers and a probe used in the PCR are capable of distinguishing between unmethylated and methylated nucleic acid. In some embodiments, the level of the region in the reference gene is determined by using real-time polymerase chain reaction (PCR). In some embodiments, the level of the region in the reference gene is determined by using real-time polymerase chain reaction (PCR), wherein the region contains a first and second primer binding site and a probe binding site and wherein the first and second primer binding site and the probe binding site are devoid of CpG dinucleotides. In some embodiments, the region in the reference gene is devoid of CpG dinucleotides.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g. as provided in Tables 1-6); comparing methylation states (e.g., of one or more DMR, e.g. as provided in Tables 1-6); generating standard curves; determining a Ct value; calculating a fraction, frequency, or percentage of methylation (e.g., of one or more DMR, e.g. as provided in Tables 1-6); identifying a CpG island; determining a specificity and/or sensitivity of an assay or marker; calculating an ROC curve and an associated AUC; sequence analysis; all as described herein or is known in the art.

In some embodiments, a software or hardware component receives the results of multiple assays and determines a single value result to report to a user that indicates a cancer risk based on the results of the multiple assays (e.g., determining the methylation state of multiple DMR, e.g. as provided in Tables 1-6). Related embodiments calculate a risk factor based on a mathematical combination (e.g., a weighted combination, a linear combination) of the results from multiple assays, e.g., determining the methylation states of multiple markers (such as multiple DMR, e.g. as provided in Tables 1-6). In some embodiments, the methylation state of a DMR defines a dimension and may have values in a multidimensional space and the coordinate defined by the methylation states of multiple DMR is a result, e.g., to report to a user, e.g., related to a colorectal cancer risk.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of screening for a colorectal neoplasm in a sample (e.g., stool sample, colorectal tissue sample; blood sample; blood product sample) obtained from a subject (e.g., a human subject), the method comprising assaying a methylation state of a marker in a sample obtained from a subject; and identifying the subject as having a colorectal neoplasm when the methylation state of the marker is different than a methylation state of the marker assayed in a subject that does not have a colorectal neoplasm, wherein the marker comprises a base in a differentially methylated region (DMR) selected from a group consisting of a DMR as provided in Tables 1-6. The technology also encompasses determining the state or stage of a colorectal cancer, e.g., in some embodiments the neoplasm is pre-cancerous. Some embodiments provide methods comprising assaying a plurality of markers, e.g., comprising assaying 2 to 11 markers.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample, a colorectal tissue sample, a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NOs:

1-110. In some embodiments are provided an oligonucleotide comprising a sequence complementary to a chromosomal region having a base in a DMR, e.g., an oligonucleotide sensitive to methylation state of a DMR.

The technology provides various panels of markers, e.g., in some embodiments the marker comprises a chromosomal region having an annotation that is FLI1, OPLAH, DTX1, MATK, SFMBT2 region 2, KCNK12, VAV3 region 1, SFMBT2 region 3, PPP2R5C, CHST2 region 2, PKIA, PDGFD, ELOVL2, CHST2 region 1, SFMBT2 region 1, QKI, VAV3 region 2, and SLC8A3, and that comprises the marker (see, Table 1). In some embodiments the marker comprises a chromosomal region having an annotation that is BMP3, NDRG4, PDGFG, CHST2, and SFMBT2, and that comprises the marker (see, Table 2). In some embodiments the marker comprises one or more of the chromosomal regions provided in Table 3 (for colorectal cancer), Table 4 (for adenoma), and Table 5 (for SSP).

In addition, embodiments provide a method of analyzing a DMR from Tables 1-6. Some embodiments provide determining the methylation state of a marker, wherein a chromosomal region having an annotation that is FLI1, OPLAH, DTX1, MATK, SFMBT2 region 2, KCNK12, VAV3 region 1, SFMBT2 region 3, PPP2R5C, CHST2 region 2, PKIA, PDGFD, ELOVL2, CHST2 region 1, SFMBT2 region 1, QKI, VAV3 region 2, and SLC8A3, and/or a chromosomal region having an annotation that is BMP3, NDRG4, PDGFG, CHST2, and SFMBT2 comprises the marker. Some embodiments provide determining the methylation state of a marker, wherein a chromosomal region as provided in Tables 3, 4 and/or 5 comprises the marker.

Kit embodiments are provided, e.g., a kit comprising a bisulfite reagent; and a control nucleic acid comprising a sequence from a DMR selected from any of the chromosomal regions provided in Tables 1-6 and having a methylation state associated with a subject who does not have a cancer. In some embodiments, kits comprise a bisulfite reagent and an oligonucleotide as described herein. In some embodiments, kits comprise a bisulfite reagent; and a control nucleic acid comprising a sequence from a DMR selected from any of the chromosomal regions provided in Tables 1-6 and having a methylation state associated with a subject who has colorectal cancer, adenoma and/or SSP. Some kit embodiments comprise a sample collector for obtaining a sample from a subject (e.g., a stool sample); reagents for isolating a nucleic acid from the sample; a bisulfite reagent; and an oligonucleotide as described herein.

The technology is related to embodiments of compositions (e.g., reaction mixtures). In some embodiments are provided a composition comprising a nucleic acid comprising a DMR and a bisulfite reagent. Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for a colorectal neoplasm in a sample obtained from a subject, e.g., a method comprising determining a methylation state of a marker in the sample comprising a base in a DMR selected from any of the chromosomal regions provided in Tables 1-6; comparing the methylation state of the marker from the subject sample to a methylation state of the marker from a normal control sample from a subject who does not have a cancer; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a bisulfite reagent to produce a bisulfite-reacted nucleic acid; sequencing the bisulfite-reacted nucleic acid to provide a nucleotide sequence of the bisulfite-reacted nucleic acid; comparing the nucleotide sequence of the bisulfite-reacted nucleic acid with a nucleotide sequence of a nucleic acid comprising the DMR from a subject who does not have a cancer to identify differences in the two sequences; and identifying the subject as having a colorectal neoplasm when a difference is present.

Systems for screening for a colorectal neoplasm in a sample obtained from a subject are provided by the technology. Exemplary embodiments of systems include, e.g., a system for screening for a colorectal neoplasm in a sample obtained from a subject, the system comprising an analysis component configured to determine the methylation state of a sample, a software component configured to compare the methylation state of the sample with a control sample or a reference sample methylation state recorded in a database, and an alert component configured to alert a user of a cancer-associated methylation state. An alert is determined in some embodiments by a software component that receives the results from multiple assays (e.g., determining the methylation states of multiple markers, e.g., DMR, e.g., as provided in Tables 1-6) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a colorectal cancer risk in a subject.

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have a cancer. Also provided are nucleic acids, e.g., a set of nucleic acids, each nucleic acid having a sequence comprising a DMR. In some embodiments the set of nucleic acids wherein each nucleic acid has a sequence from a subject who does not have a cancer. Related system embodiments comprise a set of nucleic acids as described and a database of nucleic acid sequences associated with the set of nucleic acids. Some embodiments further comprise a bisulfite reagent. And, some embodiments further comprise a nucleic acid sequencer.

The technology is related to embodiments of compositions (e.g., reaction mixtures). In some embodiments are provided a composition comprising a nucleic acid comprising a DMR (e.g., a DMR as provided in Tables 1-6) and a bisulfite reagent. Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

In certain embodiments, the present invention provides methods of screening for a colorectal neoplasm in a sample obtained from a subject having inflammatory bowel disease, the method comprising 1) assaying a methylation state of a marker in a sample obtained from a subject; and 2) identifying the subject as having a neoplasm when the methylation state of the marker is different than a methylation state of the marker assayed in a subject that does not have a neoplasm, wherein the marker comprises a base in a differentially methylated region (DMR) as provided in Table 2. In some embodiments, the neoplasm is colorectal cancer and/or flat dysplasia.

Additional embodiments will be apparent to persons skilled in the relevant art based on the teachings contained herein.

DETAILED DESCRIPTION

Provided herein is technology relating to detecting colorectal neoplasia and particularly, but not exclusively, to methods, compositions, and related uses for detecting premalignant and malignant colorectal cancer. As the technology is described herein, the section headings used are for organizational purposes only and are not to be construed as limiting the subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and polyadenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Amplification of nucleic acids generally refers to the production of multiple copies of a polynucleotide, or a portion of the polynucleotide, typically starting from a small amount of the polynucleotide (e.g., a single polynucleotide molecule, 10 to 100 copies of a polynucleotide molecule, which may or may not be exactly the same), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810) are forms of amplification. Additional types of amplification include, but are not limited to, allele-specific PCR (U.S. Pat. No. 5,639,611), assembly PCR (U.S. Pat. No. 5,965,408), helicase-dependent amplification (U.S. Pat. No. 7,662,594), Hot-start PCR (U.S. Pat. Nos. 5,773,258 and 5,338,671), intersequence-specfic PCR, inverse PCR (Triglia, et alet al. (1988) Nucleic Acids Res., 16:8186), ligation-mediated PCR (Guilfoyle, R. et al et al., Nucleic Acids Research, 25:1854-1858 (1997); U.S. Pat. No. 5,508,169), methylation-specific PCR (Herman, et al., (1996) PNAS 93(13) 9821-9826), miniprimer PCR, multiplex ligation-dependent probe amplification (Schouten, et al., (2002) Nucleic Acids Research 30(12): e57), multiplex PCR (Chamberlain, et al., (1988) Nucleic Acids Research 16(23) 11141-11156; Ballabio, et al., (1990) Human Genetics 84(6) 571-573; Hayden, et al., (2008) BMC Genetics 9:80), nested PCR, overlap-extension PCR (Higuchi, et al., (1988) Nucleic Acids Research 16(15) 7351-7367), real time PCR (Higuchi, et al et al., (1992) Biotechnology 10:413-417; Higuchi, et al., (1993) Biotechnology 11:1026-1030), reverse transcription PCR (Bustin, S. A. (2000) J. Molecular Endocrinology 25:169-193), solid phase PCR, thermal asymmetric interlaced PCR, and Touchdown PCR (Don, et al., Nucleic Acids Research (1991) 19(14) 4008; Roux, K. (1994) Biotechniques 16(5) 812-814; Hecker, et al., (1996) Biotechniques 20(3) 478-485). Polynucleotide amplification also can be accomplished using digital PCR (Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142); polymerase chain reaction; branched hybridization methods (e.g., Chiron, U.S. Pat. Nos. 5,849,481, 5,710,264, 5,124,246, and 5,624,802); rolling circle replication (e.g., U.S. Pat. Nos. 6,210,884, 6,183,960 and 6,235,502); NASBA (e.g., U.S. Pat. No. 5,409,818); molecular beacon technology (e.g., U.S. Pat. No. 6,150,097); cycling probe technology (e.g., U.S. Pat. Nos. 5,403,711, 5,011,769, and 5,660,988); ligase chain reaction (e.g., Barnay Proc. Natl. Acad. Sci USA 88, 189-93 (1991)); QuARTS assay (e.g., as provided by U.S. Pat. No. 8,361,720; and U.S. Pat. Appl. Pub. Nos. 2012/0122088 and 2012/0122106); and sandwich hybridization methods (e.g., U.S. Pat. No. 5,288,609).

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J. Mol. Biol. 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) Cancer Research 57: 594-599.

The term "METHYLIGHT™" refers to the art-recognized fluorescence-based real-time PCR technique described by Eads et al. (1999) Cancer Res. 59: 2302-2306.

The term "HEAVYMETHYL™" refers to an assay wherein methylation specific blocking probes (also referred to herein as blockers) covering CpG positions between, or covered by, the amplification primers enable methylation-specific selective amplification of a nucleic acid sample.

The term "HEAVYMETHYL™ METHYLIGHT™" assay refers to a HEAVYMETHYL™ METHYLIGHT™ assay, which is a variation of the METHYLIGHT™ assay, wherein the METHYLIGHT™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) Nucleic Acids Res. 25: 2529-2531.

The term "MSP" (Methylation-specific PCR) refers to the art-recognized methylation assay described by Herman et al. (1996) Proc. Natl. Acad. Sci. USA 93: 9821-9826, and by U.S. Pat. No. 5,786,146.

The term "COBRA" (Combined Bisulfite Restriction Analysis) refers to the art-recognized methylation assay described by Xiong & Laird (1997) Nucleic Acids Res. 25: 2532-2534.

The term "MCA" (Methylated CpG Island Amplification) refers to the methylation assay described by Toyota et al. (1999) Cancer Res. 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemimethylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) Signal Detection Theory and ROC Analysis, Academic Press, New York).

As used herein, the term "neoplasm" refers to "an abnormal mass of tissue, the growth of which exceeds and is uncoordinated with that of the normal tissues" See, e.g., Willis R A, "The Spread of Tumors in the Human Body", London, Butterworth & Co, 1952.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" of a neoplasm, adenoma, cancer, etc. is the tissue, organ, cell type, anatomical area, body part, etc. in a subject's body where the neoplasm, adenoma, cancer, etc. is located.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "marker", as used herein, refers to a substance (e.g., a nucleic acid or a region of a nucleic acid) that is able to diagnose a cancer by distinguishing cancerous cells from normal cells, e.g., based its methylation state.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, a "remote sample" as used in some contexts relates to a sample indirectly collected from a site that is not the cell, tissue, or organ source of the sample. For instance, when sample material originating from the colon or rectum is assessed in a stool sample (e.g., not from a sample taken directly from colorectal tissue), the sample is a remote sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a sub-portion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Embodiments of the Technology

In aggregate, gastrointestinal cancers account for more cancer mortality than any other organ system. Colorectal cancer (CRC) is the second most fatal cancer, domestically, with >600,000 deaths annually. While colorectal cancers are screened in the United State, compliance is poor given the cost, discomfort, and invasiveness of colonoscopy and the dismal performance of the current menu of non-invasive fecal blood tests. To lessen the burden of CRC on individuals and society, new testing strategies are needed which are both effective and patient-friendly. A non-invasive, accurate molecular test utilizing broadly informative biomarkers may provide a rational approach. A stool based assay is one such example. Colorectal cancers and pre-cancers shed cells and DNA into the digestive stream and are ultimately excreted in stool. Highly sensitive assays have been used to detect both genetic and epigenetic markers in stools of patients with CRC cancer and precancerous polyps. In a recent multi-center study, these markers were incorporated into a stool assay that exhibited sensitivity for CRC essentially equiva-lent to that of colonoscopy. New markers would be of increased value if they proved to be more sensitive, more specific, or more predictive of lesion site than existing markers. Furthermore, markers would ideally detect the critical precancerous lesions—adenomatous polyps and ser-rated polyps—in addition to CRC when applied to a screen-ing application.

The genomic mechanisms underlying colorectal cancer involve gene and chromosomal abnormalities, including single base mutations, aneuploidy, deletions, translocations, copy number alterations, and expression changes. All of these events are being intensively studied using newer genomic technologies, including massively parallel sequencing. However, genetic alterations are proving to be very heterogeneous, and in some respects random, rather than recurrent. The APC gene, for example, is the most mutated gene in CRC lesions (~90%), but the mutation sites are spread throughout 15 coding exons necessitating gene-wide analysis. This adds complexity to developing assays with the required performance levels.

Epigenetic methylation of DNA at cytosine-phosphate-guanine (CpG) island sites by DNA methyltransferases has been studied as a potential class of biomarkers in the tissues of most tumor types. In a biologically attractive mechanism, acquired methylation events in promotor regions of tumor suppressor genes are thought to silence expression, contrib-uting to oncogenesis. DNA methylation may be a more chemically and biologically stable diagnostic tool than RNA or protein expression. Furthermore, aberrant methylation markers are more broadly informative and sensitive than are individual DNA mutations and offer excellent specificity.

Clinical applications of highly discriminant markers could have great impact. For example, assay of such markers in distant media like stool or blood find use in accurate screening or diagnostic assays for detection of colorectal neoplasia.

In experiments conducted during the course of developing embodiments for the present invention, markers were iden-tified in a case-control studies by comparing the methylation state of DNA markers from colorectal tissue of subjects with colorectal neoplasia, adenoma, and/or sessile serrated pol-yps (SSP) to the methylation state of the same DNA markers from control subjects (e.g., normal tissue such as normal colon) (see, Examples 1-2, Tables 1-5).

For example, markers and/or panels of markers (e.g., a chromosomal region having an annotation selected from FLI1, OPLAH, DTX1, MATK, SFMBT2 region 2, KCNK12, VAV3 region 1, SFMBT2 region 3, PPP2R5C, CHST2 region 2, PKIA, PDGFD, ELOVL2, CHST2 region 1, SFMBT2 region 1, QKI, VAV3 region 2, and SLC8A3) were identified in a case-control study by comparing the methylation state of DNA markers (e.g., from colorectal tissue of subjects with colorectal neoplasia and/or adenoma to the methylation state of the same DNA markers from control subjects (e.g., normal tissue such as normal colon) (see, Example 1 and Tables 1A and 1B).

Markers and/or panels of markers (e.g., a chromosomal region having an annotation selected from BMP3, NDRG4, PDGFG, CHST2, and SFMBT2) were identified in case-control studies by comparing the methylation state of DNA markers from colorectal tissue of subjects having inflam-matory bowel disease and colorectal cancer to the methyl-ation state of the same DNA markers from control subjects (e.g., normal tissue such as normal colon) (see, Example 1 and Table 2).

In addition, 185, 244, and 111 DNA methylation markers specific for colorectal cancers, large adenomas, and sessile serrated polyps, respectively, were identified (see, Example 2 and Tables 3, 4 and 5). Along with the colorectal cancer cases, large adenoma cases, and sessile serrated polyps cases, normal colonic mucosa, and normal white blood cell DNA was sequenced.

Additional experiments conducted during the course of developing embodiments for the present invention demon-strated NDRG4, BMP3, OPLAH, FLI1, PDGFD, CHST_7889, SFMBT2_895, SFMBT2_896, SFMBT2_897, CHST2_7890, VAV3, and DTX1 as effective markers for detecting colorectal cancer within stool samples (see, Example 3 and Tables 6 and 7).

Accordingly, provided herein is technology for colorectal cancer screening markers that provide a high signal-to-noise ratio and a low background level when detected from samples taken from a subject (e.g., stool sample; a colorectal tissue sample). Markers were identified in a case-control studies by comparing the methylation state of DNA markers from colorectal tissue of subjects with colorectal neoplasia and/or adenoma to the methylation state of the same DNA markers from control subjects (e.g., normal tissue such as normal colon) (see, Examples 1-3 and Tables 1-6).

Although the disclosure herein refers to certain illustrated embodiments, it is to be understood that these embodiments are presented by way of example and not by way of limitation.

In particular aspects, the present technology provides compositions and methods for identifying, determining, and/or classifying a colorectal cancer. In some embodi-ments, the methods comprise determining the methylation status of at least one methylation marker in a biological sample isolated from a subject (e.g., a stool sample or a colorectal tissue sample), wherein a change in the methylation state of the marker is indicative of the presence, class, or site of a colorectal cancer. Particular embodiments relate to markers comprising a differentially methylated region (DMR, e.g., a DMR as provided in Tables 1-6) that are used for diagnosis or screening of neoplastic cellular proliferative disorders (e.g., colorectal cancer), including early detection during the pre-cancerous stages of disease. Furthermore, the markers are used for the differentiation of neoplastic from benign cellular proliferative disorders. In particular aspects, the present technology provides a method wherein a neoplastic cell proliferative disorder is distinguished from a benign cell proliferative disorder.

The markers of the present technology are particularly efficient in detecting or distinguishing between colorectal proliferative disorders, thereby providing improved means for the early detection, classification, and treatment of colorectal cancer.

In addition to embodiments wherein the methylation analysis of at least one marker, a region of a marker, or a base of a marker comprising a DMR (e.g., a DMR as provided in Tables 1-6) provided herein is analyzed, the technology also provides panels of markers comprising at least one marker, region of a marker, or base of a marker comprising a DMR with utility for the detection of colorectal cancers. In addition to embodiments wherein the methylation analysis of at least one marker, a region of a marker, or a base of a marker comprising a DMR (e.g., a DMR as provided in Tables 1-6) provided herein is analyzed, the technology also provides panels of markers comprising any type or class of makers (e.g., complete marker, region of a marker, base of a marker, etc.) having utility for the detection of colorectal cancers (e.g., an expression marker, amount of DNA, peptide, hemoglobin, etc.).

Some embodiments of the technology are based upon the analysis of the CpG methylation status of at least one marker, region of a marker, or base of a marker comprising a DMR.

In some embodiments, the present technology provides for the use of a bisulfate technique in combination with one or more methylation assays to determine the methylation status of CpG dinucleotide sequences within at least one marker comprising a DMR (e.g., a DMR as provided in Tables 1-6). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

Determination of the methylation status of CpG dinucleotide sequences in markers comprising a DMR has utility both in the diagnosis and characterization of colorectal cancers.

Combinations of Markers

In some embodiments, the technology relates to assessing the methylation state of combinations of markers comprising a DMR from Tables 1-6 (e.g., 2, 3, 4, 5, 6, 7, 8, 9, 10, 11, 12, 13, 14, 15, 16, 17, 18, 19, 20, 21, 22, 23, 24, 25, 26, 27, 27, 29, 30) or more markers comprising a DMR. In some embodiments, assessing the methylation state of more than one marker increases the specificity and/or sensitivity of a screen or diagnostic for identifying a colorectal neoplasm in a subject. In addition to embodiments wherein the methylation analysis of at least one marker, a region of a marker, or a base of a marker comprising a DMR (e.g., a DMR as provided in Tables 1-6) provided herein is analyzed, the technology also provides panels of markers comprising any type or class of makers (e.g., complete marker, region of a marker, base of a marker, etc.) having utility for the detection of colorectal cancers (e.g., an expression marker, amount of DNA, peptide, hemoglobin, etc.).

Various cancers are predicted by various combinations of markers, e.g., as identified by statistical techniques related to specificity and sensitivity of prediction. The technology provides methods for identifying predictive combinations and validated predictive combinations for some cancers.

Methods for Assaying Methylation State

A method for analyzing a nucleic acid for the presence of 5-methylcytosine is based upon the bisulfite method described by Frommer, et al. for the detection of 5-methylcytosines in DNA (Frommer et al. (1992) Proc. Natl. Acad. Sci. USA 89: 1827-31) or variations thereof. The bisulfite method of mapping 5-methylcytosines is based on the observation that cytosine, but not 5-methylcytosine, reacts with hydrogen sulfite ion (also known as bisulfite). In some embodiments, the reaction is performed according to the following steps: first, cytosine reacts with hydrogen sulfite to form a sulfonated cytosine. Next, spontaneous deamination of the sulfonated reaction intermediate results in a sulfonated uracil. Finally, the sulfonated uricil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98) or methylation-specific PCR (MSP) as is disclosed, e.g., in U.S. Pat. No. 5,786,146.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" Nucleic Acids Res. 24: 5064-6). It is thus possible to analyze individual cells for methylation status, illustrating the utility and sensitivity of the method. An overview of conventional methods for detecting 5-methylcytosine is provided by Rein, T., et al. (1998) Nucleic Acids Res. 26: 2255.

The bisulfite technique typically involves amplifying short, specific fragments of a known nucleic acid subsequent to a bisulfite treatment, then either assaying the product by sequencing (Olek & Walter (1997) Nat. Genet. 17: 275-6) or a primer extension reaction (Gonzalgo & Jones (1997) Nucleic Acids Res. 25: 2529-31; WO 95/00669; U.S. Pat. No. 6,251,594) to analyze individual cytosine positions. Some methods use enzymatic digestion (Xiong & Laird (1997) Nucleic Acids Res. 25: 2532-4). Detection by hybridization has also been described in the art (Olek et al., WO 99/28498). Additionally, use of the bisulfite technique for methylation detection with respect to individual genes has been described (Grigg & Clark (1994) Bioessays 16: 431-6, Zeschnigk et al. (1997) Hum Mol Genet. 6: 387-95; Feil et al. (1994) Nucleic Acids Res. 22: 695; Martin et al. (1995) Gene 157: 261-4; WO 9746705; WO 9515373).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) Proc. Natl. Acad. Sci. USA 89: 1827-1831). Additionally, restriction enzyme digestion of PCR products amplified from bisulfite-converted DNA finds use in assessing methylation state, e.g., as described by Sadri & Hornsby (1997) Nucl. Acids Res. 24: 5058-5059 or as embodied in the method known as COBRA (Combined Bisulfite Restriction Analysis) (Xiong & Laird (1997) Nucleic Acids Res. 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "METHYLIGHT™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HEAVYMETHYL™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HEAVYMETHYL™ METHYLIGHT™" assay refers to a HEAVYMETHYL™ METHYLIGHT™ assay, which is a variation of the METHYLIGHT™ assay, wherein the METHYLIGHT™ assay is combined with methylation specific blocking probes covering CpG positions between the amplification primers. The HEAVYMETHYL™ assay may also be used in combination with methylation specific amplification primers.

Typical reagents (e.g., as might be found in a typical METHYLIGHT™-based kit) for HEAVYMETHYL™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The METHYLIGHT™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the METHYLIGHT™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The METHYLIGHT™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HEAVYMETHYL™ and MSP techniques) or with oligonucleotides covering potential methylation sites.

The METHYLIGHT™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical METHYLIGHT™-based kit) for METHYLIGHT™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HEAVYMETHYL™ and MSP techniques) or with oligonucleotides covering potential methylation sites.

The QM™ process can by used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The MS-SNUPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical MS-SNUPE™-based kit) for MS-SNUPE™ analysis may include, but are not limited to: PCR primers for specific loci (e.g., specific genes, markers, DMR, regions of genes, regions of markers, bisulfite treated DNA sequence, CpG island, etc.); optimized PCR buffers and deoxynucleotides; gel extraction kit; positive control primers; MS-SNUPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) Nat Methods 7: 133-6; Meissner et al. (2005) Nucleic Acids Res. 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes cleavase to release the flap sequence by cutting between the detection probe and the flap sequence. The flap sequence is complementary to a nonhairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" Clin Chem 56: A199; U.S. Pat. No. 8,361,720 and U.S. patent application Ser. Nos. 13/594,674, 12/946,745, and 12/946,752.

In some embodiments, target nucleic acid is isolated from a sample through, for example, a direct gene capture. For example, in some embodiments, target nucleic acid is isolated from a sample through, for example, removal of assay inhibiting agents to produce a clarified sample (e.g., with PVP, PVPP and/or the use of a spin filter), capture of a target nucleic acid (if present) from the clarified sample with a capture reagent to form a capture complex, isolating the capture complex from the clarified sample, recovering the target nucleic acid (if present) from the capture complex in a nucleic acid solution, and optionally repeating for isolation of different targets (see, e.g., U.S. patent application Ser. Nos. 14/145,082, 14/145,087, 14/145,070, 14/145,056, 13/470,251, 13/470,018, 13/469,999 and 13/469,989).

In some embodiments, fragments of the treated DNA are amplified using sets of primer oligonucleotides according to the present invention (e.g., see Table 2) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., a DMR as provided in Tables 1-6) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

In some embodiments, methods for isolating DNA comprise isolation of nucleic acids as described in U.S. patent application Ser. No. 13/470,251 ("Isolation of Nucleic Acids").

Methods

In some embodiments the technology, methods are provided that comprise the following steps:
1) contacting a nucleic acid (e.g., genomic DNA, e.g., isolated from a body fluids such as a stool sample or colorectal tissue) obtained from the subject with at least one reagent or series of reagents that distinguishes between methylated and non-methylated CpG dinucleotides within at least one marker DMR (e.g., a DMR as provided in Tables 1-6) and
2) detecting a colorectal neoplasm or proliferative disorder (e.g., colorectal cancer, large adenoma, SSP) (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample or colorectal tissue) obtained from the subject with at least one reagent or series of reagents that distinguishes between methylated and non-methylated CpG dinucleotides within at least one marker selected from a chromosomal region having an annotation selected from the group consisting of BMP3, NDRG4, FLI1, OPLAH, DTX1, MATK, SFMBT2 region 2, KCNK12, VAV3 region 1, SFMBT2 region 3, PPP2R5C, CHST2 region 2, PKIA, PDGFD, ELOVL2, CHST2 region 1, SFMBT2 region 1, QKI, VAV3 region 2, and SLC8A3, and
2) detecting colorectal cancer (e.g., afforded with a sensitivity of greater than or equal to 80% and a specificity of greater than or equal to 80%).

Preferably, the sensitivity is from about 70% to about 100%, or from about 80% to about 90%, or from about 80% to about 85%. In some embodiments, the specificity is from about 70% to about 100%, or from about 80% to about 90%, or from about 80% to about 85%. In some embodiments, the specificity is from about 90% to about 100%, 91% to 99%, 93% to 97%, 94% to 96%, 95% to 99%, 96% to 99.5%, 97% to 99.9%, etc.).

Genomic DNA may be isolated by any means, including the use of commercially available kits. Briefly, wherein the DNA of interest is encapsulated by a cellular membrane the biological sample should be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All sample types comprising neoplastic matter or pre-neoplastic matter are suitable for use in the present method, e.g., cell lines, histological slides, biopsies, paraffin-embedded tissue, body fluids, stool, colonic effluent, urine, blood plasma, blood serum, whole blood, isolated blood cells, cells isolated from the blood, and combinations thereof.

The technology is not limited in the methods used to prepare the samples and provide a nucleic acid for testing.

For example, in some embodiments, a DNA is isolated from a stool sample or from blood or from a plasma sample using direct gene capture, e.g., as detailed in U.S. patent application Ser. Nos. 14/145,082, 14/145,087, 14/145,070, 14/145,056, 13/470,251, 13/470,018, 13/469,999 and 13/469,989.

The genomic DNA sample is then treated with at least one reagent, or series of reagents, that distinguishes between methylated and non-methylated CpG dinucleotides within at least one marker comprising a DMR (e.g., a DMR as provided in Tables 1-6).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfate (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR as provided in Tables 1-6). In some embodiments, the method of analysis is QuARTS and/or MSP as described herein.

Aberrant methylation, more specifically hypermethylation of a marker comprising a DMR (e.g., a DMR as provided in Tables 1-6) is associated with a colorectal cancer.

The technology relates to the analysis of any sample associated with a colorectal cancer. For example, in some embodiments the sample comprises a tissue and/or biological fluid obtained from a patient. In some embodiments, the sample comprises a secretion. In some embodiments, the sample comprises blood, serum, plasma, gastric secretions, colorectal tissue, colorectal tumor tissue, a colorectal biopsy sample, pancreatic juice, a gastrointestinal biopsy sample, microdissected cells from a gastrointestinal biopsy, gastrointestinal cells sloughed into the gastrointestinal lumen, and/or gastrointestinal cells recovered from stool. In some embodiments, the subject is human. These samples may originate from the upper gastrointestinal tract, the lower gastrointestinal tract, or comprise cells, tissues, and/or secretions from both the upper gastrointestinal tract and the lower gastrointestinal tract. The sample may include cells, secretions, or tissues from the liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any variety of techniques. For instance, urine and fecal samples are readily attainable, while blood, ascites, serum, colorectal, or pancreatic fluid samples can be obtained parenterally by using a needle and syringe, for instance. Cell free or substantially cell free samples can be obtained by subjecting the sample to various techniques including, but not limited to, centrifugation and filtration. Although it is generally preferred that no invasive techniques are used to obtain the sample, it still may be preferable to obtain samples such as tissue homogenates, tissue sections, and biopsy specimens In some embodiments, the technology provides a method for treating a patient (e.g., a patient with colorectal cancer, with early stage colorectal cancer, or who may develop colorectal cancer), the method comprising determining the methylation state of one or more DMR as provided herein and administering a treatment to the patient based on the results of determining the methylation state. The treatment may be conducting a colonoscopy, administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments, clinical cancer prognosis includes determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments or monitoring.

In some embodiments of the presently disclosed subject matter, multiple determination of the biomarkers over time are made to facilitate diagnosis and/or prognosis. A temporal change in the biomarker is used to predict a clinical outcome, monitor the progression of gastrointestinal cancer, and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

In some embodiments, the methods and compositions of the invention are employed for treatment or diagnosis of disease at an early stage, for example, before symptoms of the disease appear.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biamarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with a gastrointestinal cancer. In certain embodiments of the method, a subject is identified as having metaplasia upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats may be used to facilitate immediate treatment and diagnosis in a timely fashion, for example, in ambulatory transport or emergency room settings.

In some embodiments, the subject is diagnosed as having a colorectal cancer if, when compared to a control methylation state, there is a measurable difference in the methylation state of at least one biomarker in the sample. Conversely, when no change in methylation state is identified in the biological sample, the subject can be identified as not having colorectal cancer, not being at risk for the cancer, or as having a low risk of the cancer. In this regard, subjects having the cancer or risk thereof can be differentiated from subjects having low to substantially no cancer or risk thereof. Those subjects having a risk of developing a colorectal cancer can be placed on a more intensive and/or regular screening schedule, including endoscopic surveillance. On the other hand, those subjects having low to substantially no risk may avoid being subjected to an endoscopy, until such time as a future screening, for example, a screening conducted in accordance with the present technology, indicates that a risk of colorectal cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, a gastrointestinal cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

The presently-disclosed subject matter further includes a system for diagnosing a gastrointestinal cancer in a subject. The system can be provided, for example, as a commercial kit that can be used to screen for a risk of gastrointestinal cancer or diagnose a gastrointestinal cancer in a subject from whom a biological sample has been collected. An exemplary system provided in accordance with the present technology includes assessing the methylation state of a DMR as provided in Tables 1-6.

EXAMPLES

Example 1

This example describes independent case-control tissue studies which identified highly discriminant methylation markers for colorectal neoplasia. The examples used RRBS for the discovery phase and methylation-specific PCR (MSP) and quantitative allele-specific real-time target and signal amplification (QuARTs) for the validation phase.

Tissue samples were identified from existing cancer registries. The accessible population included those who underwent either open or laparoscopic colectomy, or colon biopsy with an archived specimen. All tissues were reviewed by an expert gastrointestinal pathologist to confirm correct classification. Colorectal neoplasia case tissues included stages I-IV colorectal cancers (fresh-frozen), advanced adenomas >1 cm in size (fresh-frozen), and right-sided sessile serrated polyps (FFPE). There were two control groups studied. The first control group included 18 colonic epithelial tissues from patients confirmed to be free from colonic neoplasm. The second group included 18 normal buffy coat samples from cancer free patients. Cases and both controls were matched by sex and age. In addition, the CRC and advanced adenoma cohorts were evenly distributed between right and left sided lesions. In a central core laboratory, case and control tissues were micro-dissected and DNA was extracted using a phenol-chloroform technique, yielding at least 500 ng of DNA. Case identification, matching and DNA extraction were performed by independent personnel to maintain blinding of laboratory personnel to case and control status.

Genomic DNA (300 ng) was fragmented by digestion with 10 Units of MspI, a methylation-specific restriction enzyme which recognizes CpG containing motifs. This enriches the samples for CpG content and eliminates redundant areas of the genome. Digested fragments were end-repaired and A-tailed with 5 Units of Klenow fragment (3'-5' exo-), and ligated overnight to methylated TruSeq adapters (Illumina, San Diego Calif.) containing one of four barcode sequences (to link each fragment to its sample ID.) Size selection of 160-340 bp fragments (40-220 bp inserts) was performed using Agencourt AMPure XP SPRI beads/buffer (Beckman Coulter, Brea Calif.). Buffer cutoffs were 0.7× to 1.1× sample volumes of beads/buffer. Final elution volume was 22 uL (EB buffer—Qiagen, Germantown Md.) qPCR was used to gauge ligation efficiency and fragment quality on a small aliquot of sample. Samples then underwent bisulfite conversion (twice) using a modified EpiTect protocol (Qiagen). qPCR and conventional PCR (PfuTurbo Cx hotstart—Agilent, Santa Clara Calif.) followed by Bioanalyzer 2100 (Agilent) assessment on converted sample aliquots determined the optimal PCR cycle number prior to amplification of the final library. Conditions for final PCR: 50 uL rxn: 5 uL of 10× buffer, 1.25 uL of 10 mM each dNTP's, 5 uL primer cocktail (~5 uM), 15 uL template (sample), 1 uL PfuTurbo Cx hotstart, 22.75 water. 95 C-5 min; 98 C-30 sec; 16 cycles of 98 C-10 sec, 65 C-30 sec, 72 C-30 sec; 72 C-5 min; 4 C. Samples were combined (equimolar) into 4-plex libraries based on the randomization scheme and tested with the bioanalyzer for final size verification, and with qPCR using phiX standards and adaptor-specific primers.

Samples were loaded onto flow cell lanes according to a randomized lane assignment with additional lanes reserved for internal assay controls. Sequencing was performed by the Next Generation Sequencing Core at the Mayo Clinic Medical Genome Facility on the Illumina HiSeq 2000. Reads were unidirectional for 101 cycles. Each flow cell lane generated 100-120 million reads, sufficient for a median coverage of 30-50 fold sequencing depth (read number per CpG) for aligned sequences. Standard Illumina pipeline software was used for base calling and sequence read generation in the fastq format. As previously (see, e.g., Sun, et al., 2012 Bioinformatics 28(16):2180-1), SAAP-RRBS, a streamlined analysis and annotation pipeline for reduced representation bisulfite sequencing, was used for sequence alignment and methylation extraction.

Two MSP-based validation studies were performed on expanded sample sets to confirm the accuracy and reproducibility of the observed differentially methylated candidates. The first, an internal validation (MSP) study, was performed on matched, blinded samples using biological and technical replicates of colorectal neoplasia, normal colon, and normal leukocytes. This step was performed to ensure that the sites of differential methylation identified by the RRBS data filtration, where % methylation was the unit of analysis, would be reflected in MSP, where the unit of analysis is the absolute genomic copy number of the target sequence, corrected by the concentration of input DNA for each sample. The second, external validation experiment, utilized QuARTs technology to test the top candidates in randomly allocated, matched, blinded, independent colorectal neoplasia and normal colon samples.

Primers for each marker were designed to target the bisulfite-modified methylated sequences of each target gene (IDT, Coralville Iowa) and a region without cytosine-phosphate-guanine sites in the β-actin gene, as a reference of bisulfite treatment and DNA input. The design was done by either Methprimer software (University of California, San Francisco Calif.) or by semi-manual methods. Assays were then tested and optimized by running qPCR with SYBR Green (Life Technologies, Grand Island N.Y.) dyes on dilutions of universally methylated and unmethylated genomic DNA controls.

MSP reactions were performed on tissue-extracted DNA as previously described (see, e.g., Kisiel, et al., 2012 Cancer 118(10):2623-2631). Briefly, DNA was bisulfite treated using the EZ DNA Methylation Kit (Zymo Research, Orange, Calif.) and eluted in buffer. 1 μl of bisulfite-treated DNA was used as a template for methylation quantification with a fluorescence-based real-time PCR, performed with SYBR Green master mix (Roche, Mannheim Germany). Reactions were run on Roche 480 LightCyclers (Indianapolis, Ind.), where bisulfite-treated CpGenome Universal Methylated DNA (Millipore, Billerica, Mass.) was used as a positive control, and serially diluted to create standard curves for all plates. Oligonucleotide sequences and annealing temperatures are available upon request.

The primary comparison of interest was the methylation difference between cases and colon controls at each mapped CpG. CpG islands are biochemically defined by an observed to expected CpG ratio exceeding 0.6 (31). However, for this model, tiled units of CpG analysis "differentially methylated region (DMR)" were created based on the distance between CpG site locations for each chromosome. As the distance between any given CpG exceeded the previous or next location by more than 100 bps, a new island identifier was created. Islands with only a single CpG were excluded. The secondary outcome was the same comparison between cases and leukocyte controls. Individual CpG sites were considered for differential analysis only if the total depth of coverage per disease group was ≥200 reads (roughly equating to an average of 10 reads per subject) and the variance of % methylation was greater than zero (non-informative CpG sites with 0 variance were excluded). The criteria for read depth were based on the desired statistical power to detect a difference of 10% in the methylation rate between any two groups in which the sample size of individuals for each group was 18.

Statistical significance was determined by logistic regression on the % methylation per DMR (using the actual counts) with the groups defined as colorectal neoplasia, normal colon, and normal leukocytes. To account for varying read depths across individual subjects, an over-dispersed logistic regression model was used, where dispersion parameter was estimated using the Pearson Chi-square statistic of the residuals from fitted model. To assess strand specific methylation, forward and reverse regions were analyzed separately. The DMRs were then ranked according to their significance level and were considered as a viable marker region if the methylation rate in the controls was ≤2.5% but ≥10% in cases. Each significant DMR was considered as a candidate marker.

For the internal validation study, the primary outcome was the area under the receiver operating characteristics curve (AUC) for each marker. This was calculated using logistic regression (JMP version 9.0.1, SAS Institute, Cary N.C.) to model the strength of the median corrected copy number of each marker with colorectal neoplasia in comparison to normal colon and normal leukocytes. The markers with the highest AUC values and widest ratio of median marker copy number between cases and controls were selected for the external validation study. The primary outcome for the external validation experiment was the AUC for each marker plotted against the signal strength of each marker, measured by the log of the ratio of median corrected % methylation in cases compared to controls. With eighteen cases there is >80% power to detect an area under the curve of 0.85 or higher from the null hypothesis of 0.5 at a two-sided significance level 0.05.

RRBS Marker Discovery

Matched, blinded, randomly allocated DNA extracts from 18 colorectal cancers, 18 advanced adenomas (>1 cm), 18 sessile serrated polyps, 18 normal colon epithelial tissues, and 18 normal buffy coat derived leukocyte controls were sequenced by RRBS. Median age was 65 (interquartile range 60-70), and 51% were women. 4-5 million CpGs per sample were generated from the sequencing data. After selecting only CpG sites where group coverage and variance criteria were met, an approximate range of 2-3 million CpG sites were considered for further analysis. SSA samples, which were derived from FFPE tissue blocks, had a lower number of CpGs (200,000-1.2 million) due to lower inherent quality). 1068 (CRC), 1200 (advanced adenoma), and 268 (SSA) DMRs met significance criteria for differential methylation. These clustered into 185, 244, and 109 candidate regions with sufficient methylation signatures for MSP primer design. The length of DMRs ranged between 30 to over 1000 bases. Methylation signatures contained 6 to 69 contiguous CpGs. 84% of the DMRs annotate to the 5' regulatory (promoter) regions of genes, most of which associate with larger CpG islands. In the case of the CRC DMRs, approximately 15% have previous associations with colorectal neoplasia. 50% have been reported in other types of cancer. Of the remaining 25%, approximately half segregate into cancer relevant pathways (transcription factors, signaling, cell cycle regulators, membrane transporters, etc.) A number of the annotated sites contain multiple DMRs.

Internal Validation

Based on the number of neighboring CpGs in each candidate gene methylation signature, primers were designed for the top 50 candidates of the 185 CRC markers. Ranking was done by reference to logistic regression metrics and case/control copy number ratio. 35 of these passed internal performance QC and 15 were rejected. MSP was then used to assay the 35 candidates in samples of DNA from additional matched, blinded, partially independent cohorts, including 36 CRC lesions, 36 advanced adenomas, and 36 normal colonic epithelial samples. In addition, 31 DNA samples extracted from inflammatory bowel disease (IBD) patients (18 with CRC, 2 with high grade dysplasia, and 13 normal controls.) β-actin amplified in all samples. Of the 35 MSP assays, 18 candidate markers had an AUC>0.88, case/control copy number ratios >50, and background methylation <1% (see Table 1A and 1B). These were selected for inclusion in an independent external validation.

TABLE 1A

Most Discriminate Markers in Independent Tissues by MSP including DMR Genomic Coordinates

| Marker | AUC | Median S/N | Background Methylation (%) | Chromosome | DMR Genomic Coordinates |
|---|---|---|---|---|---|
| FLI1 | 0.986 | >1000 | 0 | 11 | 128563956-128564209 |
| OPLAH | 0.981 | 67 | 0.25 | 8 | 145106349-145106456 |
| DTX1 | 0.974 | >1000 | 0 | 12 | 113494586-113494957 |
| MATK | 0.972 | 64 | 0.63 | 19 | 3785828-3786371 |
| SFMBT2 region 2 | 0.971 | 90 | 0.71 | 10 | 7452746-7452779 |
| KCNK12 | 0.963 | >1000 | 0 | 2 | 47797187-47797452 |
| VAV3 region 1 | 0.954 | 135 | 0.27 | 1 | 108507074-108507498 |
| SFMBT2 region 3 | 0.952 | >1000 | 0 | 10 | 7452885-7452956 |
| PPP2R5C | 0.949 | >1000 | 0.1 | 14 | 102247525-102247929 |
| CHST2 region 2 | 0.947 | >1000 | 0 | 3 | 142838645-142839023 |
| PKIA | 0.945 | >1000 | 0.01 | 8 | 79428485-79428684 |
| PDGFD | 0.944 | >1000 | 0 | 11 | 104034769-104034920 |
| ELOVL2 | 0.935 | 70 | 0.79 | 6 | 11044395-11044834 |
| CHST2 region 1 | 0.931 | 390 | 0.07 | 3 | 142838025-142838494 |
| SFMBT2 region 1 | 0.931 | >1000 | 0 | 10 | 7452029-7452452 |
| QKI | 0.921 | 50 | 0.61 | 6 | 163834534-163834925 |
| VAV3 region 2 | 0.892 | >1000 | 0 | 1 | 108507609-108507674 |
| SLC8A3 | 0.883 | 596 | 0.1 | 14 | 70655516-70655712 |

TABLE 1B

Most Discriminate Markers in Independent Tissues by MSP including Forward MSP Primers and Reverse MSP Primers

| Marker | Forward MSP Primer | Reverse MSP Primer |
|---|---|---|
| FLI1 | GGGAGTGAGGGTAGGGCGTTC (SEQ ID NO: 1) | CTCGCAACCCCTTCGAATTAACCCG (SEQ ID NO: 2) |

TABLE 1B-continued

Most Discriminate Markers in Independent Tissues by MSP including
Forward MSP Primers and Reverse MSP Primers

| Marker | Forward MSP Primer | Reverse MSP Primer |
|---|---|---|
| OPLAH | TGCGTAGGTGATAGGGAGGGGTTAC (SEQ ID NO: 3) | ACAAAACACATCCTATTAACGCGAA (SEQ ID NO: 4) |
| DTX1 | GAGTCGCGGTTTCGTTTTC (SEQ ID NO: 5) | GACGCGACGACCGAAAAAC (SEQ ID NO: 6) |
| MATK | TGCACACCCCGAGGCGGTCCCGG (SEQ ID NO: 7) | CGCCCCCAAAATAAAAAAACGAA (SEQ ID NO: 8) |
| SFMBT2 region 2 | GCGTTTAGGTTGGTCGGAGA (SEQ ID NO: 10) | CCTAACCAACGCACTCAACC (SEQ ID NO: 11) |
| KCNK12 | CGTAGCGTGGCGTTTTAGCGC (SEQ ID NO: 12) | TCGAAAACCCCGACGAAACGAAAACG (SEQ ID NO: 13) |
| VAV3 region 1 | GCGTAAGGTCGAATATTTGAGTCGA (SEQ ID NO: 14) | AAAATACTACCCACCAACCACCGAA (SEQ ID NO: 15) |
| SFMBT2 region 3 | GTCGTCGTTCGAGAGGGTA (SEQ ID NO: 16) | CGAACAAAAACGAACGAACGAA (SEQ ID NO: 17) |
| PPP2R5C | TCGATTTTATTTTTGTTGTCGTTGTAGATTCGC (SEQ ID NO: 18) | GAAAAAACTAAAAAACGACAAAAAAACCCGACG (SEQ ID NO: 19) |
| CHST2 region 2 | GGAACGAGTGATAGTCGGATAGTTCGTC (SEQ ID NO: 20) | CGCCCGAAAACGACCCCG (SEQ ID NO: 21) |
| PKIA | CGGGGATGATTTTATGTAGTCGGAGTTTCGC (SEQ ID NO: 22) | CCCGCCGAATACTCGATCAACTCG (SEQ ID NO: 23) |
| PDGFD | GCGAATAAATAAACGTTAATTTGTTGTTTGTTTC (SEQ ID NO: 24) | CCGAACGCGTATAAATACCGCACTT (SEQ ID NO: 25) |
| ELOVL2 | CGGTTTTATTTATTATGATTCGTAGCGG (SEQ ID NO: 26) | CGACTACCCTAAACAACGCATCGC (SEQ ID NO: 27) |
| CHST2 region 1 | CGAGTTCGGTAGTTGTACGTAGA (SEQ ID NO: 28) | CGAAATACGAACGCGAAATCTAAAACT (SEQ ID NO: 29) |
| SFMBT2 region 1 | GCGACGTAGTCGTCGTTGT (SEQ ID NO: 30) | CCAACGCGAAAAAAACGCG (SEQ ID NO: 31) |
| QKI | GAGGCGGACGTCGCGGTAC (SEQ ID NO: 32) | CGCCACGACGCGAATCTTAACTACG (SEQ ID NO: 33) |
| VAV3 region 2 | GGATCGAGGGAGTAGGAGTCGC (SEQ ID NO: 34) | CGAAACCGAACCTAACGCGACG (SEQ ID NO: 35) |
| SLC8A3 | AGTTTTTTCGCGCGTTTTTTTTGC (SEQ ID NO: 36) | GCCGAATCTCCGCCTTACACG (SEQ ID NO: 37) |

Logistic analyses were also run on the IBD case/control samples. From the 35 tested markers, 3 markers (PDGFD, CHST2 7889, SFMBT2 896) were chosen for comparison with existing ColoGuard (Exact Sciences) methylation markers BMP3 and NDRG4 in an external stool based validation.

External Validation

Matched, blinded, randomly allocated DNA from 40 CRC, 24 advanced adenomas, and 40 normal colon epithelial samples were assayed by QuARTs for 18 top candidates. The median age of this subset was 60 (interquartile range 52-67). Gender balance was 50:50. Same for distal:proximal lesion percentages in cases. β-actin amplified in all samples. All 18 markers demonstrated performance in line with the results from the internal validation. In the CRC analysis, 9 markers exhibited superior performance in terms of both AUC characteristics and methylation ratios between cases and controls. As shown in the table below (Table 1C), these 9 showed excellent association with colorectal cancer.

TABLE 1C

Most Discriminate Markers Showing Association with CRC

| Marker | ROC AUC | Std. Error | Z value | Pr (>z) | Lower. 95 | Upper .95 | Mean % Methylation-Case/control |
|---|---|---|---|---|---|---|---|
| vav3_877 (VAV3 region 2) | 0.8718 | 0.0354 | 10.5 | 0 | 0.8024 | 0.9412 | 5046 |

TABLE 1C-continued

Most Discriminate Markers Showing Association with CRC

| Marker | ROC AUC | Std. Error | Z value | Pr (>z) | Lower. 95 | Upper .95 | Mean % Methylation-Case/control |
|---|---|---|---|---|---|---|---|
| chst2_7889 (CHST2 region 1) | 0.8462 | 0.0374 | 9.25 | 0 | 0.7728 | 0.9195 | 10127 |
| sfmbt2_896 (sfmbt2 region 2) | 0.9526 | 0.0251 | 18.05 | 0 | 0.9034 | 1.0017 | 139 |
| sfmbt2_895 (sfmbt2 region 1) | 0.9439 | 0.0266 | 16.72 | 0 | 0.8919 | 0.996 | 580 |
| pdgfd | 0.8814 | 0.0351 | 10.85 | 0 | 0.8125 | 0.9503 | 1351 |
| dtx1 | 0.9606 | 0.0222 | 20.77 | 0 | 0.9171 | 1.004 | 883 |
| fli1 | 0.9744 | 0.0179 | 26.51 | 0 | 0.9393 | 1.0094 | 1131 |
| sfmbt2_897 (sfmbt2 region 3) | 0.9311 | 0.0293 | 14.73 | 0 | 0.8737 | 0.9885 | 323 |
| chst2_7890 (chst2 region 2) | 0.9231 | 0.0293 | 14.46 | 0 | 0.8657 | 0.9804 | 6970 |

For the IBD stool validation study, three markers were chosen—(PDGFD, CHST2 7889, SFMBT2 896), and run in comparison with BMP3 and NDRG4.

Methylated DNA markers were discovered and piloted to measure the detection of IBD-associated CRN (IBD-CRN: low grade dysplasia [LGD], high grade dysplasia [HGD] and colorectal cancer [CRC]).

Markers were identified and tested in 3 discrete steps: discovery; biological validation; and clinical piloting. First a discovery experiment identified markers by reduced representation bisulfite sequencing (RRBS) on DNA extracted from archival frozen tissue samples of sporadic CRC and adenomas. Second, candidate markers were validated by methylation specific PCR (MSP) assay in DNA extracted from archival tissues from IBD-CRC patients and IBD controls without CRN. Third, archival stools of independent IBD-CRN cases and IBD controls were assayed by quantitative allele specific realtime target and signal amplification (QuARTS). Patients without surveillance biopsies or with prior solid organ transplant were excluded. Logistic regression measured sensitivity and specificity. Clinical variable influence was tested by Chi-square and Wilcoxon rank sum for categorical and continuous data, respectively.

18 sporadic CRC, 18 advanced adenomas and 18 normal colon samples were sequenced by RRBS; the top 20 candidates were tested by MSP in independent samples including 18 IBD-CRC and 13 IBD-controls. Three markers (PDGFD, CHST2, SFMBT2) were selected for comparison to BMP3 and NDRG4; all were assayed by QuARTS in stool samples from 33 IBD-CRN cases (8 CRC, 8 HGD, 8 LGD≥1 cm, 10 LGD<1 cm) and 50 IBD controls. Four controls were excluded for insufficient β-actin. Median IBD disease duration was 23 years (interquartile range [IQR] 9-35) in cases and 13 (8-20) years in controls (p=0.0009). No other significant differences were seen when comparing age, sex, inflammation severity, IBD extent or co-morbid primary sclerosing cholangitis. PDGFD, CHST2, SFMBT2 levels were modestly influenced by disease duration (p=0.04, 0.02, 0.04), but BMP3 and NDRG4 were not. Other variables were not significant. Detection rates at 90% specificity are reported (Table 2A, 2B, and 2C).

For CRC (n=1) and HGD (n=2) samples that were negative, H&E blocks were reviewed. One HGD sample was re-classified as reactive change. DNA was extracted from the remaining HGD and CRC tissues and assayed by QuARTS for each marker above. These were strongly positive.

QuARTS assays were repeated on the corresponding stool samples with minimal change in % methylation; however, the raw copy numbers increased for each marker, such that BMP3, NDRG4, PDGFG, CHST27889 were able to detect 8/8 CRC and 6/7 HGD (14/15 CRC+HGD, 93% sensitivity) at a specificity range of 89-93%.

TABLE 2A

Detection of IBD-associated Colorectal Neoplasms by Methylated Stool DNA at 90% Specificity

| Methylated marker | CRC (n = 8) | CRC + HGD (n = 16) | HGD (n = 8) | LGD ≥ 1 cm (n = 8) | LGD > 1 cm (n = 10) |
|---|---|---|---|---|---|
| BMP3 | 7 (88%) | 13 (81%) | 6 (75%) | 6 (75%) | 6 (60%) |
| NDRG4 | 7 (88%) | 13 (81%) | 6 (75%) | 5 (63%) | 4 (40%) |
| PDGFG | 7 (88%) | 13 (81%) | 6 (75%) | 4 (50%) | 4 (40%) |
| CHST2 | 7 (88%) | 13 (81%) | 6 (75%) | 5 (63%) | 4 (40%) |
| SFMBT2 | 7 (88%) | 13 (81%) | 6 (75%) | 5 (63%) | 3 (30%) |

TABLE 2B

Detection of IBD-associated Colorectal Neoplasms by Methylated Stool DNA at 90% Specificity including DMR Genomic Coordinates

| Methylated marker | Chromosome | DMR Genomic Coordinates |
|---|---|---|
| BMP3 | 4 | 81952348-81952402 |
| NDRG4 | 16 | 58497395-58497451 |
| PDGFG | 11 | 104034769-104034920 |
| CHST2 | 3 | 142838025-142838494 |
| SFMBT2 | 10 | 7452029-7452452 |

TABLE 2C

Detection of IBD-associated Colorectal Neoplasms by Methylated
Stool DNA at 90% Specificity including Forward MSP Primers,
Probe Sequence, and Reverse MSP Primers

| Methylated marker | Forward Primer | Probe Sequence | Reverse Primer |
|---|---|---|---|
| BMP3 | GTTTAATTTTCGGTTTCGTCGTC (SEQ ID NO: 38) | CGCCGAGGCGGTTTTTTGCG (SEQ ID NO: 39) | CGCTACGAAACACTCCGA (SEQ ID NO: 40) |
| NDRG4 | CGGTTTTCGTTCGTTTTTTCG (SEQ ID NO: 41) | CCACGGACGGTTCGTTTATCG (SEQ ID NO: 42) | CCGCCTTCTACGCGACTA (SEQ ID NO: 43) |
| PDGFG | GCGAATAAATAAACGTTAATTTGTTGTTTGTTTC (SEQ ID NO: 44) | CCACGGACGCGCACTTCCTTA (SEQ ID NO: 45) | CCGAACGCGTATAAATACCGCACTT (SEQ ID NO: 46) |
| CHST2 | CGAGTTCGGTAGTTGTACGTAGA (SEQ ID NO: 47) | CGCCGAGGTCGTCGATACCG (SEQ ID NO: 48) | CGAAATACGAACGCGAAATCTAAAACT (SEQ ID NO: 49) |
| SFMBT2 | GCGACGTAGTCGTCGTTGT (SEQ ID NO: 50) | CCACGGACGGAAAACGCGAAA (SEQ ID NO: 51) | CCAACGCGAAAAAAACGCG (SEQ ID NO: 52) |

Example 2

This example describes the identification of methylated DNA markers for detection of colorectal cancer and pre-cancer.

Disclosed herein is a set of 185 DNA methylation markers for colorectal cancer (Tables 3A and 3B), 244 for large adenomas (≥1 cm) (Tables 4A and 4B), and 111 for sessile serrated polyps (SSP) (Tables 5A and 5B)—all identified from data generated by CpG island enrichment coupled with massively parallel sequencing of a case—control tissue sample sets. Adenomas and SSPs are the critical precancerous lesions for CRC, and their detection in a screening application is important. Controls included normal colonic epithelia and normal white blood cell derived DNA. The technique utilized reduced representation bisulfite sequencing (RRBS). The tertiary and quaternary analyses are unique and integral to the marker selection process. The tertiary step involves parsing the data in terms of coverage cutoffs, excluding all non-informative sites, contrasting the % methylation between diagnostic subgroups using logistic regression, creating in-silico CpG "islands" based on defined groupings of contiguous methylation sites, and Receiver Operating Characteristic analysis. The quaternary step filters the % methylation data (both individual CpGs and the in-silico clusters) to select markers which maximize signal to noise ratios, minimize background methylation, account for tumor heterogeneity, and to emphasize ROC performance. Furthermore, this analytic approach insures identification of hotspot CpGs over a defined DNA length for easy development and optimal design of downstream marker assays—methylation specific PCR, small fragment deep sequencing, etc.

The CRC, adenoma, and control samples yielded approximately 2-3 million high quality CpGs, which after analysis and filtering resulted in approximately 1068 (CRC) and 1200 (adenoma) highly discriminate individual sites. These clustered into 185 localized regions of differential methylation for CRC and 244 for adenoma, some extending for 30-40 bases and some greater than a kilobase. From a cursory literature review, less than 15% of the DMRs appear to have a previous colorectal cancer association. Nearly 50%, however, have some previous cancer association, but not specifically epigenetic in character. The rest have either very weak or no cancer associations, although many are involved in functional pathways which may be relevant to tumorigenesis. 30 DMRs (CRC) and 42 (adenoma) had no annotation and no references anywhere in the literature. These were named MAX followed by chromosomal location and coordinates. All DMRs had AUCs of 0.85 or more (some demonstrated perfect discrimination of cases from controls with an AUC of 1.0). In addition to meeting the AUC threshold of 0.85, colon cancer and adenoma markers that were identified had to exhibit >50-fold higher methylation density in tumor than in normal gastric or colonic mucosa and <1.0% methylation in normal colonic mucosa. Based on previous experience with pancreatic cancer marker discovery and validation, these marker characteristics in tissue predict high discrimination in distant media such as stool or blood.

The SSP samples were derived from FFPE blocks and were of lower quality. For these, only half had an adequate number of reads (>100,000). As such, the filtering stringencies were reduced slightly in comparison to those used with the frozen samples. After sorting, there were 268 discriminate sites which clustered into 111 localized regions.

Some of the disclosed markers are shared between pairwise case groups, and a lesser number between all three. Others are unique to a specific group. The majority are part of defined CpG islands (e.g. GC content greater than 55%, and an observed-to-expected CpG ratio of 65% or more), and where there is annotation (association with a known gene), the location is generally in the promoter region.

TABLE 3A

Colorectal Cancer DMRs

| Chromosome | Chromosome Coordinates | Gene Annotation |
|---|---|---|
| 2 | 207308703-207308890 | ADAM23 |
| 7 | 45613877-45613977 | ADCY1 |
| 22 | 24820148-24820373 | ADORA2A |
| 7 | 44143993-44144413 | AEBP1 |
| 2 | 100721643-100721967 | AFF3 |
| 1 | 49242089-49242514 | AGBL4 |
| 6 | 151561236-151561473 | AKAP12 |
| 7 | 134142981-134143723 | AKR1B1 |
| 8 | 41754327-41754726 | ANK1 |

TABLE 3A-continued

Colorectal Cancer DMRs

| Chromosome | Chromosome Coordinates | Gene Annotation |
|---|---|---|
| 17 | 27940469-27940612 | ANKRD13B |
| 5 | 10565042-10565191 | ANKRD33B |
| 5 | 10564655-10564807 | ANKRD33B |
| 11 | 110582796-110583345 | ARHGAP20 |
| 11 | 110582170-110582657 | ARHGAP20 |
| 11 | 110581912-110582039 | ARHGAP20 |
| 12 | 103351885-103352327 | ASCL1 |
| 13 | 25946118-25946206 | ATP8A2 |
| 8 | 104152806-104153145 | BAALC |
| 9 | 96715112-96715603 | BARX1 |
| 8 | 65493937-65494105 | BHLHE22 |
| 6 | 7727566-7728088 | BMP6 |
| 6 | 105584685-105585220 | BVES |
| 17 | 43339242-43339498 | C17orf46 |
| 1 | 1475560-1475650 | C1orf70 |
| 1 | 1476065-1476127 | C1orf70 |
| 10 | 16562866-16563332 | C1QL3 |
| 10 | 16563667-16563892 | C1QL3 |
| 10 | 16562465-16562672 | C1QL3 |
| 9 | 132382813-132382909 | C9orf50 |
| 18 | 70211543-70211719 | CBLN2 |
| 3 | 128720801-128720885 | CCDC48 |
| 3 | 128719995-128720631 | CCDC48 |
| 2 | 101033758-101034005 | CHST10 |
| 12 | 104850745-104851001 | CHST11 |
| 3 | 142838025-142838494 | CHST2 |
| 3 | 142838645-142839023 | CHST2 |
| 3 | 142839223-142839576 | CHST2 |
| 5 | 178016833-178017456 | COL23A1 |
| 7 | 30721941-30722028 | CRHR2 |
| 9 | 124461296-124461420 | DAB2IP |
| 12 | 64062131-64062443 | DPY19L2 |
| 12 | 113494586-113494957 | DTX1 |
| 10 | 64575060-64575283 | EGR2 |
| 2 | 31456804-31457263 | EHD3 |
| 7 | 37487755-37488565 | ELMO1 |
| 7 | 37487539-37487623 | ELMO1 |
| 6 | 11044395-11044834 | ELOVL2 |
| 6 | 80656845-80657306 | ELOVL4 |
| 6 | 152129389-152129636 | ESR1 |
| 6 | 133562485-133562878 | EYA4 |
| 15 | 48938056-48938252 | FBN1 |
| 11 | 128563956-128564209 | FLI1 |
| 11 | 128562780-128563522 | FLI1 |
| 6 | 159590083-159590220 | FNDC1 |
| 9 | 101471421-101471519 | GABBR2 |
| 2 | 31360809-31360992 | GALNT14 |
| 2 | 31360542-31360640 | GALNT14 |
| 11 | 134146132-134146380 | GLB1L3 |
| 7 | 42276418-42277414 | GLI3 |
| 12 | 52400569-52400726 | GRASP |
| 12 | 52400919-52401166 | GRASP |
| 16 | 28074472-28074761 | GSG1L |
| 17 | 1959348-1959370 | HIC1 |
| 7 | 50343838-50344453 | IKZF1 |
| 2 | 182321830-182321983 | ITGA4 |
| 1 | 226925082-226925651 | ITPKB |
| 4 | 6201350-6201560 | JAKMIP1 |
| 2 | 47797187-47797452 | KCNK12 |
| 2 | 149633039-149633137 | KIF5C |
| 7 | 149411729-149411847 | KRBA1 |
| 19 | 8274584-8274671 | LASS4 |
| 2 | 30455594-30455705 | LBH |
| 5 | 38556357-38556743 | LIFR |
| 19 | 2290273-2290393 | LINGO3 |
| 19 | 2290645-2290738 | LINGO3 |
| 19 | 42905798-42906349 | LIPE |
| 7 | 140772542-140772873 | LOC100131199 |
| 2 | 100938402-100939005 | LONRF2 |
| 7 | 127671918-127672318 | LRRC4 |
| 19 | 41119795-41119907 | LTBP4 |
| 6 | 6546375-6546598 | LY86-AS1 |
| 19 | 3785828-3786371 | MATK |
| 10 | 22541502-22541671 | MAX.chr10.22541502-22541671 |
| 10 | 22541884-22542001 | MAX.chr10.22541884-22542001 |
| 10 | 22765155-22765223 | MAX.chr10.22765155-22765223 |
| 11 | 123301058-123301255 | MAX.chr11.123301058-123301255 |
| 11 | 123301366-123301506 | MAX.chr11.123301366-123301506 |
| 11 | 123301853-123301941 | MAX.chr11.123301853-123301941 |
| 11 | 57250528-57250611 | MAX.chr11.57250528-57250611 |
| 12 | 8171360-8171769 | MAX.chr12.8171360-8171769 |
| 14 | 100437680-100437767 | MAX.chr14.100437680-100437767 |
| 19 | 22034447-22034696 | MAX.chr19.22034447-22034696 |
| 19 | 22034799-22034887 | MAX.chr19.22034799-22034887 |
| 19 | 42444999-42445053 | MAX.chr19.42444999-42445053 |
| 2 | 144694517-144695025 | MAX.chr2.144694517-144695025 |
| 20 | 44936022-44936246 | MAX.chr20.44936022-44936246 |
| 3 | 13324501-13324623 | MAX.chr3.13324501-13324623 |
| 3 | 13324760-13324864 | MAX.chr3.13324760-13324864 |
| 3 | 44039952-44040054 | MAX.chr3.44039952-44040054 |
| 7 | 142494755-142494915 | MAX.chr7.142494755-142494915 |
| 8 | 30769438-30769680 | MAX.chr8.30769438-30769680 |
| 9 | 99983730-99984118 | MAX.chr9.99983730-99984118 |
| 6 | 41606074-41606126 | MDFI |
| 3 | 150804938-150804971 | MED12L |
| 5 | 88185490-88185589 | MEF2C |
| 22 | 39853199-39853295 | MGAT3 |
| 2 | 220416703-220417434 | MIR3132 |
| 6 | 132722283-132722484 | MOXD1 |
| 8 | 72755813-72756349 | MSC |
| 16 | 58497251-58497370 | NDRG4 |
| 19 | 3361105-3361330 | NFIC |
| 17 | 47573986-47574084 | NGFR |
| 7 | 108095348-108095805 | NRCAM |
| 8 | 32406662-32406901 | NRG1 |
| 17 | 8925482-8925838 | NTN1 |
| 15 | 53082447-53083044 | ONECUT1 |
| 8 | 145106742-145106921 | OPLAH |
| 8 | 145106349-145106456 | OPLAH |
| 5 | 76506245-76506578 | PDE8B |
| 11 | 104034769-104034920 | PDGFD |
| 22 | 45405722-45405819 | PHF21B |
| 8 | 79428485-79428684 | PKIA |
| 1 | 150122783-150123157 | PLEKHO1 |
| 1 | 38510915-38511213 | POU3F1 |
| 17 | 56833684-56833978 | PPM1E |
| 20 | 37434246-37434800 | PPP1R16B |
| 14 | 102248062-102248216 | PPP2R5C |
| 14 | 102247525-102247929 | PPP2R5C |
| 16 | 23847825-23848168 | PRKCB |
| 19 | 47778181-47778372 | PRR24 |
| 6 | 163834534-163834925 | QKI |
| 18 | 9708397-9709392 | RAB31 |
| 20 | 4803201-4803703 | RASSF2 |
| 2 | 161263880-161264733 | RBMS1 |
| 6 | 127440413-127441057 | RSPO3 |
| 17 | 26698693-26699117 | SARM1 |
| 8 | 97505964-97506676 | SDC2 |
| 17 | 75369224-75369327 | Septin9 |
| 17 | 75368800-75369056 | Septin9 |
| 10 | 7452746-7452779 | SFMBT2 |
| 10 | 7452885-7452956 | SFMBT2 |
| 10 | 7452029-7452452 | SFMBT2 |
| 10 | 7450242-7450831 | SFMBT2 |
| 10 | 7451097-7451185 | SFMBT2 |
| 14 | 70655516-70655712 | SLC8A3 |
| 5 | 101632152-101632237 | SLCO4C1 |
| 7 | 128829103-128829184 | SMO |
| 11 | 65601167-65601514 | SNX32 |
| 13 | 95363646-95363959 | SOX21 |
| 12 | 24715703-24715776 | SOX5 |
| 12 | 24715012-24715416 | SOX5 |
| 12 | 24716178-24716294 | SOX5 |
| 17 | 70114081-70114176 | SOX9 |
| 7 | 75896637-75896925 | SRRM3 |
| 6 | 166581771-166582044 | T |
| 12 | 65218900-65218994 | TBC1D30 |
| 12 | 65218335-65218778 | TBC1D30 |
| 8 | 67874670-67875083 | TCF24 |
| 18 | 53255390-53255565 | TCF4 |

TABLE 3A-continued

Colorectal Cancer DMRs

| Chromosome | Chromosome Coordinates | Gene Annotation |
|---|---|---|
| 5 | 1294873-1295322 | TERT |
| 21 | 32930226-32930576 | TIAM1 |
| 21 | 32716063-32716545 | TIAM1 |
| 2 | 74741941-74742264 | TLX2 |
| 15 | 83776196-83776373 | TM6SF1 |
| 2 | 135476019-135476390 | TMEM163 |
| 7 | 19156788-19156858 | TWIST1 |
| 1 | 108507609-108507674 | VAV3 |
| 1 | 108507074-108507498 | VAV3 |
| 5 | 82768837-82769031 | VCAN |
| 2 | 175547056-175547390 | WIPF1 |
| 8 | 10873760-10874271 | XKR6 |
| 8 | 10872819-10873619 | XKR6 |
| 10 | 31609049-31609227 | ZEB1 |
| 2 | 145274517-145274600 | ZEB2 |
| 2 | 145274704-145275062 | ZEB2 |
| 19 | 58951402-58951530 | ZNF132 |
| 19 | 54024023-54024436 | ZNF331 |
| 19 | 53661526-53662618 | ZNF347 |
| 19 | 22018452-22018639 | ZNF43 |
| 16 | 88496963-88497197 | ZNF469 |
| 19 | 37407197-37407365 | ZNF568 |
| 19 | 12267378-12267677 | ZNF625 |
| 19 | 12203466-12203641 | ZNF788 |
| 2 | 185463105-185463763 | ZNF804A |
| 19 | 53970869-53971374 | ZNF813 |

TABLE 3B

Colorectal Cancer DMRs Ranked by Area Under the ROC Curve

| Gene Annotation | Chromosome | Chromosome Coordinate | Area under the ROC curve |
|---|---|---|---|
| SFMBT2 | 10 | 7452885-7452956 | 1.0000 |
| LIFR | 5 | 38556357-38556743 | 0.9969 |
| OPLAH | 8 | 145106742-145106921 | 0.9969 |
| CRHR2 | 7 | 30721941-30722028 | 0.9966 |
| AGBL4 | 1 | 49242089-49242514 | 0.9954 |
| ZEB2 | 2 | 145274704-145275062 | 0.9938 |
| ZNF788 | 19 | 12203466-12203641 | 0.9936 |
| SFMBT2 | 10 | 7452746-7452779 | 0.9926 |
| ESR1 | 6 | 152129389-152129636 | 0.9918 |
| ANKRD33B | 5 | 10565042-10565191 | 0.9907 |
| CHST2 | 3 | 142838645-142839023 | 0.9907 |
| FNDC1 | 6 | 159590083-159590220 | 0.9902 |
| ZNF469 | 16 | 88496963-88497197 | 0.9899 |
| AKR1B1 | 7 | 134142981-134143723 | 0.9892 |
| OPLAH | 8 | 145106349-145106456 | 0.9886 |
| MSC | 8 | 72755813-72756349 | 0.9876 |
| KCNK12 | 2 | 47797187-47797452 | 0.9861 |
| MAX.chr10.22541884-22542001 | 10 | 22541884-22542001 | 0.9861 |
| ONECUT1 | 15 | 53082447-53083044 | 0.9861 |
| RASSF2 | 20 | 4803201-4803703 | 0.9861 |
| BHLHE22 | 8 | 65493937-65494105 | 0.9841 |
| ARHGAP20 | 11 | 110582170-110582657 | 0.9837 |
| EYA4 | 6 | 133562485-133562878 | 0.9830 |
| LINGO3 | 19 | 2290273-2290393 | 0.9830 |
| MATK | 19 | 3785828-3786371 | 0.9830 |
| RSPO3 | 6 | 127440413-127441057 | 0.9830 |
| MGAT3 | 22 | 39853199-39853295 | 0.9828 |
| GRASP | 12 | 52400919-52401166 | 0.9814 |
| ZEB2 | 2 | 145274517-145274600 | 0.9806 |
| GSG1L | 16 | 28074472-28074761 | 0.9804 |
| ZNF625 | 19 | 12267378-12267677 | 0.9799 |
| NDRG4 | 16 | 58497251-58497370 | 0.9771 |
| PPP2R5C | 14 | 102247525-102247929 | 0.9771 |
| FLI1 | 11 | 128562780-128563522 | 0.9739 |
| ZEB1 | 10 | 31609049-31609227 | 0.9739 |
| C1QL3 | 10 | 16562465-16562672 | 0.9737 |
| C1orf70 | 1 | 1476065-1476127 | 0.9733 |
| ANKRD13B | 17 | 27940469-27940612 | 0.9721 |
| DAB2IP | 9 | 124461296-124461420 | 0.9721 |
| GALNT14 | 2 | 31360542-31360640 | 0.9721 |
| ATP8A2 | 13 | 25946118-25946206 | 0.9716 |
| CCDC48 | 3 | 128720801-128720885 | 0.9707 |
| LONRF2 | 2 | 100938402-100939005 | 0.9706 |
| LRRC4 | 7 | 127671918-127672318 | 0.9706 |
| PDGFD | 11 | 104034769-104034920 | 0.9706 |
| SFMBT2 | 10 | 7452029-7452452 | 0.9706 |
| SFMBT2 | 10 | 7450242-7450831 | 0.9706 |
| CHST2 | 3 | 142839223-142839576 | 0.9690 |
| MAX.chr7.142494755-142494915 | 7 | 142494755-142494915 | 0.9690 |
| MAX.chr11.123301058-123301255 | 11 | 123301058-123301255 | 0.9673 |

TABLE 3B-continued

Colorectal Cancer DMRs Ranked by Area Under the ROC Curve

| Gene Annotation | Chromosome | Chromosome Coordinate | Area under the ROC curve |
|---|---|---|---|
| SOX9 | 17 | 70114081-70114176 | 0.9665 |
| MAX.chr20.44936022-44936246 | 20 | 44936022-44936246 | 0.9659 |
| TWIST1 | 7 | 19156788-19156858 | 0.9652 |
| ELMO1 | 7 | 37487539-37487623 | 0.9644 |
| NFIC | 19 | 3361105-3361330 | 0.9644 |
| PLEKHO1 | 1 | 150122783-150123157 | 0.9644 |
| POU3F1 | 1 | 38510915-38511213 | 0.9644 |
| NGFR | 17 | 47573986-47574084 | 0.9633 |
| LINGO3 | 19 | 2290645-2290738 | 0.9624 |
| AEBP1 | 7 | 44143993-44144413 | 0.9613 |
| PPP1R16B | 20 | 37434246-37434800 | 0.9598 |
| SFMBT2 | 10 | 7451097-7451185 | 0.9585 |
| SMO | 7 | 128829103-128829184 | 0.9583 |
| FLI1 | 11 | 128563956-128564209 | 0.9575 |
| DTX1 | 12 | 113494586-113494957 | 0.9551 |
| TIAM1 | 21 | 32930226-32930576 | 0.9551 |
| GABBR2 | 9 | 101471421-101471519 | 0.9542 |
| PRKCB | 16 | 23847825-23848168 | 0.9539 |
| RAB31 | 18 | 9708397-9709392 | 0.9536 |
| VAV3 | 1 | 108507074-108507498 | 0.9536 |
| LASS4 | 19 | 8274584-8274671 | 0.9533 |
| ANK1 | 8 | 41754327-41754726 | 0.9526 |
| ANKRD33B | 5 | 10564655-10564807 | 0.9520 |
| SARM1 | 17 | 26698693-26699117 | 0.9520 |
| TM6SF1 | 15 | 83776196-83776373 | 0.9516 |
| ZNF568 | 19 | 37407197-37407365 | 0.9505 |
| C1orf70 | 1 | 1475560-1475650 | 0.9497 |
| ITGA4 | 2 | 182321830-182321983 | 0.9495 |
| GLB1L3 | 11 | 134146132-134146380 | 0.9493 |
| MAX.chr12.8171360-8171769 | 12 | 8171360-8171769 | 0.9489 |
| MAX.chr14.100437680-100437767 | 14 | 100437680-100437767 | 0.9481 |
| ZNF132 | 19 | 58951402-58951530 | 0.9479 |
| BAALC | 8 | 104152806-104153145 | 0.9474 |
| CHST10 | 2 | 101033758-101034005 | 0.9458 |
| IKZF1 | 7 | 50343838-50344453 | 0.9443 |
| MAX.chr2.144694517-144695025 | 2 | 144694517-144695025 | 0.9443 |
| NRG1 | 8 | 32406662-32406901 | 0.9443 |
| AFF3 | 2 | 100721643-100721967 | 0.9412 |
| FBN1 | 15 | 48938056-48938252 | 0.9412 |
| C1QL3 | 10 | 16562866-16563332 | 0.9397 |
| Septin9 | 17 | 75368800-75369056 | 0.9396 |
| MED12L | 3 | 150804938-150804971 | 0.9387 |
| MDFI | 6 | 41606074-41606126 | 0.9381 |
| MAX.chr11.123301366-123301506 | 11 | 123301366-123301506 | 0.9381 |
| C9orf50 | 9 | 132382813-132382909 | 0.9375 |
| ITPKB | 1 | 226925082-226925651 | 0.9365 |
| TIAM1 | 21 | 32716063-32716545 | 0.9350 |
| LTBP4 | 19 | 41119795-41119907 | 0.9342 |
| LOC100131199 | 7 | 140772542-140772873 | 0.9334 |
| TCF24 | 8 | 67874670-67875083 | 0.9334 |
| MAX.chr11.123301853-123301941 | 11 | 123301853-123301941 | 0.9321 |
| SDC2 | 8 | 97505964-97506676 | 0.9319 |
| TERT | 5 | 1294873-1295322 | 0.9319 |
| ELOVL2 | 6 | 11044395-11044834 | 0.9303 |
| GALNT14 | 2 | 31360809-31360992 | 0.9298 |
| Septin9 | 17 | 75369224-75369327 | 0.9289 |
| GLI3 | 7 | 42276418-42277414 | 0.9288 |
| SOX5 | 12 | 24715703-24715776 | 0.9286 |
| BMP6 | 6 | 7727566-7728088 | 0.9272 |
| ELMO1 | 7 | 37487755-37488565 | 0.9257 |
| HIC1 | 17 | 1959348-1959370 | 0.9246 |
| VAV3 | 1 | 108507609-108507674 | 0.9229 |
| ELOVL4 | 6 | 80656845-80657306 | 0.9203 |
| CCDC48 | 3 | 128719995-128720631 | 0.9195 |
| COL23A1 | 5 | 178016833-178017456 | 0.9195 |
| PPM1E | 17 | 56833684-56833978 | 0.9195 |
| PKIA | 8 | 79428485-79428684 | 0.9186 |
| ASCL1 | 12 | 103351885-103352327 | 0.9180 |
| ZNF347 | 19 | 53661526-53662618 | 0.9173 |
| MAX.chr19.22034447-22034696 | 19 | 22034447-22034696 | 0.9164 |
| NRCAM | 7 | 108095348-108095805 | 0.9164 |
| C17orf46 | 17 | 43339242-43339498 | 0.9149 |
| ARHGAP20 | 11 | 110582796-110583345 | 0.9134 |
| SOX5 | 12 | 24716178-24716294 | 0.9134 |

TABLE 3B-continued

Colorectal Cancer DMRs Ranked by Area Under the ROC Curve

| Gene Annotation | Chromosome | Chromosome Coordinate | Area under the ROC curve |
|---|---|---|---|
| TLX2 | 2 | 74741941-74742264 | 0.9133 |
| ZNF43 | 19 | 22018452-22018639 | 0.9131 |
| BVES | 6 | 105584685-105585220 | 0.9118 |
| CBLN2 | 18 | 70211543-70211719 | 0.9102 |
| MAX.chr19.42444999-42445053 | 19 | 42444999-42445053 | 0.9080 |
| BARX1 | 9 | 96715112-96715603 | 0.9071 |
| GRASP | 12 | 52400569-52400726 | 0.9071 |
| PRR24 | 19 | 47778181-47778372 | 0.9040 |
| MAX.chr3.13324501-13324623 | 3 | 13324501-13324623 | 0.9034 |
| MAX.chr11.57250528-57250611 | 11 | 57250528-57250611 | 0.9031 |
| C1QL3 | 10 | 16563667-16563892 | 0.9025 |
| MAX.chr3.13324760-13324864 | 3 | 13324760-13324864 | 0.9003 |
| KRBA1 | 7 | 149411729-149411847 | 0.9002 |
| ADORA2A | 22 | 24820148-24820373 | 0.8957 |
| TCF4 | 18 | 53255390-53255565 | 0.8955 |
| TBC1D30 | 12 | 65218900-65218994 | 0.8948 |
| XKR6 | 8 | 10872819-10873619 | 0.8947 |
| SLC8A3 | 14 | 70655516-70655712 | 0.8922 |
| NTN1 | 17 | 8925482-8925838 | 0.8916 |
| MAX.chr10.22765155-22765223 | 10 | 22765155-22765223 | 0.8916 |
| MAX.chr10.22541502-22541671 | 10 | 22541502-22541671 | 0.8884 |
| MEF2C | 5 | 88185490-88185589 | 0.8870 |
| TBC1D30 | 12 | 65218335-65218778 | 0.8870 |
| MAX.chr9.99983730-99984118 | 9 | 99983730-99984118 | 0.8854 |
| MAX.chr19.22034799-22034887 | 19 | 22034799-22034887 | 0.8839 |
| SOX21 | 13 | 95363646-95363959 | 0.8839 |
| ZNF804A | 2 | 185463105-185463763 | 0.8839 |
| SLCO4C1 | 5 | 101632152-101632237 | 0.8805 |
| ADAM23 | 2 | 207308703-207308890 | 0.8799 |
| TMEM163 | 2 | 135476019-135476390 | 0.8777 |
| PDE8B | 5 | 76506245-76506578 | 0.8769 |
| EHD3 | 2 | 31456804-31457263 | 0.8762 |
| MAX.chr8.30769438-30769680 | 8 | 30769438-30769680 | 0.8762 |
| QKI | 6 | 163834534-163834925 | 0.8762 |
| AKAP12 | 6 | 151561236-151561473 | 0.8754 |
| ADCY1 | 7 | 45613877-45613977 | 0.8731 |
| LBH | 2 | 30455594-30455705 | 0.8731 |
| SNX32 | 11 | 65601167-65601514 | 0.8731 |
| PPP2R5C | 14 | 102248062-102248216 | 0.8721 |
| MAX.chr3.44039952-44040054 | 3 | 44039952-44040054 | 0.8715 |
| RBMS1 | 2 | 161263880-161264733 | 0.8715 |
| ARHGAP20 | 11 | 110581912-110582039 | 0.8684 |
| LIPE | 19 | 42905798-42906349 | 0.8684 |
| SRRM3 | 7 | 75896637-75896925 | 0.8684 |
| CHST2 | 3 | 142838025-142838494 | 0.8669 |
| XKR6 | 8 | 10873760-10874271 | 0.8669 |
| WIPF1 | 2 | 175547056-175547390 | 0.8653 |
| VCAN | 5 | 82768837-82769031 | 0.8628 |
| KIF5C | 2 | 149633039-149633137 | 0.8612 |
| MOXD1 | 6 | 132722283-132722484 | 0.8607 |
| MIR3132 | 2 | 220416703-220417434 | 0.8591 |
| T | 6 | 166581771-166582044 | 0.8591 |
| DPY19L2 | 12 | 64062131-64062443 | 0.8584 |
| LY86-AS1 | 6 | 6546375-6546598 | 0.8560 |
| ZNF331 | 19 | 54024023-54024436 | 0.8545 |
| PHF21B | 22 | 45405722-45405819 | 0.8541 |
| EGR2 | 10 | 64575060-64575283 | 0.8529 |
| ZNF813 | 19 | 53970869-53971374 | 0.8522 |
| CHST11 | 12 | 104850745-104851001 | 0.8514 |
| SOX5 | 12 | 24715012-24715416 | 0.8514 |
| JAKMIP1 | 4 | 6201350-6201560 | 0.8506 |

TABLE 4A

Large Adenoma DMRs

| Chromosome | Chromosome Coordinates | Gene Annotation |
|---|---|---|
| 7 | 45613877-45613977 | ADCY1 |
| 2 | 70994754-70995045 | ADD2 |
| 22 | 24820148-24820373 | ADORA2A |
| 2 | 100721643-100721967 | AFF3 |

TABLE 4A-continued

Large Adenoma DMRs

| Chromosome | Chromosome Coordinates | Gene Annotation |
|---|---|---|
| 1 | 49242089-49242514 | AGBL4 |
| 6 | 151561236-151561473 | AKAP12 |
| 6 | 151561598-151561873 | AKAP12 |
| 7 | 134142981-134143723 | AKR1B1 |
| 8 | 41754327-41754726 | ANK1 |
| 5 | 10564406-10564551 | ANKRD33B |
| 5 | 10564655-10564807 | ANKRD33B |
| 5 | 10565042-10565191 | ANKRD33B |
| 11 | 110582796-110583345 | ARHGAP20 |
| 12 | 103351885-103352327 | ASCL1 |
| 8 | 104152806-104153145 | BAALC |
| 8 | 65494269-65494355 | BHLHE22 |
| 6 | 7727566-7728088 | BMP6 |
| 6 | 105584685-105585220 | BVES |
| 12 | 21680721-21680828 | C12orf39 |
| 12 | 48577334-48577557 | C12orf68 |
| 16 | 4588091-4588817 | C16orf5 |
| 1 | 1475560-1475650 | C1orf70 |
| 1 | 1476065-1476127 | C1orf70 |
| 10 | 16562866-16563332 | C1QL3 |
| 10 | 16563667-16563892 | C1QL3 |
| 10 | 16562465-16562672 | C1QL3 |
| 20 | 3388089-3388291 | C20orf194 |
| 6 | 74019826-74019955 | C6orf147 |
| 9 | 132382813-132382909 | C9orf50 |
| 7 | 44364925-44365359 | CAMK2B |
| 5 | 110559508-110560719 | CAMK4 |
| 3 | 12838197-12838303 | CAND2 |
| 18 | 70211543-70211719 | CBLN2 |
| 6 | 74405903-74406086 | CD109 |
| 12 | 133464655-133464819 | CHFR |
| 11 | 45686306-45686534 | CHST1 |
| 2 | 101033758-101034005 | CHST10 |
| 12 | 104851372-104851465 | CHST11 |
| 12 | 104850745-104851001 | CHST11 |
| 10 | 125852012-125852098 | CHST15 |
| 10 | 125852559-125852792 | CHST15 |
| 10 | 125852905-125853007 | CHST15 |
| 10 | 125851544-125851700 | CHST15 |
| 3 | 142838025-142838494 | CHST2 |
| 3 | 142838645-142839023 | CHST2 |
| 3 | 142839223-142839576 | CHST2 |
| 3 | 139654045-139654299 | CLSTN2 |
| 5 | 178016833-178017456 | COL23A1 |
| 9 | 124461296-124461420 | DAB2IP |
| 3 | 186079767-186080092 | DGKG |
| 1 | 65731412-65731782 | DNAJC6 |
| 2 | 225906664-225906922 | DOCK10 |
| 12 | 64062131-64062443 | DPY19L2 |
| 12 | 113494586-113494957 | DTX1 |
| 2 | 233352345-233352431 | ECEL1 |
| 10 | 64575060-64575283 | EGR2 |
| 2 | 31456804-31457263 | EHD3 |
| 7 | 37487755-37488565 | ELMO1 |
| 6 | 11044395-11044834 | ELOVL2 |
| 6 | 80656845-80657306 | ELOVL4 |
| 6 | 152129389-152129636 | ESR1 |
| 6 | 133562229-133562380 | EYA4 |
| 6 | 133562485-133562878 | EYA4 |
| 7 | 23053043-23053438 | FAM126A |
| 1 | 53098973-53099237 | FAM159A |
| 1 | 206137408-206137475 | FAM72A |
| 1 | 120839339-120839381 | FAM72B |
| 1 | 120838272-120838775 | FAM72B |
| 1 | 120836675-120836768 | FAM72B |
| 1 | 27960931-27961098 | FGR |
| 11 | 128563956-128564209 | FLI1 |
| 11 | 128562780-128563522 | FLI1 |
| 14 | 62584068-62584109 | FLJ43390 |
| 13 | 28674199-28674826 | FLT3 |
| 9 | 101471421-101471519 | GABBR2 |
| 2 | 31360809-31360992 | GALNT14 |
| 17 | 10102237-10102576 | GAS7 |
| 19 | 19006296-19006511 | GDF1 |
| 5 | 179780627-179781188 | GFPT2 |
| 5 | 137610023-137610333 | GFRA3 |
| 11 | 134146132-134146380 | GLB1L3 |
| 7 | 42276418-42277414 | GLI3 |
| 1 | 54204505-54204712 | GLIS1 |
| 12 | 52400919-52401166 | GRASP |
| 10 | 88125930-88126495 | GRID1 |
| 7 | 6570511-6570865 | GRID2IP |
| 16 | 28074472-28074761 | GSG1L |
| 6 | 32632785-32632860 | HLA-DQB1 |
| 15 | 83621302-83621657 | HOMER2 |
| 7 | 50343838-50344453 | IKZF1 |
| 2 | 182321830-182321983 | ITGA4 |
| 21 | 46351838-46352381 | ITGB2 |
| 1 | 226925082-226925651 | ITPKB |
| 4 | 6202051-6202410 | JAKMIP1 |
| 4 | 6201350-6201560 | JAKMIP1 |
| 2 | 47797187-47797452 | KCNK12 |
| 20 | 62103225-62103324 | KCNQ2 |
| 6 | 73972941-73973104 | KHDC1 |
| 2 | 149633039-149633157 | KIF5C |
| 7 | 149411729-149411847 | KRBA1 |
| 19 | 8274360-8274430 | LASS4 |
| 19 | 8274584-8274671 | LASS4 |
| 19 | 2290273-2290393 | LINGO3 |
| 19 | 42905798-42906349 | LIPE |
| 11 | 8284746-8284871 | LMO1 |
| 7 | 140773610-140773855 | LOC100131199 |
| 7 | 140772542-140772873 | LOC100131199 |
| 2 | 100938402-100939005 | LONRF2 |
| 7 | 127671918-127672318 | LRRC4 |
| 19 | 41119795-41119907 | LTBP4 |
| 6 | 6546375-6546599 | LY86-AS1 |
| 11 | 63828346-63828436 | MACROD1 |
| 19 | 3785828-3786371 | MATK |
| 1 | 244012766-244012875 | MAX.chr1.244012766-244012875 |
| 1 | 244013190-244013393 | MAX.chr1.244013190-244013393 |
| 1 | 39269813-39270150 | MAX.chr1.39269813-39270150 |
| 10 | 22541502-22541671 | MAX.chr10.22541502-22541671 |
| 10 | 22541884-22542001 | MAX.chr10.22541884-22542001 |
| 10 | 22765155-22765223 | MAX.chr10.22765155-22765223 |
| 11 | 120435350-120435981 | MAX.chr11.120435350-120435981 |
| 11 | 123301058-123301255 | MAX.chr11.123301058-123301255 |
| 11 | 123301366-123301506 | MAX.chr11.123301366-123301506 |
| 11 | 123301853-123301941 | MAX.chr11.123301853-123301941 |
| 11 | 44749119-44749205 | MAX.chr11.44749119-44749205 |
| 11 | 8040551-8040677 | MAX.chr11.8040551-8040677 |
| 12 | 133484966-133485857 | MAX.chr12.133484966-133485857 |
| 14 | 100437680-100437767 | MAX.chr14.100437680-100437767 |
| 14 | 105400087-105400182 | MAX.chr14.105400087-105400182 |
| 15 | 34806855-34807014 | MAX.chr15.34806855-34807014 |
| 18 | 77558550-77558609 | MAX.chr18.77558550-77558609 |
| 19 | 20959229-20959691 | MAX.chr19.20959229-20959691 |
| 19 | 22034447-22034696 | MAX.chr19.22034447-22034696 |
| 19 | 22034799-22034887 | MAX.chr19.22034799-22034887 |
| 2 | 144694517-144695025 | MAX.chr2.144694517-144695025 |
| 21 | 47063135-47064177 | MAX.chr21.47063135-47064177 |
| 3 | 115231555-115231576 | MAX.chr3.115231555-115231576 |
| 3 | 44039952-44040054 | MAX.chr3.44039952-44040054 |
| 8 | 30769438-30769680 | MAX.chr8.30769438-30769680 |
| 6 | 37664238-37664539 | MDGA1 |
| 5 | 88185490-88185589 | MEF2C |
| 22 | 39853199-39853295 | MGAT3 |
| 17 | 74864552-74864821 | MGAT5B |
| 3 | 154797723-154797909 | MME |
| 6 | 132722283-132722484 | MOXD1 |
| 17 | 8533282-8534168 | MYH10 |
| 11 | 112832731-112832815 | NCAM1 |
| 16 | 58497979-58498250 | NDRG4 |
| 17 | 47573986-47574084 | NGFR |
| 8 | 41503949-41504137 | NKX6-3 |
| 5 | 142784971-142785160 | NR3C1 |
| 7 | 108095348-108095805 | NRCAM |
| 17 | 8925482-8925838 | NTN1 |
| 1 | 107683961-107684314 | NTNG1 |
| 1 | 107683064-107683372 | NTNG1 |

TABLE 4A-continued

Large Adenoma DMRs

| Chromosome | Chromosome Coordinates | Gene Annotation |
|---|---|---|
| 1 | 107684447-107684545 | NTNG1 |
| 3 | 13461109-13461191 | NUP210 |
| 11 | 79150971-79151076 | ODZ4 |
| 15 | 53082447-53083044 | ONECUT1 |
| 8 | 145106742-145106921 | OPLAH |
| 8 | 145106349-145106456 | OPLAH |
| 3 | 142682282-142682813 | PAQR9 |
| 5 | 140855415-140856027 | PCDHGA1 |
| 5 | 76506245-76506578 | PDE8B |
| 11 | 104034769-104034920 | PDGFD |
| 4 | 55099106-55099473 | PDGFRA |
| 1 | 9711854-9711974 | PIK3CD |
| 8 | 79428485-79428684 | PKIA |
| 1 | 150122783-150123157 | PLEKHO1 |
| 1 | 38510915-38511213 | POU3F1 |
| 17 | 56833684-56833978 | PPM1E |
| 14 | 102248062-102248216 | PPP2R5C |
| 14 | 102247525-102247929 | PPP2R5C |
| 5 | 122425730-122425886 | PRDM6 |
| 20 | 47444582-47444776 | PREX1 |
| 16 | 23847825-23848168 | PRKCB |
| 16 | 23846951-23847056 | PRKCB |
| 8 | 30890580-30890912 | PURG |
| 6 | 163834534-163834925 | QKI |
| 6 | 163835376-163835472 | QKI |
| 20 | 4803969-4804077 | RASSF2 |
| 20 | 4803201-4803703 | RASSF2 |
| 18 | 56936593-56936656 | RAX |
| 15 | 93631919-93632242 | RGMA |
| 9 | 77111900-77112005 | RORB |
| 6 | 127440413-127441057 | RSPO3 |
| 17 | 26698693-26699117 | SARM1 |
| 8 | 97505964-97506676 | SDC2 |
| 7 | 3339895-3340903 | SDK1 |
| 19 | 40005836-40005892 | SELV |
| 17 | 75368800-75369056 | Septin9 |
| 22 | 26565137-26565417 | SEZ6L |
| 10 | 7452746-7452779 | SFMBT2 |
| 10 | 7452885-7452956 | SFMBT2 |
| 10 | 7452029-7452452 | SFMBT2 |
| 10 | 7450242-7450831 | SFMBT2 |
| 10 | 7451097-7451185 | SFMBT2 |
| 6 | 118228394-118228979 | SLC35F1 |
| 14 | 70655516-70655712 | SLC8A3 |
| 14 | 70655268-70655368 | SLC8A3 |
| 11 | 65601167-65601514 | SNX32 |
| 13 | 95363646-95363959 | SOX21 |
| 12 | 24715703-24715776 | SOX5 |
| 12 | 24715012-24715416 | SOX5 |
| 12 | 24716178-24716294 | SOX5 |
| 8 | 10587893-10588143 | SOX7 |
| 7 | 75896637-75896925 | SRRM3 |
| 8 | 134583587-134583963 | ST3GAL1 |
| 12 | 65218900-65218994 | TBC1D30 |
| 17 | 45810562-45810819 | TBX21 |
| 8 | 67874670-67875083 | TCF24 |
| 18 | 53255390-53255565 | TCF4 |
| 21 | 32931523-32931688 | TIAM1 |
| 21 | 32930226-32930576 | TIAM1 |
| 15 | 83776196-83776373 | TM6SF1 |
| 2 | 135476019-135476390 | TMEM163 |
| 2 | 39893089-39893224 | TMEM178 |
| 2 | 12857915-12858230 | TRIB2 |
| 7 | 19156788-19156858 | TWIST1 |
| 1 | 213124472-213124778 | VASH2 |
| 1 | 108507609-108507674 | VAV3 |
| 1 | 108507074-108507498 | VAV3 |
| 5 | 82768837-82769031 | VCAN |
| 10 | 17271896-17271978 | VIM |
| 10 | 17270955-17271052 | VIM |
| 13 | 27131683-27131757 | WASF3 |
| 2 | 175547056-175547390 | WIPF1 |
| 1 | 228195339-228195413 | WNT3A |
| 8 | 10873760-10874271 | XKR6 |
| 8 | 10872819-10873619 | XKR6 |
| 10 | 31608798-31608892 | ZEB1 |
| 10 | 31608394-31608690 | ZEB1 |
| 10 | 31609049-31609227 | ZEB1 |
| 19 | 58951402-58951530 | ZNF132 |
| 4 | 332064-332199 | ZNF141 |
| 17 | 16472295-16472694 | ZNF287 |
| 19 | 54024023-54024436 | ZNF331 |
| 19 | 53661526-53662618 | ZNF347 |
| 19 | 22018746-22019004 | ZNF43 |
| 16 | 88496963-88497197 | ZNF469 |
| 19 | 37064200-37064435 | ZNF529 |
| 19 | 37960066-37960505 | ZNF569 |
| 19 | 12267378-12267677 | ZNF625 |
| 19 | 20149796-20149923 | ZNF682 |
| 2 | 185463105-185463763 | ZNF804A |

TABLE 4B

Large Adenoma DMRs Ranked by Area Under the ROC Curve

| Gene Annotation | Chromosome | Chromosome Coordinate | Area under the ROC curve |
|---|---|---|---|
| ADD2 | 2 | 70994754-70995045 | 1.0000 |
| AGBL4 | 1 | 49242089-49242514 | 1.0000 |
| AKAP12 | 6 | 151561598-151561873 | 1.0000 |
| ANKRD33B | 5 | 10565042-10565191 | 1.0000 |
| ASCL1 | 12 | 103351885-103352327 | 1.0000 |
| C1orf70 | 1 | 1475560-1475650 | 1.0000 |
| CHST11 | 12 | 104851372-104851465 | 1.0000 |
| CHST15 | 10 | 125851544-125851700 | 1.0000 |
| DTX1 | 12 | 113494586-113494957 | 1.0000 |
| ECEL1 | 2 | 233352345-233352431 | 1.0000 |
| EYA4 | 6 | 133562485-133562878 | 1.0000 |
| FLI1 | 11 | 128562780-128563522 | 1.0000 |
| FLJ43390 | 14 | 62584068-62584109 | 1.0000 |
| FLT3 | 13 | 28674199-28674862 | 1.0000 |
| GRASP | 12 | 52400919-52401166 | 1.0000 |
| ITGA4 | 2 | 182321830-182321983 | 1.0000 |
| KCNQ2 | 20 | 62103225-62103324 | 1.0000 |
| LOC100131199 | 7 | 140772542-140772873 | 1.0000 |
| LONRF2 | 2 | 100938402-100939005 | 1.0000 |
| MGAT3 | 22 | 39853199-39853295 | 1.0000 |
| OPLAH | 8 | 145106742-145106921 | 1.0000 |
| OPLAH | 8 | 145106349-145106456 | 1.0000 |
| PDE8B | 5 | 76506245-76506578 | 1.0000 |
| PDGFD | 11 | 104034769-104034920 | 1.0000 |
| PKIA | 8 | 79428485-79428684 | 1.0000 |
| POU3F1 | 1 | 38510915-38511213 | 1.0000 |
| QKI | 6 | 163834534-163834925 | 1.0000 |
| RASSF2 | 20 | 4803201-4803703 | 1.0000 |
| RSPO3 | 6 | 127440413-127441057 | 1.0000 |
| SDC2 | 8 | 97505964-97506676 | 1.0000 |
| SFMBT2 | 10 | 7452746-7452779 | 1.0000 |
| SFMBT2 | 10 | 7452029-7452452 | 1.0000 |
| SFMBT2 | 10 | 7450242-7450831 | 1.0000 |
| SOX5 | 12 | 24716178-24716294 | 1.0000 |
| VAV3 | 1 | 108507609-108507674 | 1.0000 |
| VAV3 | 1 | 108507074-108507498 | 1.0000 |
| ZNF132 | 19 | 58951402-58951530 | 1.0000 |
| ADCY1 | 7 | 45613877-45614034 | 0.9984 |
| C1QL3 | 10 | 16562465-16562672 | 0.9984 |
| FLI1 | 11 | 128563956-128564209 | 0.9984 |
| MYH10 | 17 | 8533282-8534168 | 0.9984 |
| NTNG1 | 1 | 107683064-107683372 | 0.9984 |
| ANKRD33B | 5 | 10564655-10564807 | 0.9983 |
| MAX.chr10.22541502-22541671 | 10 | 22541502-22541671 | 0.9982 |
| MAX.chr11.44749119-44749205 | 11 | 44749119-44749205 | 0.9982 |

TABLE 4B-continued

Large Adenoma DMRs Ranked by Area Under the ROC Curve

| Gene Annotation | Chromosome | Chromosome Coordinate | Area under the ROC curve |
|---|---|---|---|
| GALNT14 | 2 | 31360809-31360992 | 0.9980 |
| AKR1B1 | 7 | 134142981-134143723 | 0.9967 |
| CHST2 | 3 | 142839223-142839576 | 0.9967 |
| EYA4 | 6 | 133562229-133562380 | 0.9967 |
| ZNF625 | 19 | 12267378-12267677 | 0.9967 |
| LMO1 | 11 | 8284746-8284871 | 0.9965 |
| ZNF469 | 16 | 88496963-88497197 | 0.9964 |
| ESR1 | 6 | 152129389-152129636 | 0.9951 |
| KCNK12 | 2 | 47797187-47797452 | 0.9951 |
| MAX.chr11.8040551-8040677 | 11 | 8040551-8040677 | 0.9951 |
| MOXD1 | 6 | 132722283-132722484 | 0.9951 |
| PPP2R5C | 14 | 102247525-102247929 | 0.9951 |
| PPP2R5C | 14 | 102248062-102248216 | 0.9949 |
| CHST11 | 12 | 104850745-104851001 | 0.9948 |
| LASS4 | 19 | 8274584-8274671 | 0.9945 |
| GSG1L | 16 | 28074472-28074761 | 0.9935 |
| MAX.chr11.120435350-120435981 | 11 | 120435350-120435981 | 0.9935 |
| XKR6 | 8 | 10872819-10873619 | 0.9935 |
| MAX.chr1.244012766-244012875 | 1 | 244012766-244012875 | 0.9933 |
| DGKG | 3 | 186079767-186080092 | 0.9931 |
| ITGB2 | 21 | 46351838-46352381 | 0.9931 |
| MAX.chr19.22034447-22034696 | 19 | 22034447-22034696 | 0.9926 |
| ZNF347 | 19 | 53661526-53662618 | 0.9921 |
| MAX.chr8.30769438-30769680 | 8 | 30769438-30769680 | 0.9918 |
| SOX5 | 12 | 24715012-24715416 | 0.9918 |
| CHST15 | 10 | 125852905-125853007 | 0.9913 |
| ODZ4 | 11 | 79150971-79151076 | 0.9913 |
| SOX21 | 13 | 95363646-95363959 | 0.9908 |
| SEZ6L | 22 | 26565137-26565417 | 0.9902 |
| GAS7 | 17 | 10102237-10102576 | 0.9899 |
| MAX.chr11.123301853-123301941 | 11 | 123301853-123301941 | 0.9889 |
| ELMO1 | 7 | 37487755-37488565 | 0.9886 |
| VIM | 10 | 17270955-17271052 | 0.9886 |
| WNT3A | 1 | 228195339-228195413 | 0.9886 |
| SLC8A3 | 14 | 70655516-70655712 | 0.9879 |
| PLEKHO1 | 1 | 150122783-150123157 | 0.9869 |
| SLC8A3 | 14 | 70655268-70655368 | 0.9869 |
| ZNF682 | 19 | 20149796-20149923 | 0.9869 |
| ADORA2A | 22 | 24820148-24820373 | 0.9857 |
| ELOVL2 | 6 | 11044395-11044834 | 0.9853 |
| GFRA3 | 5 | 137610023-137610333 | 0.9853 |
| SOX5 | 12 | 24715703-24715776 | 0.9847 |
| EHD3 | 2 | 31456804-31457263 | 0.9837 |
| TMEM163 | 2 | 135476019-135476390 | 0.9837 |
| MAX.chr14.105400087-105400182 | 14 | 105400087-105400182 | 0.9835 |
| MACROD1 | 11 | 63828346-63828436 | 0.9833 |
| ANKRD33B | 5 | 10564406-10564551 | 0.9820 |
| MATK | 19 | 3785828-3786371 | 0.9820 |
| NTNG1 | 1 | 107683961-107684314 | 0.9820 |
| ONECUT1 | 15 | 53082447-53083044 | 0.9820 |
| WIPF1 | 2 | 175547056-175547390 | 0.9820 |
| GRID1 | 10 | 88125930-88126495 | 0.9804 |
| MAX.chr11.123301366-123301506 | 11 | 123301366-123301506 | 0.9804 |
| RASSF2 | 20 | 4803969-4804077 | 0.9804 |
| TCF4 | 18 | 53255390-53255565 | 0.9804 |
| TRIB2 | 2 | 12857915-12858230 | 0.9804 |
| ZNF331 | 19 | 54024023-54024436 | 0.9804 |
| SLC35F1 | 6 | 118228394-118228979 | 0.9794 |
| COL23A1 | 5 | 178016833-178017456 | 0.9788 |
| FAM159A | 1 | 53098973-53099237 | 0.9788 |
| GABBR2 | 9 | 101471421-101471519 | 0.9788 |
| CHST2 | 3 | 142838645-142839023 | 0.9775 |
| MAX.chr19.22034799-22034887 | 19 | 22034799-22034887 | 0.9775 |
| CHST10 | 2 | 101033758-101034005 | 0.9771 |
| GFPT2 | 5 | 179780627-179781188 | 0.9771 |
| IKZF1 | 7 | 50343838-50344453 | 0.9771 |
| PRKCB | 16 | 23847825-23848168 | 0.9766 |
| GRID2IP | 7 | 6570511-6570865 | 0.9758 |
| HOMER2 | 15 | 83621302-83621657 | 0.9758 |
| CHST1 | 11 | 45686306-45686534 | 0.9755 |
| MAX.chr18.77558550-77558609 | 18 | 77558550-77558609 | 0.9753 |
| LINGO3 | 19 | 2290273-2290393 | 0.9740 |
| LASS4 | 19 | 8274360-8274430 | 0.9739 |
| ZEB1 | 10 | 31609049-31609227 | 0.9722 |
| ZNF43 | 19 | 22018746-22019004 | 0.9722 |
| C12orf39 | 12 | 21680721-21680828 | 0.9706 |
| MAX.chr10.22541884-22542001 | 10 | 22541884-22542001 | 0.9706 |
| MAX.chr11.123301058-123301255 | 11 | 123301058-123301255 | 0.9706 |
| VIM | 10 | 17271896-17271978 | 0.9699 |
| AKAP12 | 6 | 151561236-151561473 | 0.9690 |
| C16orf5 | 16 | 4588091-4588817 | 0.9690 |
| RORB | 9 | 77111900-77112005 | 0.9690 |
| NRCAM | 7 | 108095348-108095805 | 0.9689 |
| ELOVL4 | 6 | 80656845-80657306 | 0.9683 |
| CHST2 | 3 | 142838025-142838494 | 0.9673 |
| ITPKB | 1 | 226925082-226925651 | 0.9673 |
| PIK3CD | 1 | 9711854-9711974 | 0.9673 |
| SARM1 | 17 | 26698693-26699117 | 0.9673 |
| GDF1 | 19 | 19006296-19006511 | 0.9671 |
| XKR6 | 8 | 10873760-10874271 | 0.9671 |
| C9orf50 | 9 | 132382813-132382909 | 0.9659 |
| MAX.chr12.133484966-133485857 | 12 | 133484966-133485857 | 0.9657 |
| PURG | 8 | 30890580-30890912 | 0.9643 |
| AFF3 | 2 | 100721643-100721967 | 0.9641 |
| PDGFRA | 4 | 55099106-55099473 | 0.9641 |
| MAX.chr3.44039952-44040054 | 3 | 44039952-44040054 | 0.9637 |
| TWIST1 | 7 | 19156788-19156858 | 0.9632 |
| MEF2C | 5 | 88185490-88185589 | 0.9608 |
| VCAN | 5 | 82768837-82769031 | 0.9602 |
| NCAM1 | 11 | 112832731-112832815 | 0.9600 |
| CAMK4 | 5 | 110559508-110560719 | 0.9592 |
| TBC1D30 | 12 | 65218900-65218994 | 0.9587 |
| BMP6 | 6 | 7727566-7728088 | 0.9585 |
| BAALC | 8 | 104152806-104153145 | 0.9575 |
| GLB1L3 | 11 | 134146132-134146380 | 0.9575 |
| KRBA1 | 7 | 149411729-149411847 | 0.9569 |
| TCF24 | 8 | 67874670-67875083 | 0.9550 |
| NTN1 | 17 | 8925482-8925838 | 0.9542 |
| CAMK2B | 7 | 44364925-44365359 | 0.9516 |
| MAX.chr2.144694517-144695025 | 2 | 144694517-144695025 | 0.9510 |
| SDK1 | 7 | 3339895-3340903 | 0.9510 |
| SRRM3 | 7 | 75896637-75896925 | 0.9498 |
| CLSTN2 | 3 | 139654045-139654299 | 0.9493 |
| SELV | 19 | 40005836-40005892 | 0.9487 |
| LY86-AS1 | 6 | 6546375-6546598 | 0.9477 |
| PPM1E | 17 | 56833684-56833978 | 0.9477 |
| TM6SF1 | 15 | 83776196-83776373 | 0.9462 |
| MAX.chr1.244013190-244013393 | 1 | 244013190-244013393 | 0.9461 |
| MAX.chr1.39269813-39270150 | 1 | 39269813-39270150 | 0.9461 |
| MAX.chr14.100437680-100437767 | 14 | 100437680-100437767 | 0.9446 |
| EGR2 | 10 | 64575060-64575283 | 0.9444 |
| SOX7 | 8 | 10587893-10588143 | 0.9428 |
| LRRC4 | 7 | 127671918-127672318 | 0.9395 |
| RGMA | 15 | 93631919-93632242 | 0.9395 |
| ZNF804A | 2 | 185463105-185463763 | 0.9395 |
| C1QL3 | 10 | 16562866-16563332 | 0.9373 |
| SFMBT2 | 10 | 7451097-7451185 | 0.9366 |
| CHFR | 12 | 133464655-133464819 | 0.9360 |

TABLE 4B-continued

Large Adenoma DMRs Ranked by Area Under the ROC Curve

| Gene Annotation | Chromosome | Chromosome Coordinate | Area under the ROC curve |
|---|---|---|---|
| JAKMIP1 | 4 | 6201350-6201560 | 0.9360 |
| ANK1 | 8 | 41754327-41754726 | 0.9346 |
| FAM126A | 7 | 23053043-23053438 | 0.9346 |
| SFMBT2 | 10 | 7452885-7452956 | 0.9338 |
| MME | 3 | 154797723-154797909 | 0.9329 |
| BHLHE22 | 8 | 65494269-65494355 | 0.9323 |
| DPY19L2 | 12 | 64062131-64062443 | 0.9314 |
| VASH2 | 1 | 213124472-213124778 | 0.9302 |
| PREX1 | 20 | 47444582-47444776 | 0.9286 |
| ARHGAP20 | 11 | 110582796-110583345 | 0.9248 |
| MAX.chr10.22765155-22765223 | 10 | 22765155-22765223 | 0.9242 |
| ZNF141 | 4 | 332064-332199 | 0.9221 |
| DNAJC6 | 1 | 65731412-65731782 | 0.9216 |
| PCDHGA1 | 5 | 140855415-140856027 | 0.9216 |
| QKI | 6 | 163835376-163835472 | 0.9213 |
| MAX.chr3.115231555-115231576 | 3 | 115231555-115231576 | 0.9199 |
| GLIS1 | 1 | 54204505-54204712 | 0.9178 |
| ZEB1 | 10 | 31608394-31608690 | 0.9150 |
| BVES | 6 | 105584685-105585220 | 0.9134 |
| LOC100131199 | 7 | 140773610-140773855 | 0.9134 |
| PAQR9 | 3 | 142682282-142682813 | 0.9134 |
| CD109 | 6 | 74405903-74406086 | 0.9126 |
| RAX | 18 | 56936593-56936656 | 0.9091 |
| C12orf68 | 12 | 48577334-48577715 | 0.9069 |
| SNX32 | 11 | 65601167-65601514 | 0.9069 |
| HLA-DQB1 | 6 | 32632785-32632860 | 0.9058 |
| PRKCB | 16 | 23846951-23847056 | 0.9053 |
| GLI3 | 7 | 42276418-42277414 | 0.9036 |
| Septin9 | 17 | 75368800-75369018 | 0.9031 |
| FAM72A | 1 | 206137408-206137473 | 0.9016 |
| NDRG4 | 16 | 58497979-58498250 | 0.9003 |
| FAM72B | 1 | 120838272-120838775 | 0.8995 |
| KIF5C | 2 | 149633039-149633137 | 0.8990 |
| JAKMIP1 | 4 | 6202051-6202410 | 0.8989 |
| CHST15 | 10 | 125852559-125852792 | 0.8989 |
| MDGA1 | 6 | 37664238-37664539 | 0.8987 |
| NGFR | 17 | 47573946-47574064 | 0.8981 |
| ZEB1 | 10 | 31608798-31608892 | 0.8979 |
| ZNF529 | 19 | 37064200-37064435 | 0.8979 |
| ZNF287 | 17 | 16472295-16472694 | 0.8962 |
| C1orf70 | 1 | 1476065-1476127 | 0.8962 |
| C20orf194 | 20 | 3388089-3388291 | 0.8932 |
| TIAM1 | 21 | 32930226-32930576 | 0.8910 |
| NR3C1 | 5 | 142784971-142785160 | 0.8895 |
| CBLN2 | 18 | 70211543-70211759 | 0.8873 |
| NKX6-3 | 8 | 41503949-41504137 | 0.8858 |
| TMEM178 | 2 | 39893089-39893224 | 0.8856 |
| KHDC1 | 6 | 73972941-73973104 | 0.8845 |
| PRDM6 | 5 | 122425730-122425886 | 0.8824 |
| ST3GAL1 | 8 | 134583587-134583963 | 0.8824 |
| FAM72B | 1 | 120839339-120839381 | 0.8815 |
| DAB2IP | 9 | 124461296-124461420 | 0.8787 |
| CHST15 | 10 | 125852012-125852098 | 0.8780 |
| C6orf147 | 6 | 74019826-74019955 | 0.8775 |
| MAX.chr21.47063135-47064177 | 21 | 47063135-47064177 | 0.8775 |
| TIAM1 | 21 | 32931523-32931688 | 0.8772 |
| C1QL3 | 10 | 16563667-16563892 | 0.8758 |
| NUP210 | 3 | 13461109-13461191 | 0.8755 |
| FAM72B | 1 | 120836675-120836768 | 0.8736 |
| MAX.chr15.34806855-34807014 | 15 | 34806855-34807014 | 0.8722 |
| CAND2 | 3 | 12838197-12838303 | 0.8719 |
| TBX21 | 17 | 45810562-45810819 | 0.8702 |
| MGAT5B | 17 | 74864552-74864821 | 0.8685 |
| ZNF569 | 19 | 37960066-37960505 | 0.8676 |
| NTNG1 | 1 | 107684447-107684545 | 0.8672 |
| WASF3 | 13 | 27131683-27131757 | 0.8647 |
| LIPE | 19 | 42905798-42906349 | 0.8644 |
| DOCK10 | 2 | 225906664-225906922 | 0.8578 |
| LTBP4 | 19 | 41119795-41119907 | 0.8546 |
| MAX.chr19.20959229-20959691 | 19 | 20959229-20959691 | 0.8521 |
| FGR | 1 | 27960931-27961018 | 0.8513 |

TABLE 5A

Sessile Serrated Polyps (SSP) DMR

| Chromosome | Chromosome Coordinates | Gene Annotation |
|---|---|---|
| 5 | 10564655-10564710 | ANKRD33B |
| 12 | 103351885-103351983 | ASCL1 |
| 1 | 203598574-203598800 | ATP2B4 |
| 6 | 91005003-91005091 | BACH2 |
| 6 | 7727026-7727129 | BMP6 |
| 6 | 105584890-105584983 | BVES |
| 10 | 21784521-21784567 | C10orf114 |
| 1 | 226737152-226737231 | C1orf95 |
| 5 | 110559571-110559638 | CAMK4 |
| 2 | 56411545-56411640 | CCDC85A |
| 1 | 158150837-158150885 | CD1D |
| 1 | 158151102-158151205 | CD1D |
| 10 | 90967004-90967028 | CH25H |
| 2 | 101033768-101033858 | CHST10 |
| 12 | 104850745-104850879 | CHST11 |
| 3 | 142838194-142838411 | CHST2 |
| 9 | 34590231-34590344 | CNTFR |
| 12 | 49484149-49484231 | DHH |
| 15 | 30484732-30484813 | DKFZP434L187 |
| 1 | 65731412-65731530 | DNAJC6 |
| 2 | 225906639-225906763 | DOCK10 |
| 2 | 225907515-225907632 | DOCK10 |
| 2 | 73520956-73520964 | EGR4 |
| 6 | 80656889-80656974 | ELOVL4 |
| 6 | 80657208-80657306 | ELOVL4 |
| 5 | 111754713-111754810 | EPB41L4A |
| 3 | 96532270-96532344 | EPHA6 |
| 7 | 23053937-23054066 | FAM126A |
| 11 | 125365196-125365327 | FEZ1 |
| 13 | 22243643-22243727 | FGF9 |
| 7 | 90894876-90894960 | FZD1 |
| 17 | 42907793-42907827 | GJC1 |
| 3 | 179169408-179169505 | GNB4 |
| 1 | 101005577-101005661 | GPR88 |
| 1 | 53068071-53068182 | GPX7 |
| 7 | 6570755-6570845 | GRID2IP |
| 16 | 10275378-10275472 | GRIN2A |
| 17 | 14205388-14205498 | HS3ST3B1 |
| 7 | 23509037-23509225 | IGF2BP3 |
| 6 | 39281409-39281488 | KCNK17 |
| 15 | 79724426-79724525 | KIAA1024 |
| 2 | 208031024-208031104 | KLF7 |
| 2 | 208031731-208031826 | KLF7 |
| 2 | 30454421-30454492 | LBH |
| 2 | 30454871-30454977 | LBH |
| 2 | 74726179-74726265 | LBX2 |
| 5 | 87970308-87970374 | LOC645323 |
| 5 | 87970772-87970894 | LOC645323 |
| 2 | 170220089-170220148 | LRP2 |
| 12 | 40618617-40618655 | LRRK2 |
| 1 | 25944147-25944152 | MAN1C1 |
| 11 | 123301366-123301387 | MAX.chr11.123301366-123301387 |
| 17 | 45867397-45867662 | MAX.chr17.45867397-45867662 |
| 19 | 55963254-55963329 | MAX.chr19.55963254-55963329 |
| 2 | 127783352-127783403 | MAX.chr2.127783352-127783403 |

TABLE 5A-continued

Sessile Serrated Polyps (SSP) DMR

| Chromosome | Chromosome Coordinates | Gene Annotation |
|---|---|---|
| 2 | 96192422-96192521 | MAX.chr2.96192422-96192521 |
| 20 | 1783778-1783841 | MAX.chr20.1783778-1783841 |
| 22 | 42310340-42310438 | MAX.chr22.42310340-42310438 |
| 3 | 43935668-43935753 | MAX.chr3.43935668-43935753 |
| 4 | 186049639-186049660 | MAX.chr4.186049639-186049660 |
| 6 | 114664537-114664631 | MAX.chr6.114664537-114664631 |
| 7 | 127807622-127807693 | MAX.chr7.127807622-127807693 |
| 7 | 149745500-149745592 | MAX.chr7.149745500-149745592 |
| 9 | 114074-114160 | MAX.chr9.114074-114160 |
| 9 | 114354-114435 | MAX.chr9.114354-114435 |
| 9 | 99983903-99984118 | MAX.chr9.99983903-99984118 |
| 6 | 37664654-37664664 | MDGA1 |
| 15 | 66546092-66546108 | MEGF11 |
| 15 | 82339716-82339790 | MEX3B |
| 11 | 30607877-30607973 | MPPED2 |
| 4 | 113437673-113437953 | NEUROG2 |
| 1 | 153651840-153651933 | NPR1 |
| 5 | 142785023-142785050 | NR3C1 |
| 8 | 32406662-32406739 | NRG1 |
| 1 | 40137384-40137471 | NT5C1A |
| 1 | 107684212-107684314 | NTNG1 |
| 1 | 107683064-107683130 | NTNG1 |
| 5 | 140855796-140855883 | PCDHGA1 |

TABLE 5A-continued

Sessile Serrated Polyps (SSP) DMR

| Chromosome | Chromosome Coordinates | Gene Annotation |
|---|---|---|
| 1 | 9711931-9711974 | PIK3CD |
| 2 | 198669944-198670044 | PLCL1 |
| 1 | 150122951-150122989 | PLEKHO1 |
| 14 | 102247811-102247881 | PPP2R5C |
| 9 | 33677215-33677313 | PTENP1 |
| 18 | 9708795-9708891 | RAB31 |
| 18 | 9708515-9708598 | RAB31 |
| 1 | 167599730-167599772 | RCSD1 |
| 1 | 44872395-44872487 | RNF220 |
| 9 | 94712910-94712961 | ROR2 |
| 9 | 77111911-77112005 | RORB |
| 17 | 1928103-1928210 | RTN4RL1 |
| 1 | 101702045-101702063 | S1PR1 |
| 1 | 860904-860978 | SAMD11 |
| 22 | 42949849-42949919 | SERHL2 |
| 10 | 7450571-7450659 | SFMBT2 |
| 1 | 220101492-220101587 | SLC30A10 |
| 6 | 118228394-118228493 | SLC35F1 |
| 12 | 24715012-24715060 | SOX5 |
| 12 | 24715174-24715255 | SOX5 |
| 10 | 73847865-73847982 | SPOCK2 |
| 18 | 52989026-52989191 | TCF4 |
| 13 | 43148769-43148861 | TNFSF11 |
| 9 | 135285696-135285788 | TTF1 |
| 6 | 149069140-149069222 | UST |
| 3 | 55521770-55521861 | WNT5A |
| 10 | 31608625-31608690 | ZEB1 |
| 19 | 58666209-58666308 | ZNF329 |
| 19 | 20149832-20149923 | ZNF682 |
| 19 | 53073640-53073729 | ZNF701 |
| 7 | 6655558-6655640 | ZNF853 |

TABLE 5B

Sessile Serrated Polyps (SSP) DMR Ranked by Area Under the ROC Curve

| Gene Annotation | Chromosome | Chromosome Coordinate | Area under the ROC curve |
|---|---|---|---|
| CAMK4 | 5 | 110559571-110559638 | 1.0000 |
| FGF9 | 13 | 22243643-22243727 | 1.0000 |
| GJC1 | 17 | 42907793-42907827 | 1.0000 |
| GPX7 | 1 | 53068071-53068182 | 1.0000 |
| GRIN2A | 16 | 10275378-10275472 | 1.0000 |
| IGF2BP3 | 7 | 23509037-23509225 | 1.0000 |
| MAX.chr19.55963254-55963329 | 19 | 55963254-55963329 | 1.0000 |
| MAX.chr2.127783352-127783403 | 2 | 127783352-127783403 | 1.0000 |
| MAX.chr4.186049639-186049660 | 4 | 186049639-186049660 | 1.0000 |
| NRG1 | 8 | 32406662-32406739 | 1.0000 |
| NTNG1 | 1 | 107684212-107684314 | 1.0000 |
| PIK3CD | 1 | 9711931-9711974 | 1.0000 |
| PTENP1 | 9 | 33677215-33677313 | 1.0000 |
| RAB31 | 18 | 9708795-9708891 | 1.0000 |
| RNF220 | 1 | 44872395-44872487 | 1.0000 |
| SLC30A10 | 1 | 220101492-220101587 | 1.0000 |
| ZNF853 | 7 | 6655558-6655640 | 1.0000 |
| LBH | 2 | 30454871-30454977 | 0.9967 |
| DOCK10 | 2 | 225906664-225906763 | 0.9958 |
| MEX3B | 15 | 82339716-82339790 | 0.9951 |
| PCDHGA1 | 5 | 140855796-140855883 | 0.9926 |
| FZD1 | 7 | 90894876-90894960 | 0.9916 |
| GNB4 | 3 | 179169408-179169505 | 0.9916 |
| MAN1C1 | 1 | 25944147-25944152 | 0.9916 |
| ZNF701 | 19 | 53073640-53073729 | 0.9916 |
| DKFZP434L187 | 15 | 30484732-30484813 | 0.9902 |
| RTN4RL1 | 17 | 1928103-1928210 | 0.9902 |
| MAX.chr20.1783778-1783841 | 20 | 1783778-1783841 | 0.9890 |
| SPOCK2 | 10 | 73847865-73847982 | 0.9853 |
| MAX.chr7.149745500-149745592 | 7 | 149745500-149745592 | 0.9804 |
| HS3ST3B1 | 17 | 14205388-14205498 | 0.9748 |

TABLE 5B-continued

Sessile Serrated Polyps (SSP) DMR Ranked by Area Under the ROC Curve

| Gene Annotation | Chromosome | Chromosome Coordinate | Area under the ROC curve |
|---|---|---|---|
| LRP2 | 2 | 170220089-170220148 | 0.9748 |
| MAX.chr9.114354-114435 | 9 | 114354-114435 | 0.9748 |
| ELOVL4 | 6 | 80656889-80656974 | 0.9706 |
| ELOVL4 | 6 | 80657208-80657306 | 0.9706 |
| MPPED2 | 11 | 30607877-30607973 | 0.9706 |
| MAX.chr17.45867397-45867662 | 17 | 45867397-45867662 | 0.9664 |
| CD1D | 1 | 158150837-158150885 | 0.9618 |
| ATP2B4 | 1 | 203598574-203598800 | 0.9559 |
| C10orf114 | 10 | 21784521-21784567 | 0.9496 |
| KCNK17 | 6 | 39281409-39281488 | 0.9485 |
| FEZ1 | 11 | 125365196-125365327 | 0.9429 |
| PLCL1 | 2 | 198669944-198670044 | 0.9363 |
| CD1D | 1 | 158151102-158151205 | 0.9314 |
| NT5C1A | 1 | 40137384-40137471 | 0.9286 |
| MAX.chr9.99983903-99984118 | 9 | 99983903-99984118 | 0.9191 |
| GPR88 | 1 | 101005577-101005661 | 0.9069 |
| RAB31 | 18 | 9708515-9708598 | 0.9069 |
| NR3C1 | 5 | 142785023-142785050 | 0.9048 |
| S1PR1 | 1 | 101702045-101702063 | 0.9044 |
| SOX5 | 12 | 24715012-24715060 | 0.9044 |
| EPB41L4A | 5 | 111754713-111754810 | 0.9034 |
| LOC645323 | 5 | 87970772-87970894 | 0.9034 |
| CHST11 | 12 | 104850745-104850879 | 0.8971 |
| ROR2 | 9 | 94712910-94712961 | 0.8946 |
| MAX.chr22.42310340-42310438 | 22 | 42310340-42310438 | 0.8918 |
| RORB | 9 | 77111911-77112005 | 0.8905 |
| ZEB1 | 10 | 31608625-31608690 | 0.8897 |
| NEUROG2 | 4 | 113437673-113437953 | 0.8856 |
| TCF4 | 18 | 52989026-52989191 | 0.8807 |
| MAX.chr3.43935668-43935753 | 3 | 43935668-43935753 | 0.8750 |
| KLF7 | 2 | 208031731-208031826 | 0.8739 |
| ZNF682 | 19 | 20149832-20149923 | 0.8739 |
| DOCK10 | 2 | 225907515-225907632 | 0.8732 |
| MDGA1 | 6 | 37664654-37664664 | 0.8725 |
| LBH | 2 | 30454421-30454492 | 0.8718 |
| WNT5A | 3 | 55521770-55521861 | 0.8718 |
| BVES | 6 | 105584890-105584983 | 0.8706 |
| SAMD11 | 1 | 860904-860978 | 0.8706 |
| MEGF11 | 15 | 66546092-66546108 | 0.8701 |
| LRRK2 | 12 | 40618617-40618655 | 0.8697 |
| BACH2 | 6 | 91005003-91005091 | 0.8687 |
| CHST10 | 2 | 101033768-101033858 | 0.8676 |
| CHST2 | 3 | 142838194-142838411 | 0.8676 |
| MAX.chr9.114074-114160 | 9 | 114074-114160 | 0.8664 |
| EGR4 | 2 | 73520956-73520964 | 0.8627 |
| NTNG1 | 1 | 107683064-107683130 | 0.8613 |
| TTF1 | 9 | 135285696-135285788 | 0.8613 |
| SOX5 | 12 | 24715174-24715255 | 0.8611 |
| ASCL1 | 12 | 103351885-103351983 | 0.8603 |
| KLF7 | 2 | 208031024-208031104 | 0.8600 |
| CNTFR | 9 | 34590231-34590344 | 0.8592 |
| MAX.chr6.114664537-114664631 | 6 | 114664537-114664631 | 0.8592 |
| SFMBT2 | 10 | 7450571-7450659 | 0.8585 |
| TNFSF11 | 13 | 43148769-43148861 | 0.8571 |
| DNAJC6 | 1 | 65731412-65731530 | 0.8550 |
| GRID2IP | 7 | 6570755-6570845 | 0.8550 |
| BMP6 | 6 | 7727026-7727129 | 0.8474 |
| MAX.chr11.123301366-123301387 | 11 | 123301366-123301387 | 0.8471 |
| PPP2R5C | 14 | 102247811-102247881 | 0.8466 |
| SERHL2 | 22 | 42949849-42949919 | 0.8464 |
| RCSD1 | 1 | 167599730-167599772 | 0.8456 |
| MAX.chr2.96192422-96192521 | 2 | 96192422-96192521 | 0.8431 |
| ANKRD33B | 5 | 10564655-10564710 | 0.8407 |
| NPR1 | 1 | 153651840-153651933 | 0.8384 |
| EPHA6 | 3 | 96532270-96532344 | 0.8267 |
| FAM126A | 7 | 23053937-23054066 | 0.8262 |
| CH25H | 10 | 90967004-90967028 | 0.8235 |
| KIAA1024 | 15 | 79724426-79724525 | 0.8235 |
| LOC645323 | 5 | 87970308-87970374 | 0.8235 |
| ZNF329 | 19 | 58666209-58666308 | 0.8224 |
| UST | 6 | 149069140-149069222 | 0.8199 |
| CCDC85A | 2 | 56411545-56411640 | 0.8193 |

TABLE 5B-continued

Sessile Serrated Polyps (SSP) DMR Ranked by Area Under the ROC Curve

| Gene Annotation | Chromosome | Chromosome Coordinate | Area under the ROC curve |
|---|---|---|---|
| PLEKHO1 | 1 | 150122951-150122989 | 0.8176 |
| SLC35F1 | 6 | 118228394-118228493 | 0.8082 |
| LBX2 | 2 | 74726179-74726265 | 0.8059 |
| DHH | 12 | 49484149-49484231 | 0.8046 |
| MAX.chr7.127807622-127807693 | 7 | 127807622-127807693 | 0.8007 |
| C1orf95 | 1 | 226737152-226737231 | 0.8000 |

Example 3

This example demonstrates NDRG4, BMP3, OPLAH, FLI1, PDGFD, CHST_7889, SFMBT2_895, SFMBT2_896, SFMBT2_897, CHST2_7890, VAV3, and DTX1 as effective markers for detecting colorectal cancer within stool samples.

Forward and reverse primer and probe sequences for NDRG4, BMP3, OPLAH, FLI1, PDGFD, CHST_7889, SFMBT2_895, SFMBT2_896, SFMBT2_897, CHST2_7890, VAV3, and DTX1 are provided in Table 6A.

Table 6B provides information regarding the methylated marker, chromosome and DMR genomic coordinates provided in Table 6A.

Capture probes for each marker were designed to have a melting temperature of 75-80° C. and lengths between 25-35 bases (see, Table 6C). Additionally, the capture probe hybridizing region was selected to be within the post-bisulfite QuARTS footprint. Table 6C provides the methylation marker and respective capture probe sequences.

TABLE 6A

Forward Primer, Probe, Reverse Primer Sequences for Markers Utilized in Example 3

| Methylation Marker | Forward Primer | Probe Sequence | Reverse Primer |
|---|---|---|---|
| VAV3 | TCGGAGTCGAGTTTAGCGC (SEQ ID NO: 54) | CCACGGACG-CGGCGTTCGC GA/3C6/ (SEQ ID NO: 55) | CGAAATCGAAAAAACAAAAAC CGC (SEQ ID NO: 56) |
| CHST_7889 | CGAGTTCGGTAGTTGTACG TAGA (SEQ ID NO: 57) | CGCCGAGG-TCGTCGATACC G/3C6/ (SEQ ID NO: 58) | CGAAATACGAACGCGAAATCT AAAACT (SEQ ID NO: 59) |
| SFMBT2_897 | GTcGTcGTTcGAGAGGGTA (SEQ ID NO: 60) | CCACGGACG-ATCGGTTTCG TT/3C6/ (SEQ ID NO: 61) | CGAACAAAAACGAACGAACGA A (SEQ ID NO: 62) |
| SFMBT2_896 | GCGTTTAGGTTGGTCGGAG A (Version1) (SEQ ID NO: 63) GCGTTTAGGTTGGTCGGAG (Version 2) (SEQ ID NO: 90) | CGCCGAGG-CTACGAACCGA A/3C6/ (Version 1) (SEQ ID NO: 64) CGCCGAGGCCGAAAAACTA C/3C6/ (Version 2) (SEQ ID NO: 91) | CCTAACCAACGCACTCAACC (Version 1) (SEQ ID NO: 65) ACGCACTCAACCTACGAAC (Version 2) (SEQ ID NO: 92) |
| SFMBT2_895 | TTAGCGAcGTAGTcGTcGT TG (Version 1) (SEQ ID NO: 66) GCGACGTAGTCGTCGTTG T (Version 2) (SEQ ID NO: 93) | CCACGGACG-CGAAAACGCG AA/3C6/ (Version 1) (SEQ ID NO: 67) CCACGGACGGAAAACGCGAA A/3C6/ (Version 2) (SEQ ID NO: 94) | CCCAACGCGAAAAAAACGC (Version 1) (SEQ ID NO: 68) CCAACGCGAAAAAAACGCG (Version 2) (SEQ ID NO: 95) |
| CHST2_7890 | GTATAGCGCGATTTCGTAG cG (SEQ ID NO: 69) | CGCCGAGG-CGAACATCCTC C/3C6/ (SEQ ID NO: 70) | AATTACCTACGCTATCCGCCC (SEQ ID NO: 71) |
| OPLAH | cGTcGcGTTTTTcGGTTAT ACG (SEQ ID NO: 72) | CCACGGACG-GCACCGTAAA AC/3C6/ (SEQ ID NO: 73) | CGCGAAAACTAAAAAACCGCG (SEQ ID NO: 74) |
| PDGFD | AAACGTTAATTTGTTGTTT GTTTCGTT (Version 1) (SEQ ID NO: 75) GCGAATAAATAAACGTTAA TTTGTTGTTTGTTTCG (Version 2) (SEQ ID NO: 96) | ACTTTCCGAACGCGTATAAA TACC (Version 1) (SEQ ID NO: 76) CCACGGACGCGCACTTCCTT A/3C6/ (Version 2) (SEQ ID NO: 97) | GCGAATAAATAAACGTTAATT TGTTGTTTGTTTCG (Version 1) (SEQ ID NO: 77) ACTTTCCGAACGCGTATAAAT ACC (Version 2) (SEQ ID NO: 98) |

TABLE 6A-continued

Forward Primer, Probe, Reverse Primer Sequences
for Markers Utilized in Example 3

| Methylation Marker | Forward Primer | Probe Sequence | Reverse Primer |
|---|---|---|---|
| FLI1 | GTTGcGAGGTTAGGTTGTAATCG (SEQ ID NO: 78) | CGCCGAGG-CGTCCATTTAAC/3C6/ (SEQ ID NO: 79) | CGCCGCTTACCTTAATAATCCC (SEQ ID NO: 80) |
| DTX1 | GAGTCGCGGTTTCGTTTTC (SEQ ID NO: 81) | CGCCGAGG-CGCGTTCGTTTT/3C6/ (SEQ ID NO: 82) | GACGCGACGACCGAAAAAC (SEQ ID NO: 83) |
| NDRG4 | CGGTTTTCGTTCGTTTTTTCG (SEQ ID NO: 84) | CCACGGACGGTTCGTTTATCG/3C6/ (SEQ ID NO: 85) | CCGCCTTCTACGCGACTA (SEQ ID NO: 86) |
| BMP3 | GTTTAATTTTCGGTTTCGTCGTC (SEQ ID NO: 87) | CGCCGAGGCGGTTTTTTGCG/3C6/ (SEQ ID NO: 88) | CGCTACGAAACACTCCGA (SEQ ID NO: 89) |

TABLE 6B

Methylated marker, chromosome and DMR genomic coordinates.

| Methylated marker | Chromosome | DMR Genomic Coordinates |
|---|---|---|
| BMP3 | 4 | 81031173-81031262 |
| NDRG4 | 16 | 58463478-58463588 |
| VAV3 | 1 | 107964966-107965057 |
| CHST2_7889 | 3 | 143119424-143119583 |
| SFMBT2_897 | 10 | 7410903-7411014 |
| SFMBT2_896 | 10 | 7410764-7410837 |
| SFMBT2_895 | 10 | 7410331-7410490 |
| CHST2_7890 | 3 | 143119999-143120158 |
| OPLAH | 8 | 144051847-144052006 |
| PDGFD | 11 | 104164082-104164186 |
| FLI1 | 11 | 128694158-128694317 |
| DTX1 | 12 | 113056762-113056895 |

TABLE 6C

Methylation marker and respective capture probe sequences.

| Methylation Marker | Capture Probe Sequence |
|---|---|
| VAV3 | /5AmMC6/GATCGAGGGAGCAGGAGCCGCGGCTGACGGGTCGCG (SEQ ID NO: 99) |
| CHST2_7889 | /5AmMC6/CGGTGCCGAGAGCTGCCAGAGAGTTGGATTCTGCG (SEQ ID NO: 100) |
| SFMBT2_897 | /5AmMC6/GCGAGCGGGCAAGGGCGGGCGAGC (SEQ ID NO: 101) |
| SFMBT2_896 | /5AmMC6/ACCTGCGGGCCGAAGGGCTGCTCTCCGG (SEQ ID NO: 102) |
| SFMBT2_895 | /5AmMC6/AGGAGACGCGGGAGCGCGGGGTAGGTAGC (SEQ ID NO: 103) |
| CHST2_7890 | /5AmMC6/GGCATCCTCCCGGTGATGGAAGCAGCCGCCGCCG (SEQ ID NO: 104) |
| OPLAH | /5AmMC6/GGAAGGCGCGGCGCTCGGTCAGCACTGACAGCAG (SEQ ID NO: 105) |
| PDGFD | /5AmMC6/TCGCCGAGCTCTCCCCAAACTTCCTGCATGCTGAACTTT (SEQ ID NO: 106) |
| FLI1 | /5AmMC6/CCGTCCATTTGGCCAAGTCTGCAGCCGAGCC (SEQ ID NO: 107) |
| DTX1 | /5AmMC6/CTGCGTCCGTCCGTCGGCCGGGCAGTCTGTCCA (SEQ ID NO: 108) |
| NDRG4 | /5AmMC6/TCCCTCGCGCGTGGCTTCCGCCTTCTGCGCGGCTGGGGTGCCCGGTGG (SEQ ID NO: 109) |
| BMP3 | /5AmMC6/GCGGGACACTCCGAAGGCGCAAGGAG (SEQ ID NO: 110) |

Each capture probe was synthesized with a 5'-NH2 modification to allow coupling to magnetic particles that are —COOH modified through standard carbodiimide coupling chemistry. Also, a complementary oligonucleotide to the capture probe was synthesized to contain a 5'-Cy3 label. This complementary probe was used to confirm capture probe coupling to magnetic particles.

To test the capture efficiency of each probe as well as assess marker performance, two stool pools of normal and cancer patients were made. The cancer stool pool came from 6 patients (3 are CRC, 1 is an AA and 2 unknowns). Similarly, the normal stool came from 6 non-CRC normal patients. The stool was prepared by mixing the supernatant after homogenate centrifugation. Pooled supernatant was then aliquoted into single capture samples containing 14 mL supernatants.

Capture probes were designed to have a melting temperature of 75-80° C. and lengths between 25-35 bases. Additionally, the capture probe hybridizing region was selected to be within the post-bisulfite QuARTS footprint.

To perform capture, capture beads (magnetic particles with covalently linked capture probes) for two markers plus ACTB capture beads were pooled to form a triplex capture bead pool.

Capture was performed on triplicates 14 mL of positive and normal stool supernatants (exception was VAV3 and DTX1 were performed in duplicates since pool was running low).

After completion of capture, stool DNA was eluted from capture beads with 0.1 N NaOH at 42° C. for 20 minutes followed by bisulfite conversion at 56° C. for 1 hour using ammonium bisulfite. Stool DNA was then desulphonated and purified using silica coated magnetic beads and eluted in 70 uL of 10 mM Tris-HCl, pH 8, 0.1 mM EDTA. 10 uL of eluent was then tested and quantified in QuARTS assays.

To be able to quantifiy samples, pUC57 plasmids with DNA inserts corresponding to the QuARTS footprints were used. The DNA inserts were flanked with EcoRI sites to allow linearization and quantification using absorbance at 260 nm.

To allow for back calculation of strands in the eluted samples, QuARTS assays were performed on the 10 uL of eluents and serial dilutions of the digested plasmids.

Table 6D shows the obtained results for each of the tested markers. These results show that the methylation markers had high strand differences between positive and normal stool pool indicating these markers are candidates for CRC detection in stool.

TABLE 6D

| Methylation Marker | Positives Pool average strands | Normal Pool average strands | Fold differences (Positive/Normal) |
|---|---|---|---|
| NDRG4 | 1,568 | 140 | 11.2 |
| BMP3 | 395 | 8 | 51.4 |
| OPLAH | 840 | 279 | 3.0 |
| FLI1 | 1,715 | 167 | 10.2 |
| PDGFD | 843 | 67 | 12.6 |
| CHST2_7889 | 945 | 17 | 56.4 |
| SFMBT2_895 | 837 | 5 | 152.3 |
| SFMBT2_896 | 856 | 150 | 5.7 |
| SFMBT2_897 | 844 | 45 | 18.7 |
| CHST2_7890 | 1,396 | 62 | 22.6 |
| VAV3 | 367 | 21 | 17.9 |
| DTX1 | 751 | 105 | 7.2 |

Example 4

Exemplary Procedure for Screening for a Colorectal Cancer within a Human Subject.

Contact a nucleic acid (e.g., genomic DNA, e.g., isolated from a body fluids such as a stool sample or colorectal tissue) obtained from a human subject with at least one reagent or series of reagents that distinguishes between methylated and non-methylated CpG dinucleotides within at least one marker DMR selected from:

FLI1, OPLAH, DTX1, MATK, and SFMBT2 region 2; (as recited in Table 1);
BMP3, NDRG4, PDGFG, CHST2, and SFMBT2 (as recited in Table 2);
SFMBT2, LIFR, OPLAH, CRHR2, AGBL4, ZEB2, ZNF788, SFMBT2, ESR1, ANKRD33B, CHST2 and FNDC1 (as recited in Table 3); and
NDRG4, BMP3, OPLAH, FLI1, PDGFD, CHST 7889, SFMBT2_895, SFMBT2_896, SFMBT2_897, CHST2_7890, VAV3, and DTX1 (as recited in Table 6).

Identifying the subject as having a colorectal cancer when the methylation state of the marker is different than a methylation state of the marker assayed in a subject that does not have a neoplasm.

Exemplary Procedure for Screening for a Colorectal Based Large Adenoma within a Human Subject.

Contact a nucleic acid (e.g., genomic DNA, e.g., isolated from a body fluids such as a stool sample or colorectal tissue) obtained from a human subject with at least one reagent or series of reagents that distinguishes between methylated and non-methylated CpG dinucleotides within at least one marker DMR selected from:

ADD2, AGBL4, AKAP12, ANKRD33B, ASCL1, C1orf70, CHST11, CHST15, DTX1, ECEL1, EYA4, FLI1, FLJ43390, FLT3, GRASP, ITGA4, KCNQ2, LOC100131199, LONFR2, MGAT3, OPLAH (145106742-145106921), OPLAH (145106349-145106456), PDE8B, PDGFD, PKIA, POU3F1, QKI, RASSF2, RSPO3, SDC2, SFMBT2 (7452746-7452779), SFMBT2 (7452029-7452452), SFMBT2 (7450242-7450831), SOXS, VAV3 (108507609-108507674), VAV3 (108507074-108507498), and ZNF132 (as recited in Table 4).

Identifying the subject as having a colorectal based large adenoma when the methylation state of the marker is different than a methylation state of the marker assayed in a subject that does not have a neoplasm.

Exemplary Procedure for Screening for Sessile Serrated Polyps (SSP) within a Human Subject.

Contact a nucleic acid (e.g., genomic DNA, e.g., isolated from a body fluids such as a stool sample or colorectal tissue) obtained from a human subject with at least one reagent or series of reagents that distinguishes between methylated and non-methylated CpG dinucleotides within at least one marker DMR selected from:

CAMK4, FGF9, GJC1, GPX7, GRIN2A, IGF2BP3, MAX.chr19.55963254-55963329, MAX.chr2.127783352-127783403, MAX.chr4.186049639-186049660, NRG1, NTNG1, PIK3CD, PTENP1, RAB31, RNF220, SLC30A10, and ZNF853 (as recited in Table 5).

Identifying the subject as having a sessile serrated polyps when the methylation state of the marker is different than a methylation state of the marker assayed in a subject that does not have a neoplasm.

Exemplary Procedure for Screening for a Colorectal Cancer within a Human Subject Having Inflammatory Bowel Disease.

Contact a nucleic acid (e.g., genomic DNA, e.g., isolated from a body fluids such as a stool sample or colorectal tissue) obtained from a human subject having inflammatory bowel disease with at least one reagent or series of reagents that distinguishes between methylated and non-methylated CpG dinucleotides within at least one marker DMR selected from:

BMP3, NDRG4, PDGFG, CHST2, and SFMBT2 (as recited in Table 2).

Identifying the subject as having a colorectal cancer when the methylation state of the marker is different than a methylation state of the marker assayed in a subject that does not have a neoplasm.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method comprising:
   extracting genomic DNA from a stool sample of a human individual suspected of having or having colorectal cancer,
   treating the extracted genomic DNA with bisulfite,
   amplifying the bisulfite-treated genomic DNA using primers specific for a CpG site for LRRC4, primers specific for a CpG site for LASS4, and primers specific for a CpG site for PPP2R5C,
   measuring a methylation level of the CpG site for LRRC4, the CpG site for LASS4 and the CpG site for PPP2R5C.

2. The method of claim 1, wherein measuring a methylation level of the CpG site for LRRC4, the CpG site for LASS4, and the CpG site for PPP2R5C is determined by methylation-specific PCR, quantitative methylation-specific PCR, methylation-sensitive DNA restriction enzyme analysis, or bisulfite genomic sequencing PCR.

3. The method of claim 1, wherein amplifying the bisulfite-treated genomic DNA using primers specific for a CpG site for LRRC4 is a set of primers that specifically binds at least a portion of a genetic region comprising chromosome 7 coordinates 127671918-127672318.

4. The method of claim 1, wherein amplifying the bisulfite-treated genomic DNA using primers specific for a CpG site for LASS4 is a set of primers that specifically binds at least a portion of a genetic region comprising chromosome 19 coordinates 8274584-8274671.

5. The method of claim 1, wherein amplifying the bisulfite-treated genomic DNA using primers specific for a CpG site for PPP2R5C is a set of primers that specifically binds at least a portion of a genetic region comprising chromosome 14 coordinates 102248062-102248216 and/or chromosome 14 coordinates 102247525-102247929.

* * * * *